(12) United States Patent
Shuler

(10) Patent No.: US 11,903,682 B2
(45) Date of Patent: *Feb. 20, 2024

(54) METHOD AND SYSTEM FOR MONITORING OXYGENATION LEVELS OF A COMPARTMENT FOR DETECTING CONDITIONS OF A COMPARTMENT SYNDROME

(71) Applicant: J&M SHULER, INC., Athens, GA (US)

(72) Inventor: Michael Simms Shuler, Athens, GA (US)

(73) Assignee: J&M Shuler, Inc., Athens, GA (US)

( * ) Notice: Subject to any disclaimer, the term of this patent is extended or adjusted under 35 U.S.C. 154(b) by 26 days.

This patent is subject to a terminal disclaimer.

(21) Appl. No.: 17/534,094

(22) Filed: Nov. 23, 2021

(65) Prior Publication Data
US 2022/0192514 A1 Jun. 23, 2022

Related U.S. Application Data

(63) Continuation of application No. 15/088,242, filed on Apr. 1, 2016, now abandoned, which is a continuation
(Continued)

(51) Int. Cl.
*A61B 5/0205* (2006.01)
*A61B 5/1455* (2006.01)
(Continued)

(52) U.S. Cl.
CPC .......... *A61B 5/0205* (2013.01); *A61B 5/0075* (2013.01); *A61B 5/022* (2013.01);
(Continued)

(58) Field of Classification Search
None
See application file for complete search history.

(56) References Cited

U.S. PATENT DOCUMENTS 4,858,620 A * 8/1989 Sugarman ............ A61B 5/1036
600/587
5,873,821 A * 2/1999 Chance ................ A61B 5/6828
600/323

(Continued)

*Primary Examiner* — Meredith Weare
(74) *Attorney, Agent, or Firm* — SMITH TEMPEL; Steven P. Wigmore; Matthew T. Hoots

(57) ABSTRACT

A method and system for continually monitoring oxygenation levels in real-time in compartments of an animal limb, such as in a human leg or a human thigh or a forearm, can be used to assist in the diagnosis of a compartment syndrome. The method and system can include one or more near infrared compartment sensors in which each sensor can be provided with a compartment alignment mechanism and a central scan depth marker so that each sensor may be precisely positioned over a compartment of a living organism. The method and system may comprise hardware or software (or both) may adjust one or more algorithms based on whether tissue being monitored was traumatized or is healthy. The method and system can also monitor the relationship between blood pressure and oxygenation levels and activate alarms based on predetermined conditions relating to the oxygenation levels or blood pressure or both.

6 Claims, 40 Drawing Sheets

Related U.S. Application Data of application No. 14/106,734, filed on Dec. 14, 2013, now Pat. No. 9,314,165, and a continuation of application No. 12/773,312, filed on May 4, 2010, now Pat. No. 8,639,309, which is a continuation-in-part of application No. 11/831,954, filed on Jul. 31, 2007, now Pat. No. 8,100,834.

(60) Provisional application No. 61/176,480, filed on May 7, 2009, provisional application No. 60/903,632, filed on Feb. 27, 2007.

(51) Int. Cl.
*A61B 5/0215* (2006.01)
*A61B 5/022* (2006.01)
*A61B 5/00* (2006.01)
*A61B 5/08* (2006.01)
*A61B 5/024* (2006.01)
*A61B 5/145* (2006.01)

(52) U.S. Cl.
CPC ........ *A61B 5/0215* (2013.01); *A61B 5/02055* (2013.01); *A61B 5/08* (2013.01); *A61B 5/1455* (2013.01); *A61B 5/14552* (2013.01); *A61B 5/412* (2013.01); *A61B 5/416* (2013.01); *A61B 5/4519* (2013.01); *A61B 5/6824* (2013.01); *A61B 5/6828* (2013.01); *A61B 5/742* (2013.01); *A61B 5/746* (2013.01); *A61B 5/024* (2013.01); *A61B 5/082* (2013.01); *A61B 5/0816* (2013.01); *A61B 5/14539* (2013.01); *A61B 5/413* (2013.01); *A61B 5/4504* (2013.01); *A61B 2560/0242* (2013.01)

(56) References Cited

U.S. PATENT DOCUMENTS

| | | | | |
|---|---|---|---|---|
| 6,615,065 | B1* | 9/2003 | Barrett | A61B 5/6814 600/323 |
| 7,596,397 | B2* | 9/2009 | Ortner | A61B 5/14535 600/340 |
| 2006/0063995 | A1* | 3/2006 | Yodh | A61B 5/0261 600/323 |
| 2007/0100218 | A1* | 5/2007 | Sweitzer | A61B 5/0002 600/323 |
| 2008/0146906 | A1* | 6/2008 | Baker | A61B 5/4869 600/407 |
| 2008/0208011 | A1* | 8/2008 | Shuler | A61B 5/7271 600/324 |
| 2009/0221919 | A1* | 9/2009 | Ben Dor | A61B 5/4076 600/407 |
| 2009/0275805 | A1* | 11/2009 | Lane | G06F 9/453 600/300 |
| 2010/0145169 | A1* | 6/2010 | Li | A61B 5/14546 600/323 |
| 2011/0205535 | A1* | 8/2011 | Soller | A61B 5/1455 356/300 |
| 2022/0192501 | A1* | 6/2022 | Shuler | A61B 5/416 |
| 2022/0192514 | A1* | 6/2022 | Shuler | A61B 5/742 |
| 2023/0029444 | A9* | 1/2023 | Shuler | A61B 5/022 |

\* cited by examiner

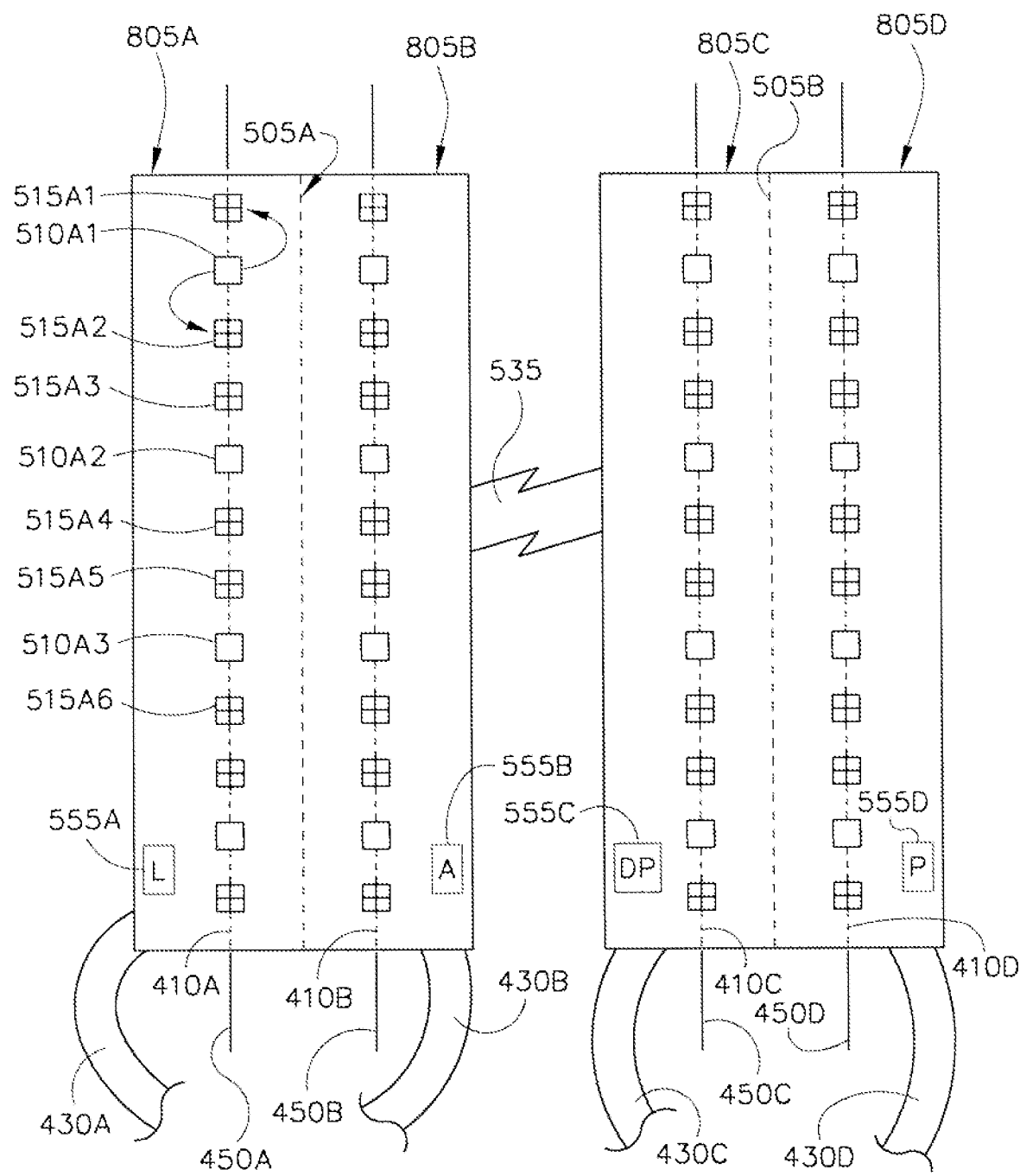

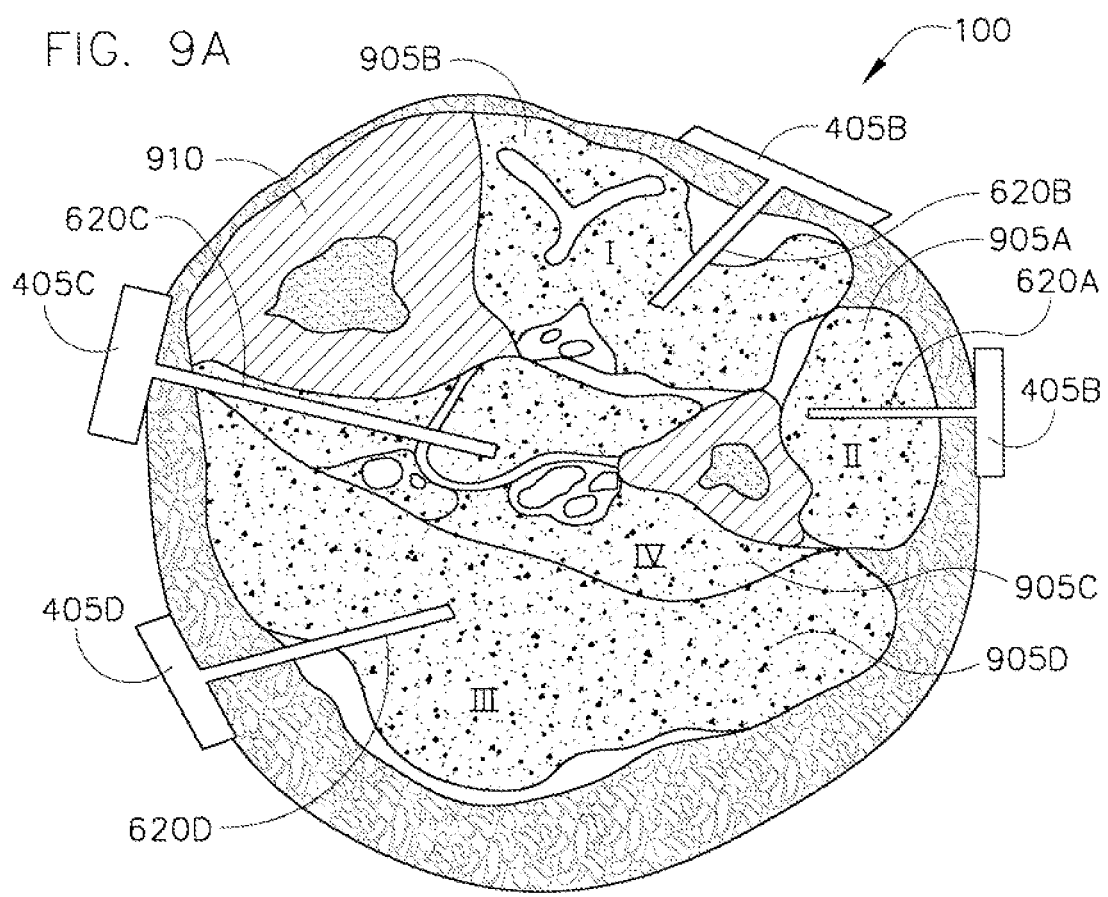
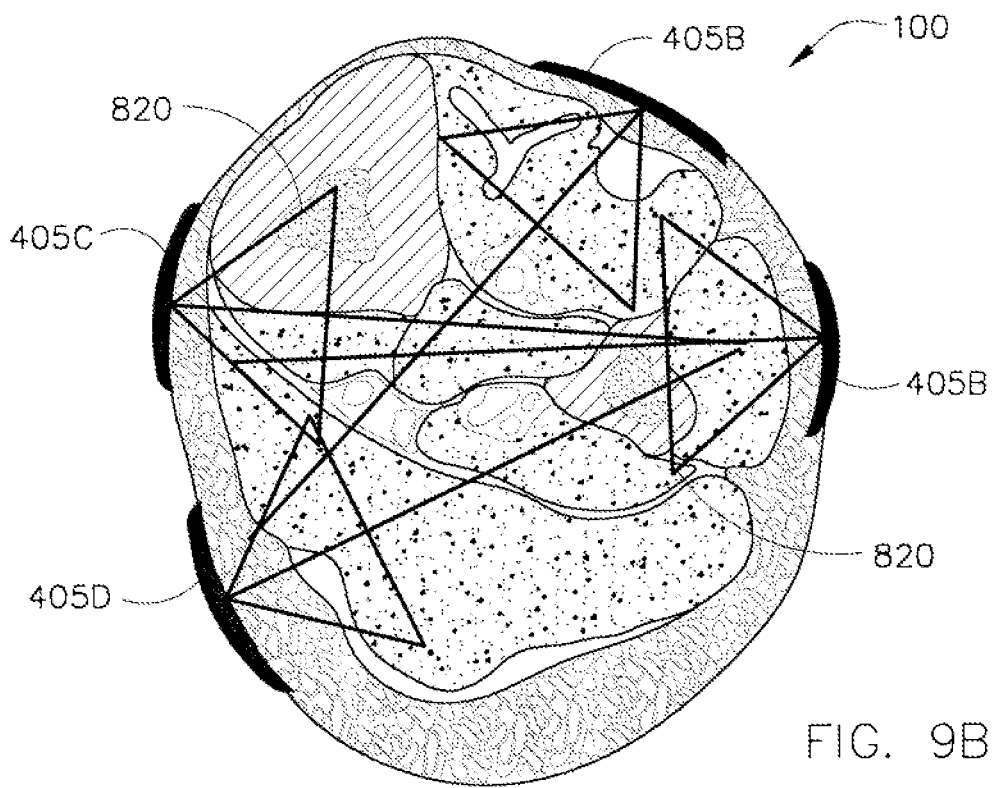

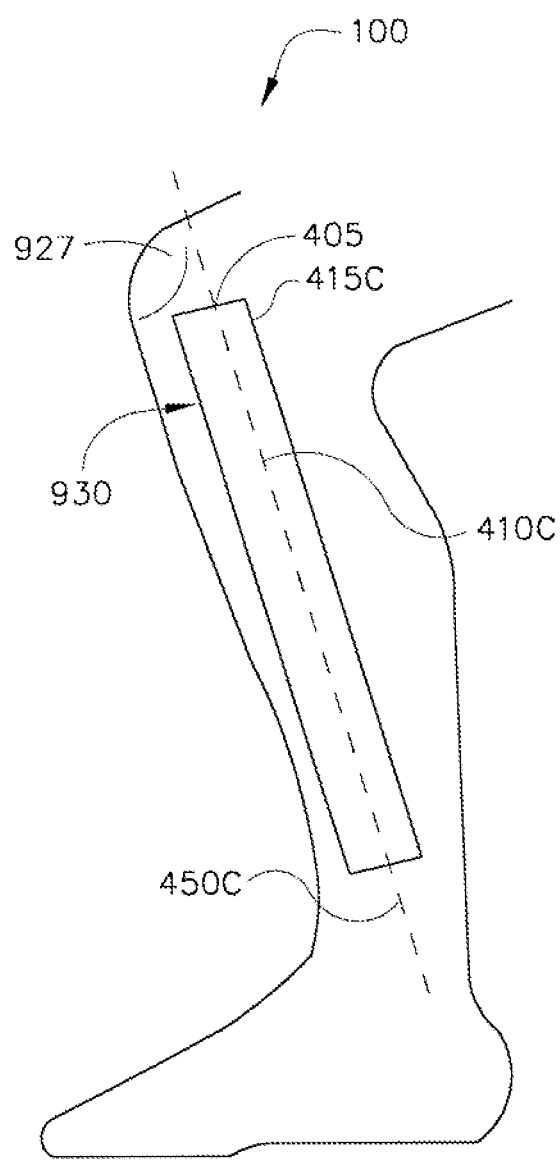

CONNECTING THE ANTERIOR COMPARTMENT
PROVISIONALLY REDUCE ANY FRACTURES TO ALIGN THE LEG
PALPATE THE TIBIAL RIDGE

CONNECTING THE ANTERIOR COMPARTMENT
ALL PADS SHOULD BE PLACED AT MID-TIBIAL LEVEL OR JUST PROXIMAL (TOWARDS THE KNEE)

CONNECTING THE ANTERIOR COMPARTMENT

PLACE THE ANTERIOR (A) SENSOR LATERAL TO THE TIBIAL RIDGE OVER THE MUSCLE (~2cm OFF THE RIDGE)

CONNECTING THE LATERAL COMPARTMENT

AFTER CONNECTING THE SENSOR TO THE APPROPRIATE OUTLET, PLACE THE LATERAL (L) SENSOR OVER THE FIBULA ON THE LATERAL ASPECT OF THE LEG

AGAIN, ENSURE MID-TIBIAL LEVEL

CONNECTING THE DEEP & SUPERFICIAL POSTERIOR COMPARTMENTS

CONNECTING THE DEEP POSTERIOR COMPARTMENT

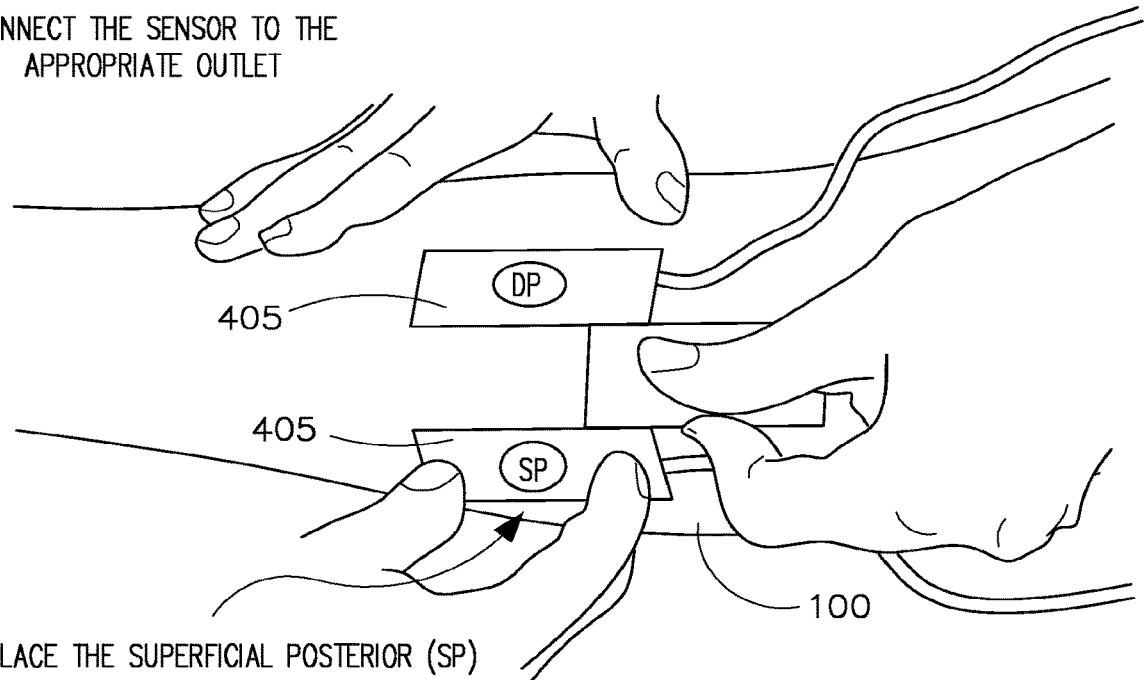

FIG. 29G
CONNECTING THE SUPERFICIAL POSTERIOR COMPARTMENT

CONNECT THE SENSOR TO THE APPROPRIATE OUTLET

PLACE THE SUPERFICIAL POSTERIOR (SP) SENSOR ON THE BACK OF THE LEG. THE SEPARATION BETWEEN THE PADS SHOULD BE APPROXIMATELY ONE PAD'S WIDTH

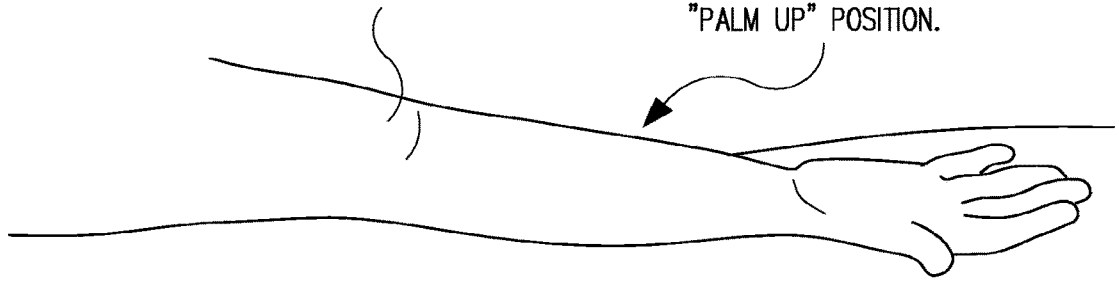

FIG. 31A
PROVISIONALLY REDUCE THE FOREARM FRACTURE.

PLACE THE ARM IN A FULLY SUPINATED POSITION, WITH THE THUMB POINTING AWAY FROM THE BODY, "PALM UP" POSITION.

ALL SENSORS SHOULD BE PLACED ROUGHLY 1/3 DOWN THE FOREARM (CLOSER TO THE ELBOW THAN THE WRIST)

PLACEMENT OF THE FIRST SENSOR

STEP 1) PALPATE THE ULNA. THIS IS THE FOREARM BONE ON THE SMALL FINGER SIDE OF THE ARM.

PLACEMENT OF THE FIRST SENSOR

PLACEMENT OF THE SECOND SENSOR

FIG. 31F
PLACEMENT OF THE THIRD SENSOR

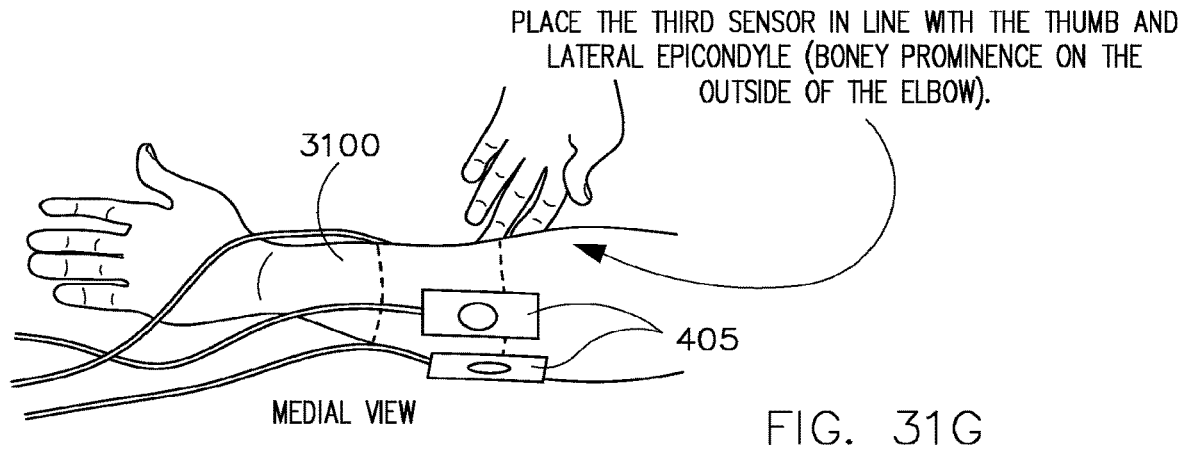

PLACE THE THIRD SENSOR IN LINE WITH THE THUMB AND LATERAL EPICONDYLE (BONEY PROMINENCE ON THE OUTSIDE OF THE ELBOW).

FIG. 31G
PLACEMENT OF THE THIRD SENSOR

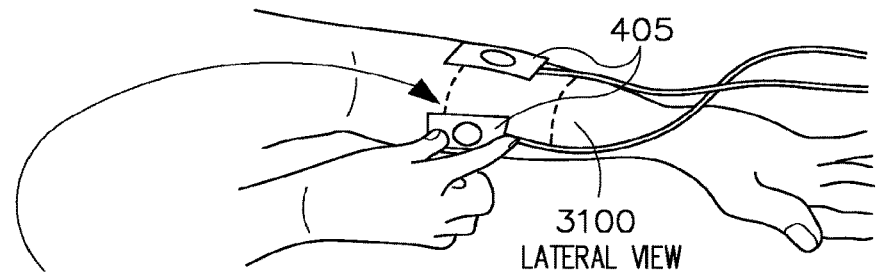

PLACE THE THIRD SENSOR IN LINE WITH THE THUMB AND LATERAL EPICONDYLE (BONEY PROMINENCE ON THE OUTSIDE OF THE ELBOW).

FIG. 31H
PLACEMENT OF THE FOURTH SENSOR

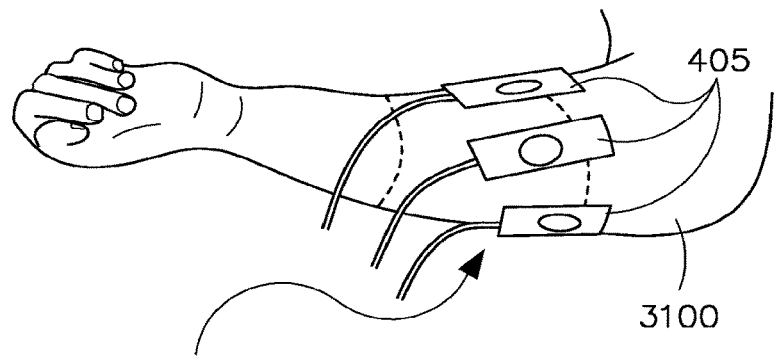

PLACE THE FOURTH SENSOR JUST DORSAL TO THE ULNA, OVER THE EXTENSORS ON THE BACK OF THE FOREARM. THIS WILL BE OVER THE EXTENSOR CARPI ULNARUS (ECU).

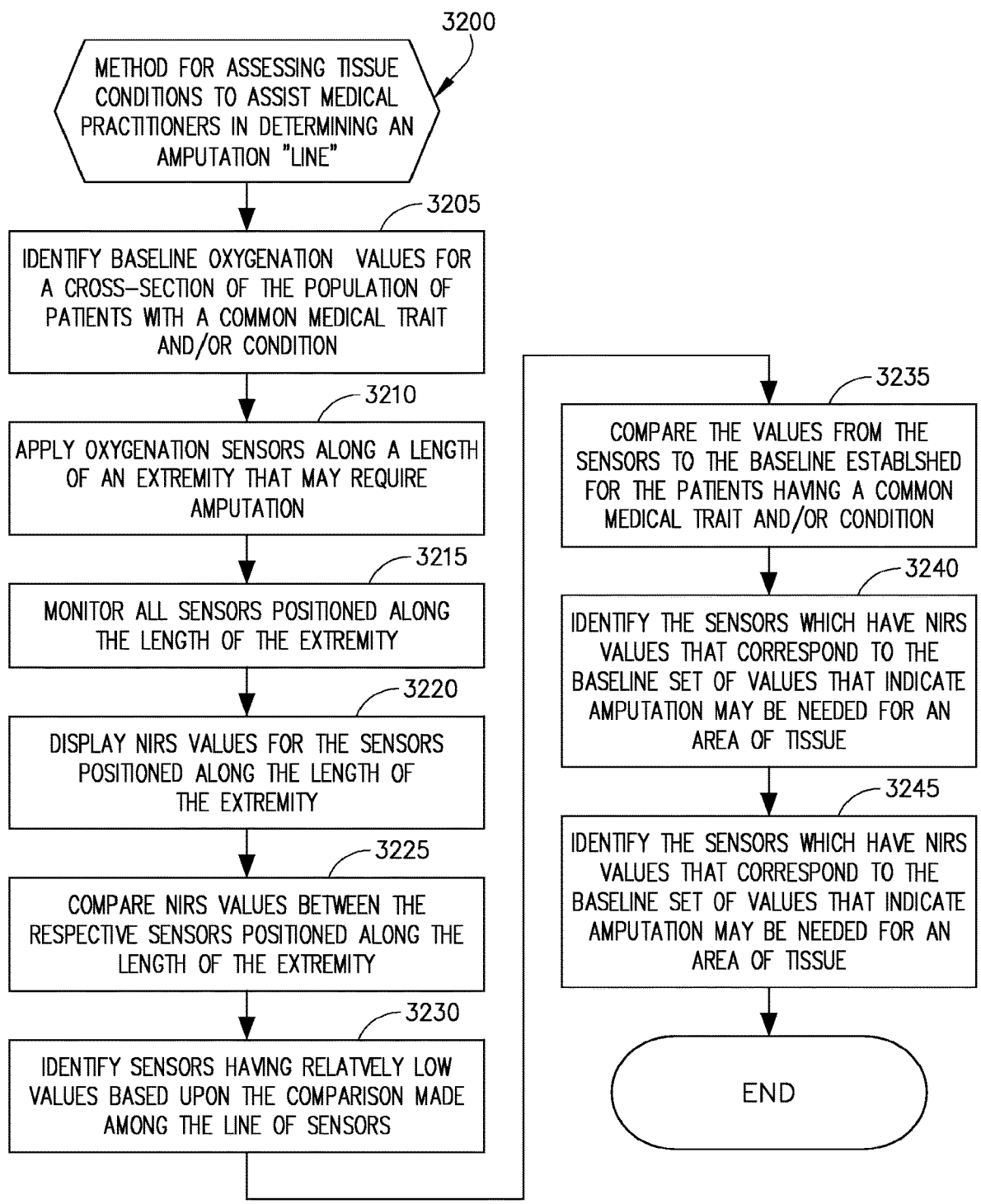

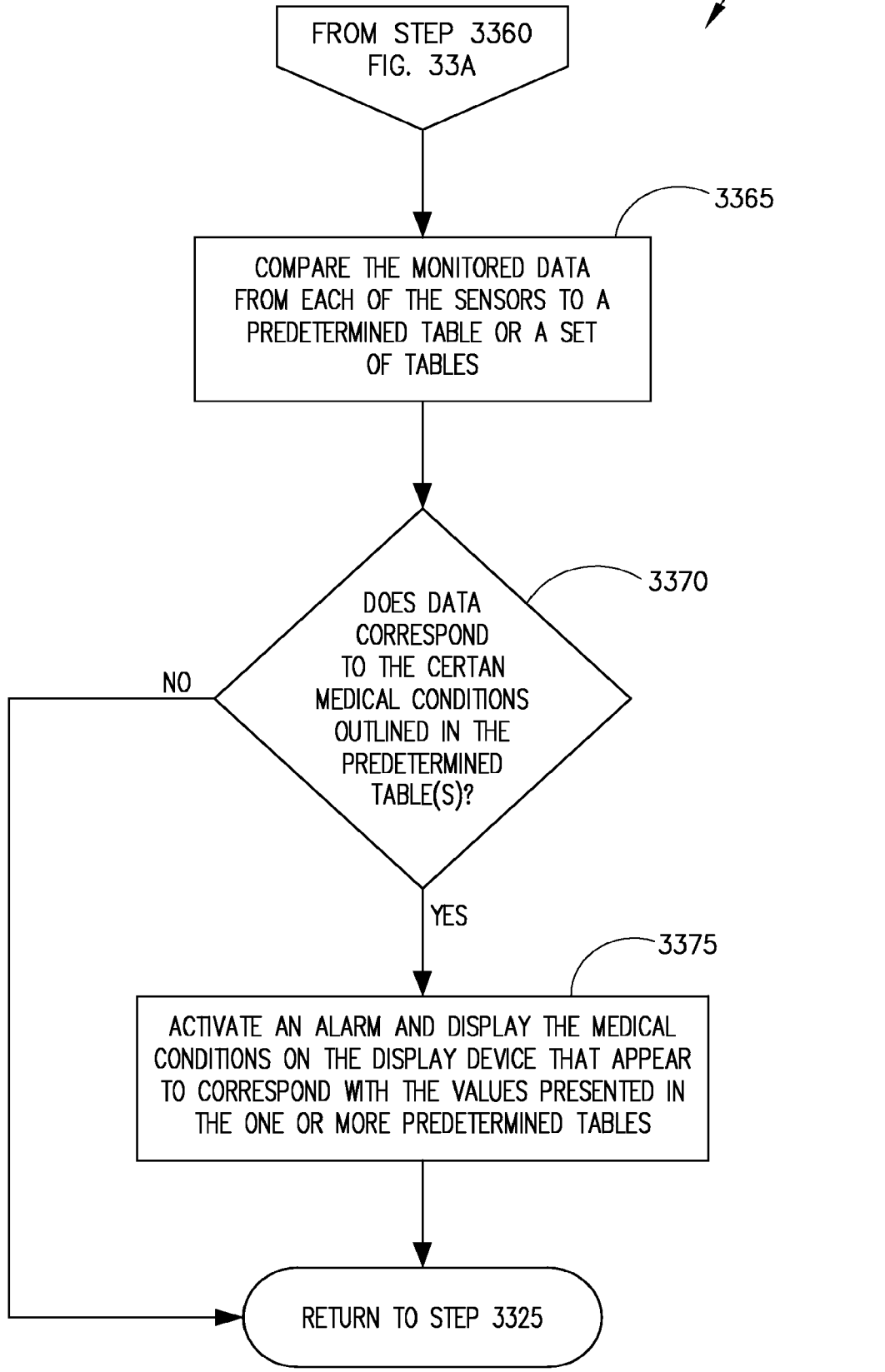

FIG. 34
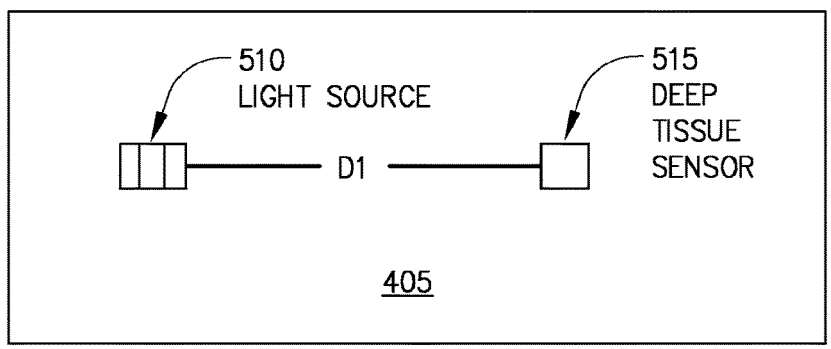
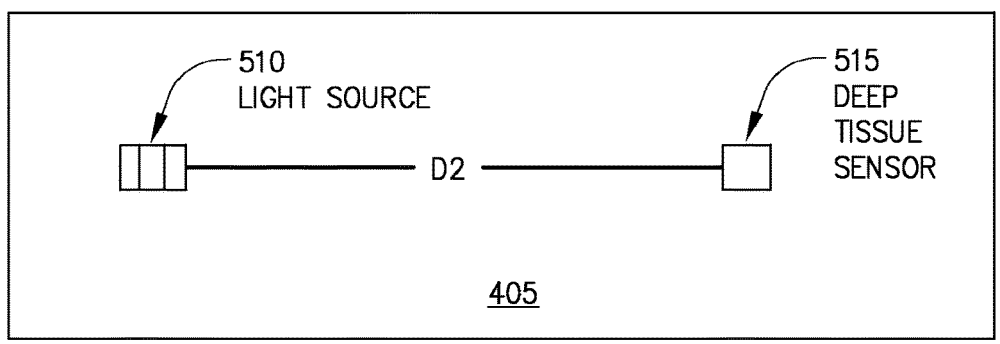
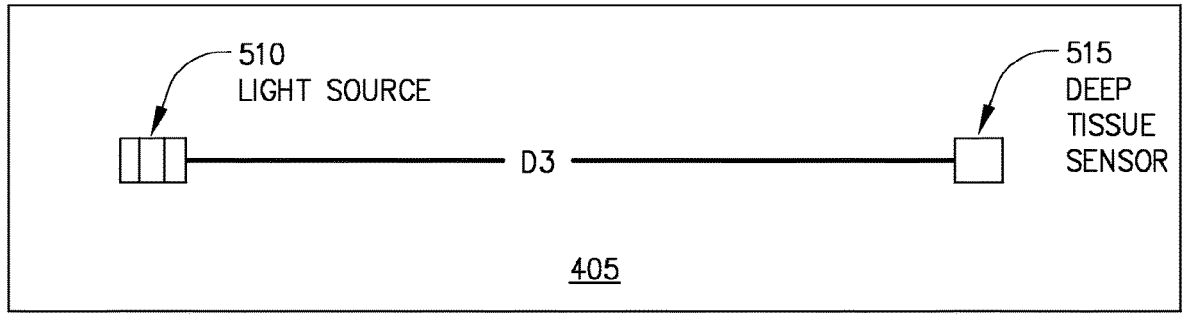

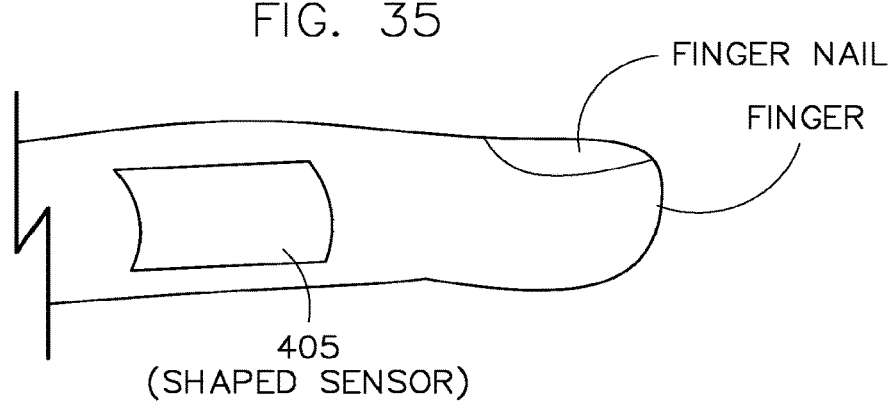
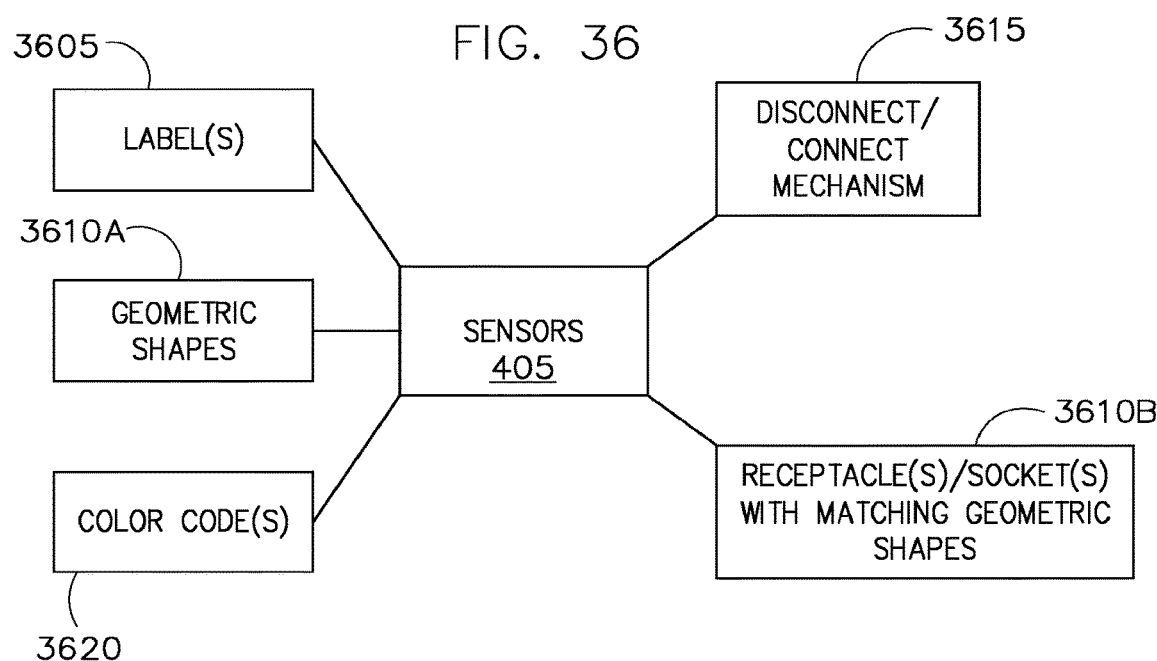
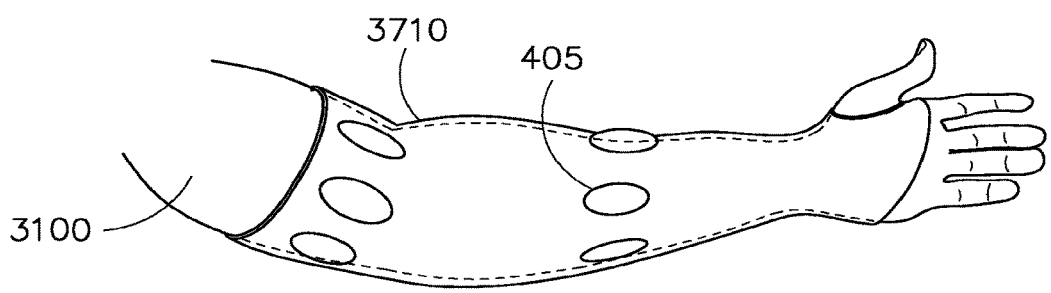

METHOD AND SYSTEM FOR MONITORING OXYGENATION LEVELS OF A COMPARTMENT FOR DETECTING CONDITIONS OF A COMPARTMENT SYNDROME

STATEMENT REGARDING RELATED APPLICATIONS AND PRIORITY CLAIMS

This application is a continuation-in-part of U.S. Non-Provisional patent application Ser. No. 11/831,954 filed on Jul. 31, 2007 entitled, "Method and System for Monitoring Oxygenation Levels of a Compartment for Detecting Conditions of a Compartment Syndrome." This application claims priority to this Non-Provisional patent application under 35 U.S.C. § 120. This application also claims priority under 35 U.S.C. 119(e) to U.S. Provisional Patent Application Ser. No. 61/176,480 filed on May 7, 2009 entitled, "Method and System for Monitoring Oxygenation Levels of Compartments and Tissue." The entire contents of both the provisional patent application and non-provisional patent application are hereby incorporated by reference.

FIELD OF INVENTION

The invention relates to a coordinated, continual and real-time method and system for monitoring oxygenation levels of a compartment and other tissue. More particularly, the invention relates to an orchestrated method and system that monitors oxygenation levels of compartments as well as other tissue such as traumatized tissue.

BACKGROUND OF THE INVENTION

Compartment syndrome is a medical condition where the pressure inside a compartment, which is a muscle group surrounded by fascia or a thin, inelastic film, increases until the blood circulation inside the volume defined by the fascia or thin film is cut off. The most common site, in humans, occurs in the lower leg, and more specifically, in regions adjacent to the tibia and fibula. There are four compartments in the lower, human leg: the anterior (front), lateral (side next to the fibula) and the deep and superficial posterior (back).

These four compartments surround the tibia and fibula. Anyone of these four compartments can yield a compartment syndrome when bleeding or swelling occurs within the compartment. Compartment syndrome usually occurs after some trauma or injury to the tissues, such as muscles or bones or vessel (or all three), contained within the compartment. Bleeding or swelling within a compartment can cause an increase in pressure within that compartment. The fascia does not expand, so as pressure rises, the tissue and vessels begin to be compressed within the compartment.

This compression of tissue, such as muscle, due to intra-compartmental pressure can restrict and often times stop blood flow from entering the compartment that is destined for any tissues contained within the compartment. This condition is termed ischemia. Without blood flow to tissues, such as muscle, the tissues will eventually die. This condition is termed necrosis.

A simple working definition for a compartment syndrome is an increased pressure within a closed space which reduces the capillary blood perfusion below a level necessary for tissue viability. As noted above, this situation may be produced by two conditions. The first condition can include an increase in volume within a closed space, and the second condition is a decrease in size of the space.

An increase in volume occurs in a clinical setting of hemorrhage, post ischemic swelling, re-perfusion, and arterial-venous fistula. A decrease in size results from a cast that is too tight, constrictive dressings, pneumatic anti-shock garments, and closure of fascial defects. As the pressure increases in tissue, it exceeds the low intramuscular arteriolar pressure causing decreased blood in the capillary anastomosis and subsequent shunting of blood flow from the compartment.

The clinical conditions that may be associated with compartment syndrome include the management of fractures, soft tissue injuries, arterial injuries, drug overdoses, limb compression situations, burns, post-ischemic swelling, constrictive dressings, aggressive fluid resuscitation and tight casts.

Referring now to the Figures, FIG. 1 illustrates an X-ray view of a human leg 100 with fractured bones of the tibia 105 and fibula 110 that lead to one or more compartment syndromes in the muscles 115 surrounding the bones of the human leg 100. The tibia 105 and fibula 110 usually bleed in regions proximate to the physical break regions 120. This bleeding can form a large pool of stagnant blood referred to as a hematoma. The hematoma can start pressing upon muscles 115 that may be proximate to the break 120. This pressure caused by the hematoma can severely restrict or stop blood flow into the muscles 115 of a compartment, which is the diagnosis of a compartment syndrome.

Traditional Methods for Diagnosing Compartment Syndromes

Referring now to FIG. 2, this Figure is a side view of a human leg 100 in which compartment pressures are being measured with a large bore needle 200, having a gauge size such as 14 or 16 (which is the largest needle in the hospital available to clinicians), according to a conventional method known in the prior art. While compartment pressures can be measured with this conventional method, the method is highly invasive procedure which can cause tremendous pain to the patient. Needles with large gauge sizes of 14 or 16 are analogous to sticking a patient with an object as large as a nail or a pen.

In addition to causing tremendous pain to the patient, there are several more problems associated with the conventional needle measuring method. First, it is very challenging for a medical practitioner to actually measure or read pressure of a compartment since the needle must be positioned at least within the interior of a compartment. To enter the interior of a compartment, the needle 200 must penetrate through several layers of skin and muscle. And it is very difficult for the medical practitioner to know if the needle has penetrated adequately through the intermediate layers to enter into the compartment. This challenge significantly increases if the patient being measure is obese and has significant amounts of subcutaneous fat in which to penetrate with the needle.

Often, the medical practitioner may not have a needle accurately positioned inside a compartment which can yield a reading of the tissue adjacent to the compartment, such as muscle or skin. Such a reading of muscle or skin instead of the compartment of interest can provide the medical practitioner with elevated or depressed pressure readings that do not reflect the actual pressure contained within the compartment of interest. Pressure readings inside a compartment have been shown to vary (increase) based on the depth of the reading as well as the proximity to the fracture site.

Because of the challenge medical practitioners face with precisely positioning a needle within a compartment of interest and because of the numerous law suits associated with the diagnosis of compartment syndrome, many medical schools do not provide any formal training for medical practitioners to learn how to properly place a needle within a compartment of interest for reading a compartment's pressure. Therefore, many medical practitioners are not equipped with the skills or experience to accurately measure compartment pressures with the needle measuring method.

Currently, intra-compartmental pressures are the only objective diagnostic tool. Due to the legal climate regarding this condition, clinicians are forced to treat an elevated value for compartment pressures or expose themselves to legal ramifications with any complications. As described later, the treatment of compartment syndrome can cause significant morbidity and increase the risk for infection. Therefore inaccurate and elevated pressure readings are a very difficult and potential dangerous pitfall.

Another problem associated with the training and experience required for the needle measuring method is that, as noted above, compartment syndromes usually occur when tissues within the compartment are experiencing unusual levels of swelling and pressure. With this swelling and pressure, the tissues do not have their normal size. Therefore, any training of a medical practitioner must be made with a patient suffering under these conditions. A normal patient without any swelling would not provide a medical practitioner with the skills to accurately assess a size of a compartment when using the needle measuring method for determining compartment pressure. Put another way, due to the trauma associated with the injury, normal anatomy is not always present when attempting to measure compartment pressures.

In addition to the problem of entering a compartment that may have an abnormal size or anatomy, the needle measuring method has the problem of providing only a snap-shot of data at an instant of time. When the conventional needle measuring method is used, it provides the medical practitioner with pressure data for a single instant of time. In other words, the needle pressure method only provides the medical practitioner with one data point for a particular time. Once pressure is read by the medical practitioner, he or she usually removes the needle from the patient. The data obtained from a single measurement in time gives no information concerning the pressure trend, and the direction the intra-compartmental pressure is moving.

This collection of single data points over long periods of time is usually not very helpful because pressures within a compartment as well as the patient's blood pressure can change abruptly, on the order of minutes. Also, because of the pain associated with the needle measuring method noted above, the medical practitioner will seldom or rarely take pressure readings with within a few minutes of each other using a needle.

A further problem of the needle measuring method is that for certain regions of the body, such as the lower leg, there are four compartments to measure. This means that a patient's leg must be stuck with the large bore needle at least four times in order for a medical practitioner to rule out that a compartment syndrome exists for the lower leg. In the lower leg of the human body, one compartment is located under a neighboring compartment such that a needle measurement may be needed in at least two locations that are very close together, but in which the medical practitioner must penetrate tissues at a shallow depth at a first location to reach the first compartment; and for reaching the second compartment that is underneath the first compartment, a large depth must be penetrated by the needle, often with the needle piercing the first compartment and then the second compartment.

Another problem, besides pain that is associated with the needle pressure measuring method, is that there is a lack of consensus among medical practitioners over the compartment pressure ranges which are believed to indicate that a compartment syndrome may exist for a particular patient. Normal compartment pressure in the human body usually approaches 4 mmHg in the recumbent position. Meanwhile, scientists have found that an absolute pressure measurement of 30 mmHg in a compartment may indicate presence of compartment syndrome. However, there are other scientists who believe that patients with intracompartmental pressures of 45 mmHg or greater should be identified as having true compartment syndromes. But other studies have shown patients with intra-compartmental pressures above these limits with no clinical signs of compartment syndrome. Additional studies have shown that a pressure gradient based on perfusion pressure (diastolic blood pressure minus intra-compartmental pressure) is the more important variable. Studies have shown in a laboratory setting that once the perfusion pressure drops to 10 mm Hg tissue necrosis starts to occur.

Other subjective methods for diagnosing compartment syndromes instead of the needle measuring method exist, however, they may have less accuracy than the needle measuring method because they rely on clinical symptoms of a patient. Some clinical symptoms of a patient used to help diagnose compartment syndromes include pulselessness (absence of a pulse), lack of muscle power, pain, parastesias, and if the flesh is cold to touch. Pain out or proportion and with passive stretch are considered the earliest and most sensitive, but both are very low specificity. One of the major drawbacks of these symptoms is that for many of them the patient must be conscious and must be able to respond to the medical practitioner. This is true for the muscle power and pain assessment. For any inebriated patients or patients who are unconscious, the pain assessment and muscle power assessment cannot be used accurately by the medical practitioner. In the setting of high energy trauma which is associated with compartment syndrome, many patients are not capable of cooperating with a good physical exam due to any number of causes including head trauma, medical treatment (including intubation), drug or alcohol ingestion, neurovascular compromise or critical and life threatening injuries to other body systems.

For the pain assessment, if a lower leg compartment syndrome exists in a patient, then the range of motion for a patient's foot or toes will be extremely limited and very painful when the patient's foot or toes are actively or passively moved. The pain from a compartment syndrome can be very immense because the muscles are deprived of oxygen because of the compartment syndrome.

Another drawback using pain to assess the likelihood of a compartment syndrome is that every human has a different threshold for pain. This means that even if someone should be experiencing a high level of pain, he or she may have a high threshold for pain and therefore, not provide the medical practitioner with a normal reaction for the current level of pain. Another problem with using pain to assess the likelihood of the existence of a compartment syndrome is that if the patient is experiencing trauma to other parts of their body, he or she may not feel the pain of a compartment syndrome as significantly, especially if the trauma to the other parts of the patient's body is more severe. This condition is termed a distracting injury. On the other hand, trauma causes the initial injury that precipitates a compartment syndrome. That initial trauma by definition will cause a baseline amount of pain that is often very difficult to separate from a potential compartment syndrome pain. These initial injuries by themselves cause significant pain, so a patient that does not tolerate pain well may present similar to a compartment syndrome without having any increased pressures simply because they react vehemently to painful conditions.

Conventional Non-Invasive Techniques for Measuring Oxygenation Levels of a Compartment Non-invasive measuring of compartment syndromes using near infrared sensors, such as spectrophotometric sensors, to measure oxygenation levels within a compartment has been suggested by the conventional art. However, these conventional techniques have encountered the problem of a medical practitioner locating compartments of interest and accurately and precisely positioning a sensor over a compartment of interest. Often the orientation of the scan and the depth of the scan produced by a near infrared sensor as well as the orientation of a compartment can be challenging for a medical practitioner to determine because conventional sensors are not marked with any instructions or visual aids. Another problem faced by the medical practitioner with conventional non-invasive techniques is determining how to assess the oxygenation level of compartments that lie underneath a particular neighboring compartment, such as with the deep posterior compartment of the human leg.

In trauma settings, near infrared sensors often do not work when they are placed over regions of the body that have hematomas or pools of blood. In such conditions, a medical practitioner usually guesses at what regions of the human body do not contain any hematomas that could block compartment measurements. Also, conventional near infrared sensors typically are not sterilized and cannot be used in surgical or operating environments.

Near infrared sensors (NIRS) in their current form are limited to a single sensor with a single sensor depth. They also can be affected by skin pigmentation that is not accounted for in the current technology. Placement of the sensor can be difficult since an expanding hematoma can block a previously acceptable placement. Additionally, the only system as of this writing is a single monitor system. There is no product available at this time which will allow for multiple areas to be monitored in close proximity to one another without the potential for interference from other sensor light sources.

Treatment for Compartment Syndrome

Referring now to FIG. 3, this figure is a side view of a human leg 100 in which a surgical procedure, known as a fasciotomy, was performed in order to release the pressures in one or more compartments surrounding the bones of the leg according to a technique known in the art in order to alleviate a compartment syndrome that was diagnosed. This surgical procedure includes an incision 300 that is made along the length of the leg 100 and is generally as long as the compartments contained within the leg 100. While a single incision 300 is illustrated in FIG. 3, a second incision is made on the opposing side of the leg so that a patient will have two incisions on each side of his leg 100. These incisions typically extend from near the knee to near the ankle on each side of the leg.

This procedure is very invasive and it often leaves the patient with severe scars and venous congestion once healed. Also the procedure increases a patient's chances of receiving an air-borne infection because the incisions made on either side of the leg are usually left open for several days in order to allow for the swelling and excess bleeding to subside. Fasciotomies transform a closed fracture (one in which the skin is intact and minimal risk of infection) to an open fracture. Open fractures have a much higher risk of bone infections which requires multiple surgical debridements and ultimately amputation in some cases in ordered to appropriately treat. Additionally, some wound cannot be closed and require skin transfers, or skin grafts, from other parts of the body, usually from the anterior thigh.

Therefore, it is quite apparent that accurately diagnosing compartment syndrome is critical because any misdiagnosis can lead to significant morbidity. A missed compartment syndrome can result in an insensate and contracted leg and foot. A fasciotomy which is highly invasive procedure and which exposes a patient to many additional health risks should not be performed in the absence of a compartment syndrome.

Additionally, time is an important factor in the evaluation of these patients. Ischemic muscle begins to undergo irreversible changes after about six hours of decreased perfusion. Once irreversible changes or necrosis occur, a fasciotomy should not be performed. Fasciotomies in the setting of dead muscle only increase the risk for severe infections and other complications. Late fasciotomies have been shown to have approximately a 50-75% risk of complication. Therefore, fasciotomies need to be performed early but judiciously in patients that are often unresponsive or uncooperative in order to prevent severe morbidity.

Accordingly, there is a need in the art for a non-invasive, real time method and system that monitors oxygenation levels of a compartment and that is provided with sensors which can be precisely positioned over a compartment of interest in order to assist in assessing conditions associated with a compartment syndrome. A further need exists in the art for a non-invasive method that monitors oxygenation levels of a compartment over long periods of time at frequent time intervals and that can monitor different compartments that may be in close proximity with one another. Another need exists in the art for oxygenation sensors that can be fabricated to fit the size of compartments of interest. There is also a need in the art for a non-invasive method and system that monitors oxygenation levels and that can identify ideal locations along a human body in which to conduct scans for deep compartments. There is another need in the art for sterile, non-invasive oxygenation sensors that can be used under surgical and operating conditions. There is a need for multiple locations and multiple compartments to be monitored in a continual and orchestrated manner by a single system. In other words, multiple monitors coordinated to limit noise and continually monitor multiple compartments are needed in the art.

SUMMARY OF THE INVENTION

A method and system for monitoring oxygenation levels in compartments of an animal limb, such as in a human leg or a human thigh or a forearm, can be used to assist in the diagnosis of a compartment syndrome. The method and system can include one or more near infrared compartment sensors in which each sensor can be provided with a compartment alignment mechanism and a central scan depth marker so that each sensor may be precisely positioned over a compartment of a living organism, such as a compartment of a human leg or human thigh or forearm. The method and system can include a device for displaying oxygenation levels corresponding to respective compartment sensors that are measuring oxygenation levels of a compartment of interest.

The alignment mechanism of a compartment sensor can include a linear marking on a surface of the compartment sensor that is opposite to the side which produces a light scan used to detect oxygenation levels. The linear marking can be used by a medical practitioner to align a compartment sensor with the longitudinal axis of a compartment.

The central scan depth marker can include a linear marking positioned on a surface of a compartment sensor that intersects the alignment mechanism, a crosshatch, at a location along the alignment mechanism that denotes the deepest region of a light scan produced by the compartment sensor. The depth of measurement can be displayed in numeric form over the crosshatch guide to aid the clinician since depth varies based on light source & receptor separation. The central scan depth marker can insure that a medical practitioner properly aligns the compartment sensor at a location that will measure a compartment of interest.

According to one exemplary embodiment of the invention, in addition to each compartment sensor having a compartment alignment mechanism and a central scan depth marker, the compartment sensors can be grouped in pairs and share a common supporting substrate. The common supporting substrate can include a separation device, such as, but not limited to, a perforated region. The separation device, such as a perforated region, can be torn or broken by the user in order to adjust for a size of a compartment of interest. In other words, with the separation device, a pair of two compartment sensors can be physically divided so that the sensors do not share a common substrate after the separation device is utilized.

According to another exemplary embodiment of the invention, a compartment sensor can include one light emitting device and two different sets of light detectors such that the compartment sensor can provide a first, shallow oxygenation scan at a first depth and a second, deep oxygenation scan at a second depth. The second depth can be greater than the first depth, so that a general computing device coupled to the two compartment sensors can be programmed or hardwired to calculate the second, deep oxygenation level at the second depth by subtracting data generated by the first, shallow oxygenation level at the first depth.

According to another alternate exemplary embodiment of the invention, several individual compartment scanners can be grouped together along a longitudinal axis of a common supporting material to define a linear compartment array. The linear compartment array can also include a linear marking on its surface and that is opposite to the side which produces the light scan as well as multiple crosshatches for depth denotation. The linear marking can be used to align linear compartment array with a longitudinal axis of a compartment.

According to another exemplary embodiment of the invention, a compartment sensor or compartment sensor array can be positioned at a predetermined position along a human leg in order to measure a deep posterior compartment of the human leg. Position is posteromedial to the posterior aspect of the tibia.

According to one exemplary embodiment of the invention, a linear compartment sensor array can include individual sensors that scan at different depths such that the linear compartment sensor array as a whole has a varied scan depth along its longitudinal axis to more closely match the topography, shape, or depth of a compartment of interest that has a corresponding varied depth. According to another exemplary embodiment of the invention, each individual compartment sensor can produce its oxygenation scan at a predetermined interval such that each individual compartment sensor is only activated one at a time or in a predetermined sequence so that any two or more sensors are not working at a same instant of time in order to reduce any potential for light interference among the different oxygenation scans produced by respective sensors of the array.

According to a further exemplary embodiment of the invention, each compartment sensor can use optical filters in combination with different wavelengths of light so that two or more compartment sensors can scan at the same without interfering with one another. According to another exemplary embodiment of the invention, a linear compartment array can include optical transmitters that are shared among pairs of optical receivers. For example, a single optical transmitter can be used with two optical receivers that are disposed at angles of one-hundred eighty degrees relative to each other and the optical transmitter along the axis of the compartment.

According to yet another exemplary embodiment, a compartment sensor or compartment sensor array can be made from materials that can be sterilized and used in operating environments that are free from germs or bacteria. A compartment sensor or compartment sensor array can also be provided with a coating that is sterilazable or sterilized. When a compartment sensor or compartment sensor array is sterilized, it can be provided underneath bandages or dressings adjacent to a wound or injury of a compartment or proximate to compartment of interest. Each sensor can be provided with a common and sufficient length of cord, such as on the order of approximately ten feet, to allow the cord to extend off the sterile operative field.

According to another exemplary embodiment of the invention, the compartment monitoring method and system can include a device that displays oxygenations levels of a compartment over time in which oxygenation levels are measured at a particular time frequency, such as, but not limited to, on the order of seconds or minutes. According to another exemplary embodiment of the invention, the compartment monitoring system and method can display all measured data from all sensors on the same screen. The display can also show a differential between injured and uninjured leg values of the concordant compartments.

For example, the screen can display calculations of the difference between the values of the anterior compartment of both the injured leg and the contralateral uninjured leg (control leg) to help evaluate the perfusion of the injured leg. According to an alternate exemplary embodiment of the invention, the compartment monitoring system and method can display anatomical features and locations for positioning the sensors of the system along compartments of interest selected by a user. This program at initial set up can help insure proper placement of the sensor by the clinician by using diagrams for accurate placement for each of the labeled sensors or sensor arrays.

According to another exemplary embodiment of the invention, the compartment monitoring system can detect changes in a size of a hematoma when at least one linear compartment arrays is used to measure oxygenations levels at different positions of a compartment. Alternatively, the compartment monitoring system can provide information on varies levels of blood flow along the longitudinal axis of a compartment when at least one linear compartment array is used to measure oxygenations levels at different positions of a compartment.

Alternatively, according to another exemplary embodiment of the invention, a compartment sensor can be provided with a skin pigment sensor that has a known reflectance and that can be used to calibrate the compartment sensor based on relative reflectance of skin pigment which can affect data generated from oxygenation scans. For example, a skin narrow-band simple reflectance device, a tristimulus colorimetric device, or scanning reflectance spectrophotometer can be incorporated into the oxygenation sensor system to obtain a standardized value for skin pigmentation which evaluate melanin and hemoglobin in the skin.

Once the skin melanin is determined it can be correlated to its calculated absorption or reflectance (effect) on the NIRS value using a predetermined calibration system. This effect, optical density value, can be incorporated in tissue hemoglobin concentration calculations in the deep tissue. Accounting for skin pigmentation will usually allow for information or values to be compared across different subjects with different skin pigmentation as well as using the number as an absolute value instead of monitoring simply changes in value over time.

According to an exemplary embodiment of the invention, a compartment sensor can be provided with layers of a known thickness and a know absorption in order to reduce the depth of an oxygenation scan by the sensor so that a thin layer of tissue, such as skin can be measured by the sensor. In other words, due to limitations of how close the light source and receptor can be positioned, in order to evaluate very superficial layers such as skin, the sensor can be separated from the skin of the subject by fixed amount with a known material. For example, by using a material with a known optical density, the length of a scan can be shortened by projecting the light pathway mostly through the known material.

The light pathway would escape the know material only at the maximum depth to evaluate a limited depth of tissue such as skin. This technique would allow for direct measurement of the skin pigmentation effects on the system. This skin sensor can be either incorporated into the compartment monitoring system directly or used to construct the predetermined calibration for skin reflectance values that can be used by the compartment monitoring system.

According to another exemplary embodiment of the invention, the compartment monitoring system can receive data from a blood pressure monitoring system in order to correlate oxygenation levels with blood pressure. The compartment monitoring system that includes a blood pressure monitoring system can activate an alarm, such as an audible or visual alarm (or both), when the diastolic pressure of a patient drops since it has been discovered that perfusion can be significantly lowered or stopped at low diastolic pressures and when compartment pressures are greater than the diastolic pressure.

According to another exemplary embodiment, the compartment monitoring system can increase a frequency of data collection for oxygenation levels and/or blood pressure readings when low blood pressure is detected by the system. According to an alternative exemplary embodiment, the compartment monitoring system can display blood pressure and oxygenation levels simultaneously and in a graphical manner over time, such as an X-Y plot in a Cartesian plane or as two separate graphs over time. Correlation between hemoglobin concentration and diastolic pressure can be used to estimate intra-compartmental pressures without having to use invasive needle measurements.

According to another further exemplary embodiment, the inventive system can incorporate oxygenation levels from both lower extremities and compare values between the legs or other body parts. Initial data from patients with extremity injuries by the inventor have shown that muscular skeletal injuries cause hyperemia (increased blood flow and oxygen) in the injured extremity. If a compartment syndrome develops, the oxygenation drops from an elevated state to an equal and then lower level with comparison to the uninjured limb. Therefore when comparing injured and uninjured extremities, the injured limb may show increased oxygenation levels. If levels begin to drop in the injured limb compared to the uninjured limb, an alarm or alert can be triggered to alert the clinician. A display for the blood pressure being measured can also be provided by the system.

BRIEF DESCRIPTION OF THE DRAWINGS

FIG. 8B illustrates a linear compartment sensor array that can include optical transmitters that are shared among pairs of optical receivers according to one exemplary embodiment of the invention.

FIG. 9A illustrates a cross-sectional view of a left-sided human leg that has the four major compartments which can be measured by the compartment sensors according to one exemplary embodiment of the invention.

FIG. 9B illustrates a cross-sectional view of a right-sided human leg and possible interference between light rays of simultaneous oxygenation scans made by the compartment sensors into respective compartments of interest according to one exemplary embodiment of the invention.

FIG. 9C illustrates a position of a compartment sensor in relation to the knee for the deep posterior compartment of a right sided human leg according to one exemplary embodiment of the invention.

FIGS. 29A-G illustrate various locations for single compartment sensors that can be positioned on a leg of an animal body, such as a human, to measure oxygenation levels of various compartments according to exemplary embodiments of the invention.

FIGS. 31A-H illustrate various locations for single compartment sensors that can be positioned on an arm of an animal body, such as a human, to measure oxygenation levels of various compartments according to exemplary embodiments of the invention.

FIG. 32 is a logic flow diagram illustrating an exemplary method for assessing tissue conditions to help medical practitioners determine an amputation "line" or "level" according to one exemplary embodiment of the invention.

FIGS. 33A-33B provide a logic flow diagram illustrating an exemplary method for assessing monitored conditions to help medical practitioners determine if a patient is experiencing anemia and/or shock according to one exemplary embodiment of the invention.

FIG. 34 illustrates various sizes for sensors according to one exemplary embodiment of the invention.

FIG. 35 illustrates a sensor having a predetermined geometric shape that mirrors the geometric shape of a particular portion of a human anatomy according to one exemplary embodiment of the invention.

FIG. 36 illustrates various physical features that may be provided for a sensor according to one exemplary embodiment of the invention.

FIG. 37 illustrates sensors positioned along a length of a sleeve according to one exemplary embodiment of the invention.

DETAILED DESCRIPTION OF EXEMPLARY EMBODIMENTS

A method and system for monitoring oxygenation levels in compartments of an animal limb, such as in a human leg or a human thigh or a forearm, can be used to assist in the diagnosis of a compartment syndrome. The method and system can include one or more near infrared compartment sensors in which each sensor can be provided with a compartment alignment mechanism and a central scan depth marker so that each sensor may be precisely positioned over a compartment of a human leg or human thigh or forearm. The method and system can include a device for displaying oxygenation levels corresponding to respective compartment sensors that are measuring oxygenation levels of a compartment of interest.

Figure 1:
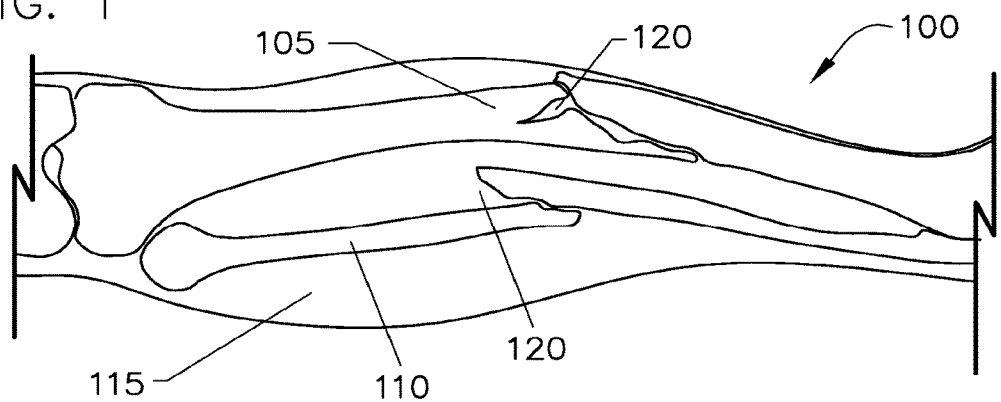
FIG. 1 illustrates an X-ray view of a human leg with fractured bones of the tibia and fibula that lead to one or more compartment syndromes in muscles surrounding the bones of the human leg.
Figure 2:
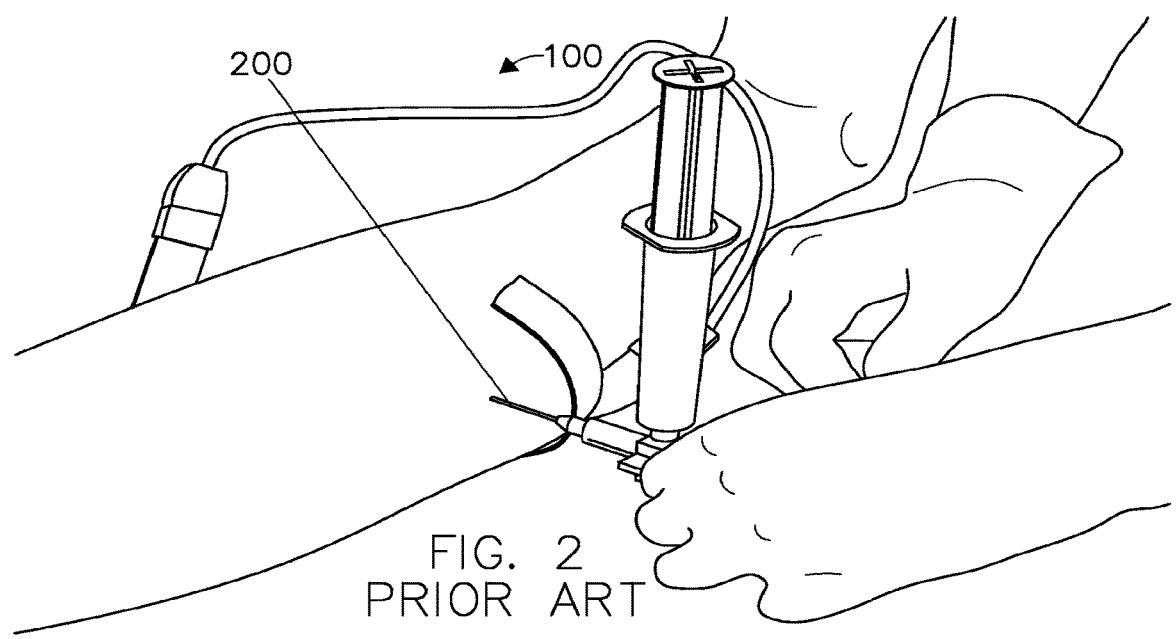
FIG. 2 is a side view of a human leg in which compartment pressures are being measured with a large bore needle according to a conventional method known in the prior art.
Figure 3:
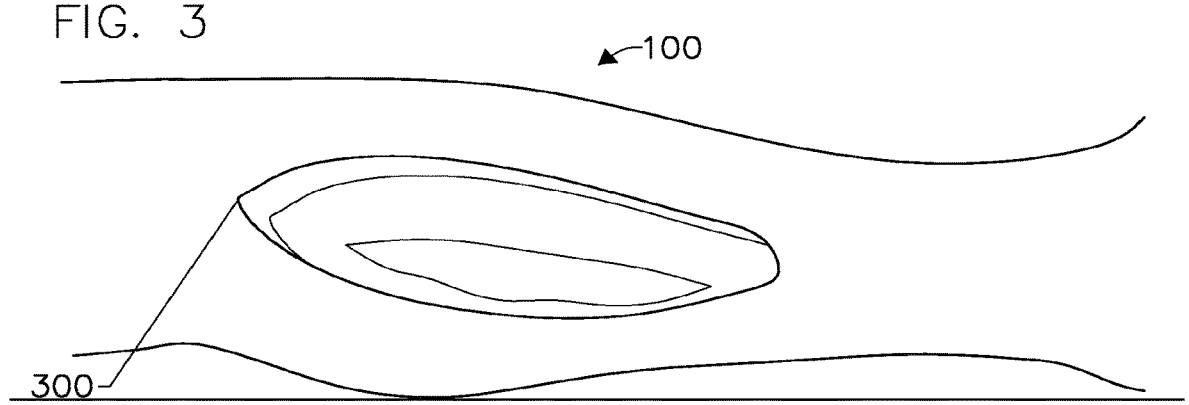
FIG. 3 is a side view of a human leg in which a surgical procedure, known as a fasciotomy, was performed in order to release the pressures in one or more compartments surrounding the bones of the leg according to a technique known in the art.
Figure 4:
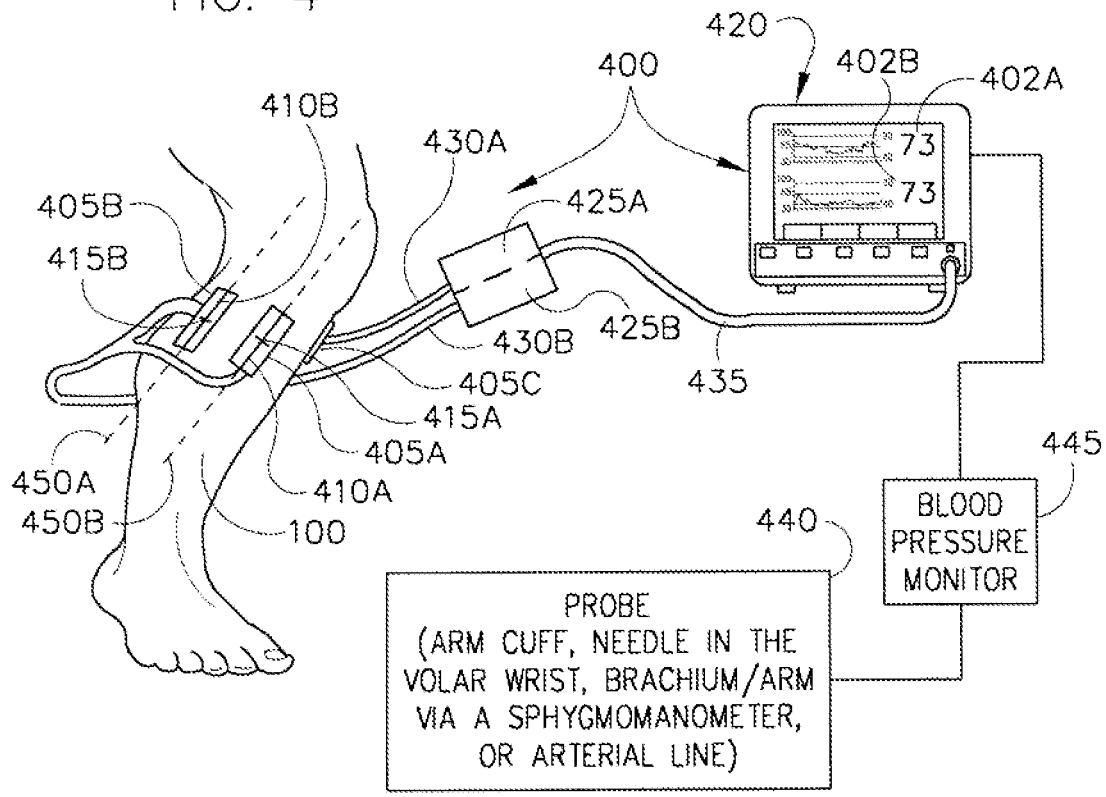
FIG. 4 illustrates oxygen levels of compartments of a human leg being measured by compartment sensors that include compartment alignment mechanisms and central scan depth markers according to one exemplary embodiment of the invention.

Referring now to the drawings, in which like reference numerals designate like elements, FIG. 4 illustrates oxygen levels 402A, 402B of compartments of a human leg 100 being measured by a near-infrared spectroscopy (NIRS) sensors 405A, 405B that include a compartment alignment mechanisms 410A, 410B and central scan depth markers 415A, 415B according to one exemplary embodiment of the invention.

The alignment mechanism 410 of a compartment sensor 405 can include a linear marking on a surface of the compartment sensor 405 that is opposite to the side which produces a light scan used to detect oxygenation levels. The linear marking can be used by a medical practitioner to align a compartment sensor 405 with the longitudinal axis 450 of a compartment of interest. The invention is not limited to a solid line on the sensor 405. Other alignment mechanisms 410 within the scope of the invention include, but are not limited to, tick marks, dashed lines, notches cut in the substrate of the compartment sensor 405 to provide a geometric reference for the medical practitioner, and other like visual orienting alignment mechanisms 405.

The central scan depth marker 415 can include a linear marking positioned on a surface of a compartment sensor 405 that intersects the alignment mechanism 410 at a location along the alignment mechanism 410 that denotes the deepest region of a light scan produced by the compartment sensor 405. The depth of measurement can be displayed in numeric form over the central scan depth marker 415 as a guide to aid medical practitioner since scan depth can vary based on the compartment sensor's light source and receptor separation. The central scan depth marker 415 can insure that a medical practitioner properly aligns the compartment sensor 405 at a location that will measure a compartment of interest. Similar to the alignment mechanism 410 noted above, the invention is not limited to a solid line on the compartment sensor 405. Other central scan depth markers 415 within the scope of the invention include, but are not limited to, tick marks, dashed lines, notches cut in the substrate of the compartment sensor to provide a geometric reference for the medical practitioner, and other like visual orienting central depth markers 415.

Once the proper position for a compartment sensor 405 is determined by the medical practitioner with the compartment alignment mechanism 410 and the central scan depth marker 415, the medical practitioner can apply the compartment sensor 405 on the patient by using an adhesive that is already part of the compartment sensor 405.

FIG. 4 illustrates three compartment sensors 405A, 405B, and 405C of a system 400 for monitoring three different compartments of the lower human leg 100. A fourth compartment sensor 405D not illustrated can be positioned on a side of the leg not illustrated and which monitors the fourth compartment of the lower human leg 100. The compartment sensors 405 illustrated in FIG. 4 and discussed throughout this document can be of the type described in U.S. Pat. No. 6,615,065 issued in the name of Barrett et al. (the "'065 patent"), the entire contents of which are hereby incorporated by reference. The compartment sensors 405 can include those made and distributed by Somanetics, Troy, MI However, other conventional near infrared compartment sensors 405 can be used without departing from the scope and spirit of the invention.

The compartment sensors 405 can generally provide spectrophotometric in vivo monitoring of blood metabolites such as hemoglobin oxygen concentration in any type of compartment and on a continuing and substantially instantaneous basis.

The compartment sensors 405 are coupled to a processor and display unit 420 which displays the two oxygen levels 402A, 402B comprising the values of seventy-three. The processor and display unit 420 can display all four oxygen levels of four compartments of the human leg 100 when at least four compartment sensors 405 are deployed. The invention is not limited to four compartment sensor embodiments. The invention can include any number of compartment sensors for the accurate detection of conditions that may be associated with compartment syndrome. For example, another exemplary embodiment illustrated in FIG.

14C allows for eight sensor readings so that concomitant monitoring of the contralateral uninjured leg can be performed.

The processor of the display unit 420 can be a conventional central processing unit (CPU) known to one of ordinary skill in the art. It may have other components too similar to those found in a general purpose computer, such as, but not limited to, memory like RAM, ROM, EEPROM, Programming Logic Units (PLUs), firmware, and the like. Alternatively, the processor and display unit 420 can be a general purpose computer without departing from the invention.

The processor and display unit 420 can operate in a networked computer environment using logical connections to one or more other remote computers. The computers described herein may be personal computers, such as handheld computers, a server, a client such as web browser, a router, a network PC, a peer device, or a common network node. The logical connections depicted in the Figures can include additional local area networks (LANs) and a wide area networks (WANs) not shown.

The processor and display unit 420 illustrated in FIG. 4 and the remaining Figures may be coupled to a LAN through a network interface or adaptor. When used in a WAN network environment, the computers may typically include a modem or other means for establishing direct communication lines over the WAN.

In a networked environment, program modules may be stored in remote memory storage devices. It will be appreciated that the network connections shown are exemplary and other means of establishing a communications link between computers other than depicted may be used.

Moreover, those skilled in the art will appreciate that the present invention may be implemented in other computer system configurations, including other hand-held devices besides hand-held computers, multiprocessor systems, microprocessor based or programmable consumer electronics, networked personal computers, minicomputers, mainframe computers, and the like.

The invention may be practiced in a distributed computing environment where tasks may be performed by remote processing devices that are linked through a communications network. In a distributed computing environment, program modules may be located in both local and remote storage devices.

The processor and display unit 420 can comprise any general purpose computer capable of running software applications and that is portable for mobile applications or emergency applications.

The communications between the processor and display unit 420 and the sensors 405 can be wire or wireless, depending upon the application. Typical wireless links include a radio frequency type in which the processor and display unit 420 can communicate with other devices using radio frequency (RF) electromagnetic waves. Other wireless links that are not beyond the scope of the invention can include, but are not limited to, magnetic, optical, acoustic, and other similar wireless types of links.

In the exemplary embodiment illustrated in FIG. 4, the compartment sensors 405 are coupled to the processor and display unit 420 with cables 430A, 430B which can include electrical conductors for providing operating power to the light sources of the compartment sensors 405 and for carrying output signals from the detectors of the sensors 405 to the display unit 420. The cables 430 may be coupled to a quad-channel coupler, a preamplifier 425A, 425B, and an integrated, multiple conductor cable 435. Alternatively, all wires could be packaged or merged into a single unit or cord or plug (not illustrated) for insertion into the monitor for ease of management for the clinician and to prevent misplacement of wire plugs into wrong sockets.

In addition to tracking compartment oxygen levels, the processor and display unit 420 may receive data from a blood pressure monitor 445. The blood pressure monitor 445 may be coupled to a probe 440 that takes pressure readings from the patient at one or more locations, such as, but not limited to, an arm with a cuff, a needle in the volar wrist, the brachium (arm) via a sphygmomanometer, or arterial line. The probe 440 can be any one of a number of devices that can take blood pressure readings, such as, but not limited to, automated inflating pressure cuffs (sphygmomanometer), arterial lines, and the like. Similarly, other types of blood pressure monitors 445 are not beyond the scope of the invention. Further details of the relationship between blood pressure and oxygen levels in the human body will be discussed and described more fully below in connection with FIGS. 19-20.

The display and processing unit 420 can display values at any one time for all compartment sensors 405 being used. While the display and processing unit 420 only displays two oxygen levels for the embodiment illustrated in FIG. 4, the display and processing unit 420 could easily display all four values from the four compartment sensors 405 that are being used to monitor the four compartments of the lower leg 100.

Figure 5A:
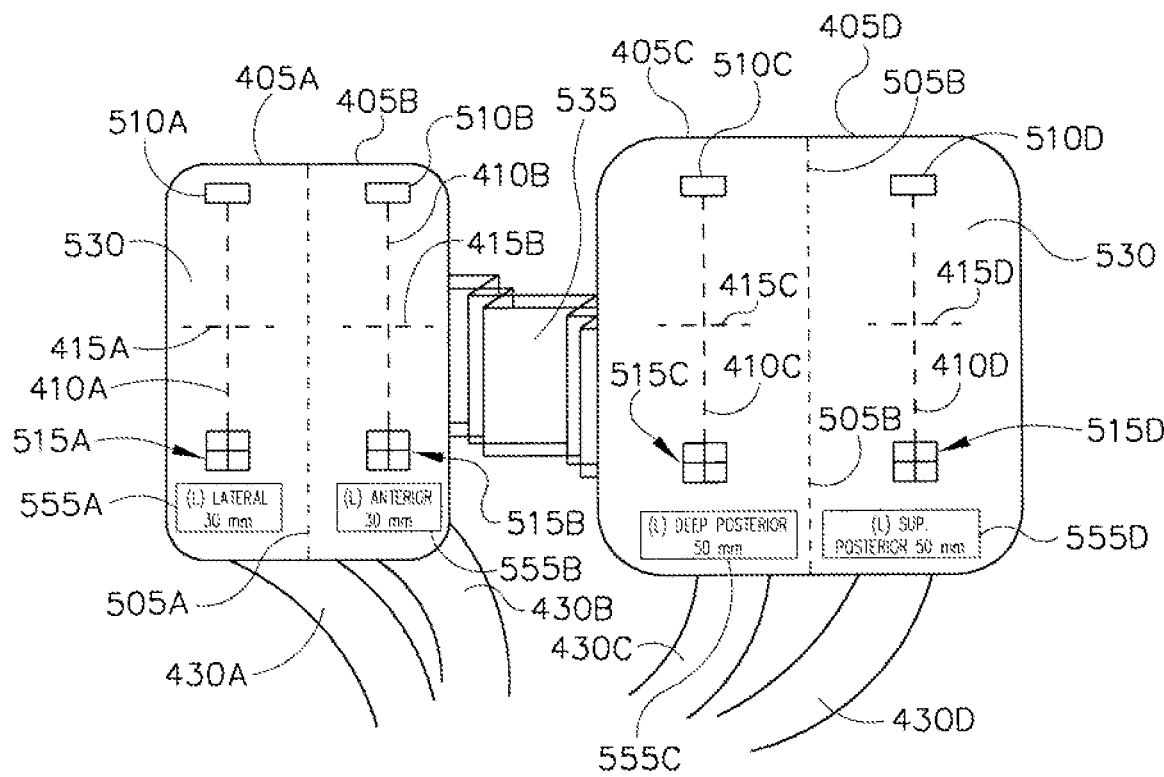
FIG. 5A illustrates a bottom view of two pairs of compartment sensors with each sensor having a compartment alignment mechanism and a central scan marker in addition to a separating device according to one exemplary embodiment of the invention.

Referring now to FIG. 5A, this figure illustrates a bottom view of two pairs of compartment sensors 405 with each sensor 405 having a compartment alignment mechanism 410 and a central scan marker 415 in addition to a separating device 505 according to one exemplary embodiment of the invention. The substrate 530 of each compartment sensor 405 can comprise a foam or plastic material that may have a soft and comfortable outer layer. The separating device 505 is illustrated with a dashed line in FIG. 5A.

According to one exemplary embodiment the separating device 505 can comprise a perforation in the substrate 530. A perforation is a series of cuts or removed portions positioned along a line which can be perforated or separated. This means, for the exemplary embodiment illustrated in FIG. 5A, the first compartment sensor 405A can be physically separated from the second compartment sensor 405B. The separating device 505 is not limited to perforations and it can include other types of devices. For example, the separating device 505 can comprise a zipper, a plastic seal line, hook and loop fasteners and other like devices that would permit the rapid and accurate expansion of compartment sensors 405 when used in a trauma setting.

As noted above, the compartment sensors 405 can include alignment mechanisms 410 and a central scan depth marker 415 in order to accurately position the compartment sensors 405 over compartments of interest. The alignment mechanisms 410 and central depth markers 415 are illustrated with dashed or dotted lines because they are "hidden" relative to the bottom view of the compartment sensors 405 which are illustrated in FIG. 5A.

Each compartment sensor 405 may comprise an optical transmitter 510 and an optical receiver 515. The optical transmitter 510 may comprise an electrically actuated light source for emitting a selected examination spectra. Specifically, the optical transmitter 510 may comprise two or more narrow-bandwidth LEDs whose center output wavelengths correspond to the selected examination spectra. Each optical receiver 515 may comprise two or more light detectors, such as photodiodes. In the embodiment illustrated in FIG. 5A, the optical receiver 515 has a total of four photodiodes in which pairs of photodiodes work together to provide a "near" detector and a "far" detector. Each photo diode must have two receptors to receive light at two separate wavelengths to allow for calculations of oxy-hemoglobin and deoxy-hemoglobin concentrations. Using two pairs of receptors allows for a deep and shallow set to enable isolation of only the deep tissue oxygenation (see FIG. 7).

Figure 7:
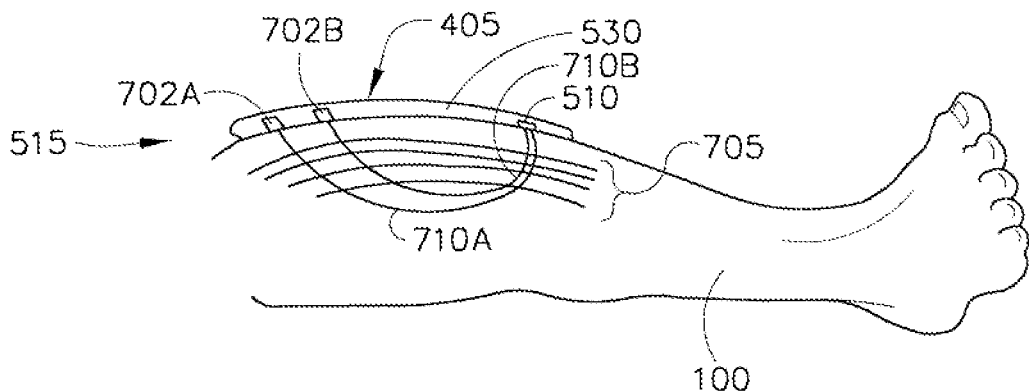
FIG. 7 illustrates a near light detector and a far light detector that are positioned within substrate material at predetermined distances from the optical transmitter of a compartment sensor according to one exemplary embodiment of the invention.

Referring briefly now to FIG. 7, the "near" light detector 702B and the "far" light detector 702A are positioned within the substrate material 530 at predetermined distances from the optical transmitter 510. The "near" detector 702B formed by the two photodiodes that are closest to the optical transmitter 510 have a light mean path length 710B which is primarily confined to "shallow" layers 705 of a compartment of interest. Meanwhile, the "far" detector 702A formed by the pair of photodiodes that are farthest from the optical transmitter 510 have a light mean path 710A that is longer than that of the "near" detector and is primarily confined to "deep" layers of a compartment of interest in a leg 100.

By appropriately differentiating the information from the "near" or "shallow" detector 702B (which may produce a first data set) from the "far" or "deep" detector 702A (which may produce a second data set), a resultant value for the tissue optical density may be obtained that characterizes the conditions within a compartment of interest without the effects that are attributable to the overlying tissue 705 which is adjacent to the compartment of interest.

This enables the compartment monitoring system 400 (illustrated in FIG. 4) to obtain metabolic information on a selective basis for particular regions within the patient and by spectral analysis of the metabolic information and by using appropriate extinction coefficients, a numerical value or relative quantified value such as 402 of FIG. 4 may be obtained which can characterize metabolites or other metabolite data, such as the hemoglobin oxygen saturation, within the particular region of interest. This region of interest is defined by the curved light mean path 710A extending from the optical transmitter 510 to the "far" or "deep" detector 702A and between this path 710A and the outer periphery of the patient but excluding the region or zone defined by the curved light mean path 710B extending from the optical transmitter 510 to the "near" or "shallow" detector 26. Further details of the compartment sensors 405 are described in U.S. Pat. No. 6,615,065, issued in the name of Barrett et al., which is hereby incorporated by reference.

Referring back now to FIG. 5A, each compartment sensor 405 has its own cable 430 that provides power to the optical transmitter 405A and that receives data from the optical receiver 515. Each compartment sensor 405 may also include a label 555 which may comprise a name and an anatomical location to position the compartment sensor 405 on a patient. This label may be placed on the bottom of the sensor 405 that contacts the patient as well as on the side that is opposite to the side which contacts the patient. For example, the first sensor 405A can have a first label 555A that comprises the phrase, "Lateral" to describe the name of the compartment that this compartment sensor 405A that is designed to assess. The numerical depth can also be displayed on the label, but is not limited to a single depth.

The first pair of compartment sensors 405A, 405B may be coupled to the second pair of compartment sensors 405C, 405D with an expansion device 535. The expansion device 535 may comprise an elastic material that stretches. The expansion device 535 allows the pair of compartment sensors 405 to be positioned on appropriate parts of a patient to monitor any compartments of interest. The four compartment sensor exemplary embodiment illustrated in FIG. 5A is designed for the four compartments of a human lower leg 100.

The expansion device 435 is not limited to elastic material. The expansion device can include other mechanisms which allow for an adjustable separation between the pairs of compartment sensors 405 so that the compartment sensors 405 may be precisely and appropriately positioned over specific compartments of interest. The expansion device 435 may include, but is not limited to, springs, tape, hook and loop fasteners, gauze, and other like materials.

Figure 5B:
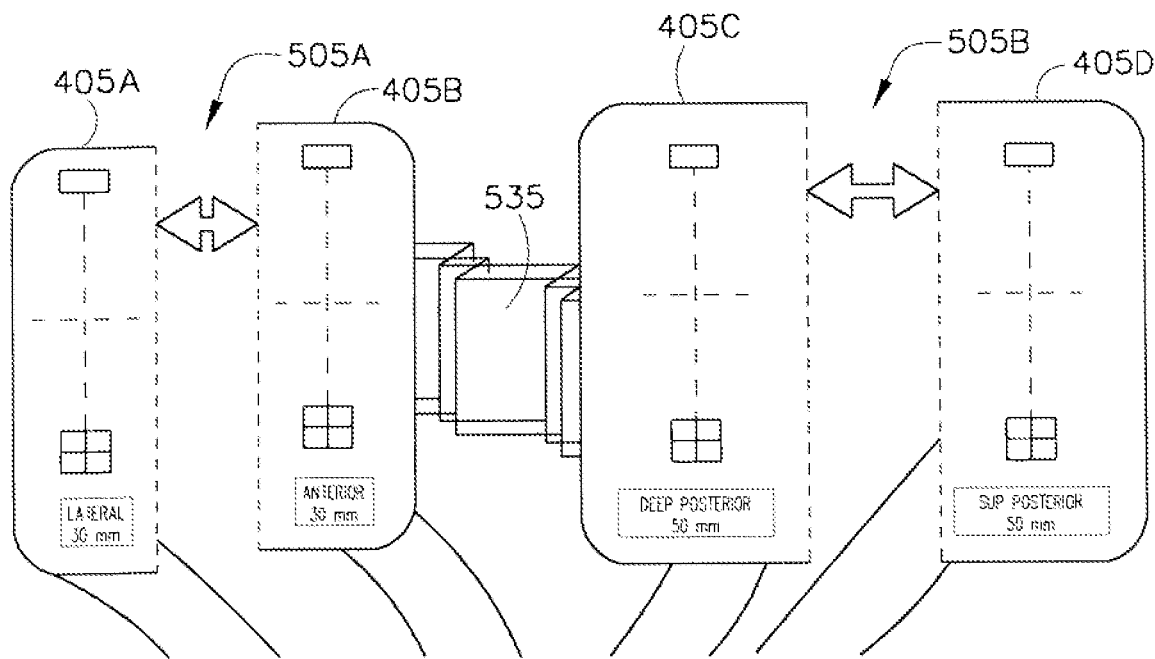
FIG. 5B illustrates a bottom view of the four compartment sensors of FIG. 5A but with the individual sensors divided from one another through using the separating device, such as the perforations, according to one exemplary embodiment of the invention.

Referring now to FIG. 5B, this figure illustrates a bottom view of the four compartment sensors 405 of FIG. 5A but with the individual sensors 405 divided from one another through using the separating device 505, such as the perforations, according to one exemplary embodiment of the invention. Specifically, the first compartment sensor 405A of the first pair of sensors 405A, 405B is physically located away from the second compartment sensor 405B. Similarly, the third compartment sensor 405C of the second pair of sensors 405B, 405C is physically located away from the fourth compartment sensor 405C. The separating device 505, the expansion device 535 in combination with the alignment mechanism 410 and central scan depth marker 415 can allow the compartment sensors 405 to be accurately and precisely positioned over compartments of interest, such as the four compartments of a human leg 100. In order to accurately monitor the appropriate compartment, a right and left configuration can be provided since compartment alignment would be reversed based on which leg is examined by the medical practitioner. Each configuration would be labeled as right or left. The configuration illustrated in FIGS. 5A and 5B are designed for human left leg 100 where the expansion device would be positioned over the tibia.

Figure 6A:
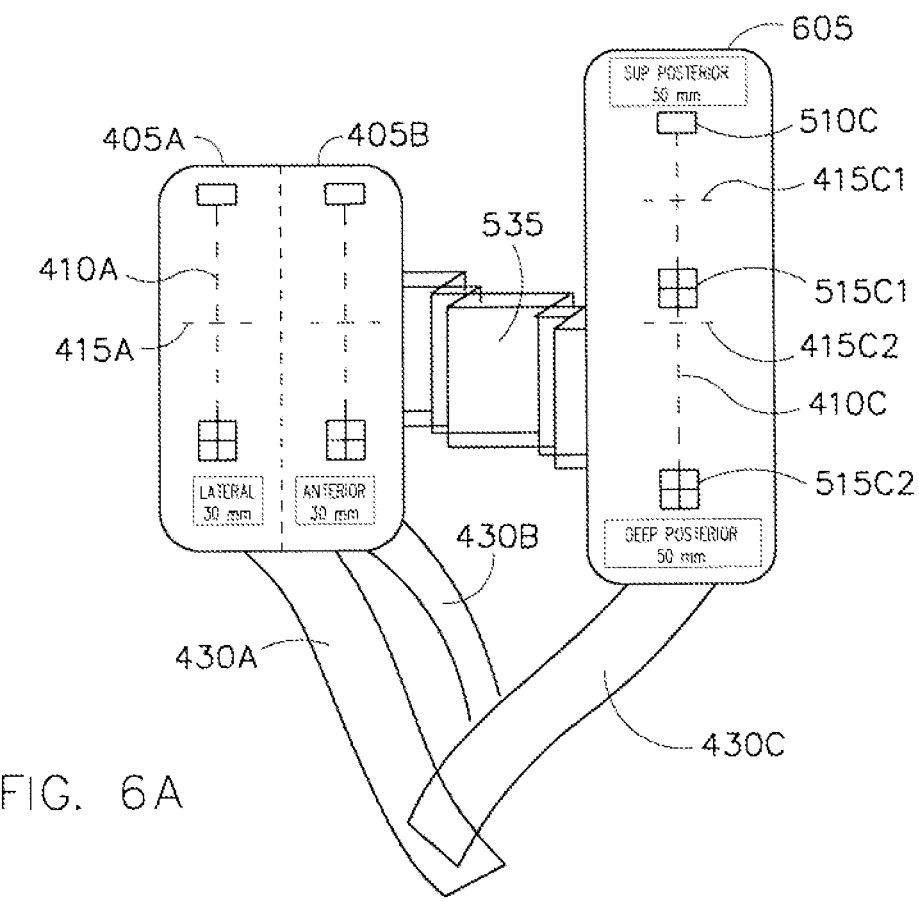
FIG. 6A illustrates a bottom view of a three sensor embodiment in which one sensor of the three compartment sensors can scan at two or more depths according to one exemplary embodiment of the invention.

Referring now to FIG. 6A, this figure illustrates a bottom view of a three sensor embodiment in which one sensor 605 of the three compartment sensors 405A, 405B, 605 can scan at two or more depths according to one exemplary embodiment of the invention. Specifically, a compartment sensor 605 may include an optical transmitter 510C that works with at least two different optical receivers 515C1 and 515C2. As noted above, each optical receiver 515 may comprise two or more light detectors, such as photodiodes. In the embodiment illustrated in FIG. 6A, each optical receiver 515C1 and 515C2 has a total of four photodiodes in which pairs of photodiodes work together to provide "near" detector and "far" detectors for a respective receiver 515C1, 515C2. This combination allows the compartment sensor 605 to scan at least two different depths. And because of the capability to scan at two different depths, the compartment sensor 605 is provided with two different central scan depth markers 415C1, 415C2.

Figure 6B:
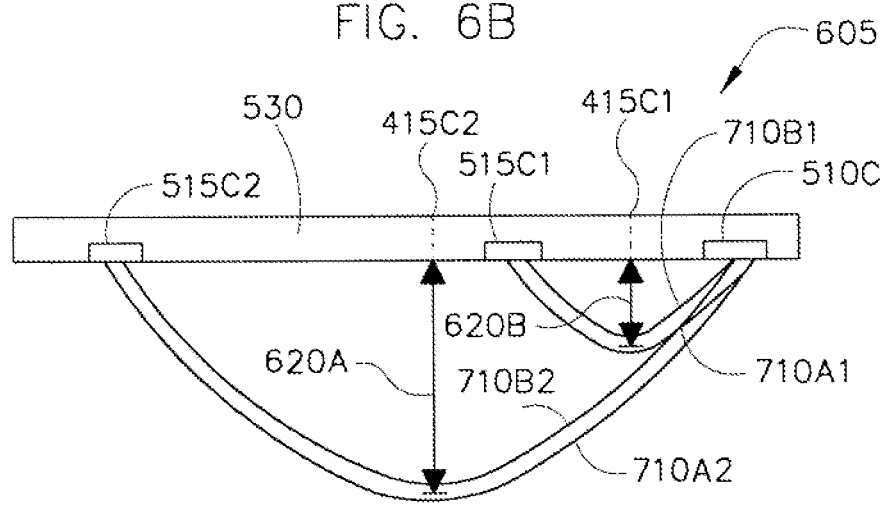
FIG. 6B, this figure illustrates the compartment sensor of FIG. 6A that can scan at two or more depths in order to measure deeper compartments of an animal body according to one exemplary embodiment of the invention.

Referring now to FIG. 6B, this figure illustrates the compartment sensor 605 of FIG. 6A that can scan at two or more depths in order to measure deeper compartments of an animal body according to one exemplary embodiment of the invention. The twp optical receivers 515 of FIG. 6B work in principal in an identical manner relative to the optical receiver described in connection with FIG. 7 discussed above. This means that the combination of the optical transmitter 510C and optical receiver 515C1 can provide an oxygenation level for a first scan depth 620B of a patient. Meanwhile, the combination of the optical transmitter 510C and the optical receiver 515C2 can provide an oxygenation level for a second scan depth 620A of a patient.

Therefore, this stacked compartment sensor 605 can be used to measure the oxygenation level of a first compartment that maybe positioned underneath a second compartment, such as for the deep posterior compartment of a lower leg 100 of a human body which is positioned beneath the superficial posterior compartment of the leg 100. This stacked compartment sensor 605 can allow the display and processing unit 420 to subtract the oxygenation level found at the first scan depth 620B of the first compartment, such as the superficial posterior compartment, from the oxygenation level at the second scan depth 620A of the second compartment, such as the deep posterior compartment.

The invention is not limited to the two stacked optical receiver embodiment 605 illustrated FIGS. 6A and 6B, and can include any number of optical receivers 515 positioned in the substrate material 530 so that various scan depths can be made to determine oxygenation levels within multiple compartments that may be stacked on or positioned adjacent to one another in a sequential or layered, shallow to deep arrangement.

Figure 6C:
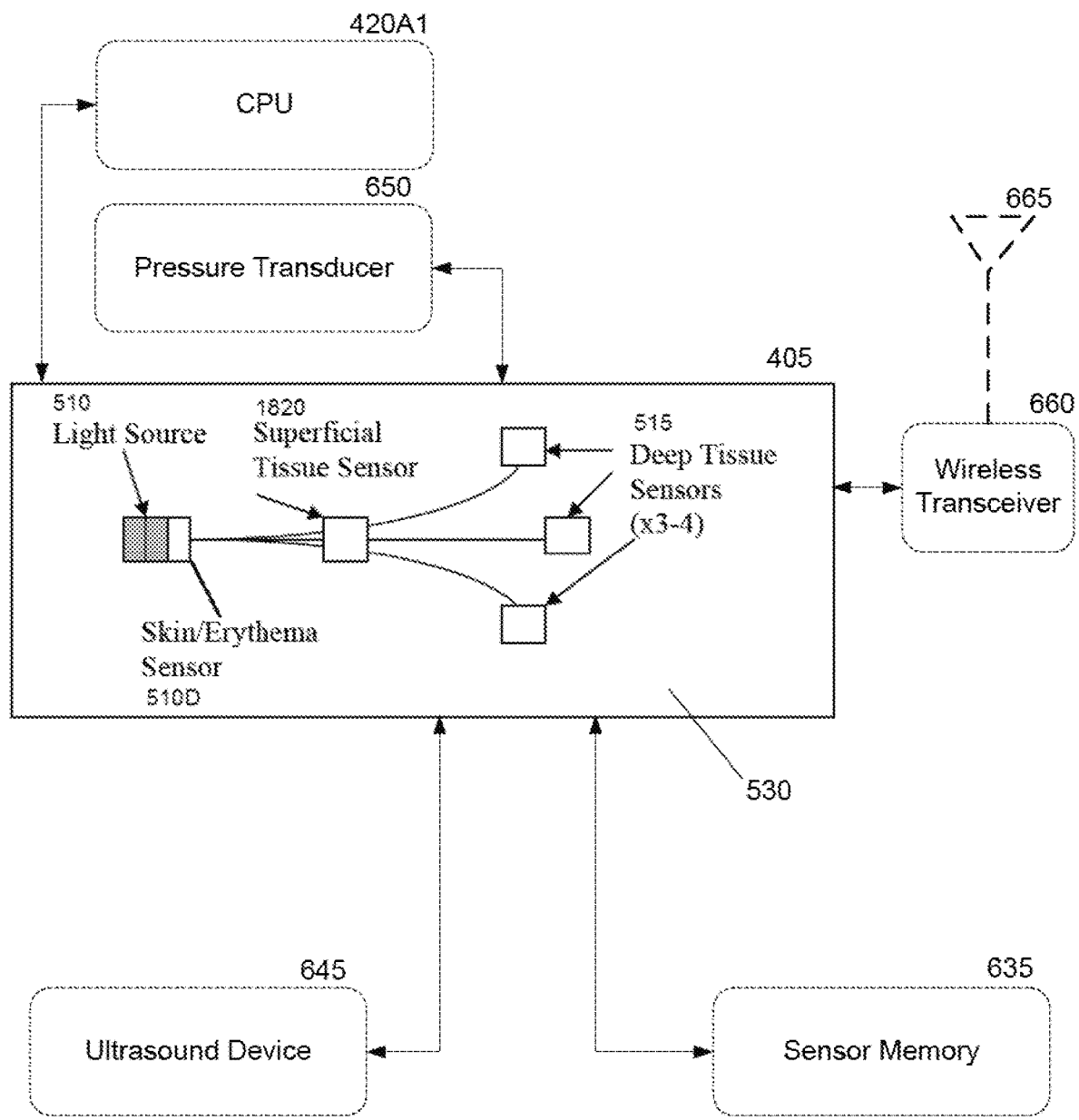
FIG. 6C illustrates a bottom view of a sensor comprising a substrate, a light source, and optical receivers according to one exemplary embodiment of the invention.

Referring now to FIG. 6C, this figure illustrates a bottom view of a sensor 405 comprising a substrate 530, a light source 510, and optical receivers 515, similar to those described above according to one exemplary embodiment of the invention. The sensor 405 also has a superficial tissue sensor or skin sensor 1820. Further details of the skin sensor will be described below in connection with FIG. 18. The light source 510 and the optical receivers 515 can be controlled over time (and may be referred to in the art as time related reflectance) to adjust for the reflectivity and penetration depth of optical light which leaves the light source 510 and enters layers of skin 1805 (See FIG. 18). The optical receivers 515 can be controlled so that they are instructed to wait for measuring optical light that has penetrated deeper into the skin 1805 and other tissue layers. The light reflectance can be used to measure depth of fat subcutaneously in order to allow for different size people. For example, this light reflectance can be used and scaled for people with various thicknesses in skin and fat tissue.

Three to four or more receivers 515 can be positioned in an arch around the same light source 510 at between about thirty and about forty-five degrees or more. One of ordinary skill in the art recognizes that any number of receivers 515 and light sources can be employed at various different positions without departing from the scope of the invention.

In other exemplary embodiments (not illustrated), the receivers 515 can be positioned in a circle or at about 360 degrees around the single light source 510. Each of the optical receivers 515 can be independently or separately controlled.

The optical receivers 515 and/or the skin sensor 1820 can be used to measure any initial reflectance over a short time period such that skin pigment and erythema can be assessed. Erythema is a condition of skin and tissue after they have been injured. Usually, with this condition, fair or white pigmented skin individuals usually have red colored, swollen skin near tissue in an Erythematic condition. If the light source 510 uses red colored light to assess red colored skin then false readings may occur in this situation. Therefore, the light source 510 can be provided with a skin sensor 510D that is used under Erythema conditions. Additional wavelengths can be added to the light source 510 outside of the near infrared range in order to determine a measure of erythema of the subcutaneous skin. By using wavelengths in the red and green spectrum, an algorithm can be formulated to measure erythema (A dermaspectrum II was used by the inventor in a study in which the inventor looked at pigment using green & red light to measure erythema). However, one of ordinary skill in the art recognizes that other colors or optical wavelengths, above or below the green colored spectrum, can be produced by the skin sensor 510D without departing from the invention.

The skin sensor 510 can scan at exemplary depths of about between four and seven millimeters. However, other depths higher or lower than those specifically described are not beyond the scope of the invention.

The skin sensor 510D can be calibrated to measure both a pigmentation index as well as an erythema index. The pigmentation index would be incorporated in all measurements. The erythema index would allow the sensor to determine if the tissue being measured was traumatized or not. Different calibrations could be used in different circumstances. If the tissue 1805 being measured is traumatized, the erythema index would be elevated and a hyperemic effect would be expected. If the erythema index is elevated and hyperemia is not present an alarm would be triggered for concern about poor perfusion. Control, uninjured tissues could be recognized by lower erythema indices. The following are indices that can be used by the dermaspectrometer for measuring pigment (red light only) and erythema (red & green light):

Melanin index (100 log 1/ired)
Erythema index (100 log ired/igreen)

If the skin layer 1805 is missing, then the skin sensor 510D can be shut off while the light source 510 continues to illuminate a tissue area of interest. This ability will be important in traumatized tissue or wounds since in many cases trauma results in loss of skin. When skin is missing the superficial recording will be turned off in order to account for lack of pigmentation and erythema. A separate calibration will be used in these cases where measurements are taken directly over tissue which does not have skin, such as over muscle.

Additionally, a sterile sensor 405 with a sufficiently long sterilized cord will be required to allow for sterile technique to be maintained in an operating room setting. According to one exemplary embodiment, the light source 510 can be provided with at least two different light sources 510 that illuminate in different optical wavelengths, such as in the wavelengths for the color red and green. In this embodiment, these two different light sources can be used to detect an erythema condition in which the skin layers 1805 may be red in color.

The sensor 405 can be designed to account for different thickness or level of fat layers present in a particular patient. Sensors 405 can be sized to measure different sized individuals. For example based on the circumference of a leg, or extremity/body part, different size devices can be fabricated with different depths of tissue monitoring (spread of light source and sensor) in order to maximize the tissue sampling in a correct location. A large, medium and small size can be designed to read tissues customized to different anatomic variations in different sized people. An ultrasound device 645 can be incorporated into the sensor 405 for monitoring and for determining fat depth. The ultrasound device 645 and other devices in FIG. 6C are illustrated with dashed lines to indicate that such hardware/software may be optional for the sensor 405. Also, any combinations of this hardware/software can be included in the sensor 405 without departing from the invention.

A pressure transducer 650 can be incorporated into the sensor 405 in order to determine if the dressings for a wound have been applied too tight. Additionally, in trauma settings, dressings are applied initially and swelling continues after the dressing application. If a pressure transducer 650 determines increasing pressure on the tissue 1805 from external forces (dressings, splints, casts), an alarm can sound to warn the clinician. If external pressures increase while and oxygenation values decrease, then the alarm will sound to release the dressing or loosen the restrictive dressing.

The sensors 405 can be used to take multiple readings of similar areas of interest. Subcutaneous vessels can cause erroneous values. Subcutaneous vessel effects can be removed if single sensor 405 is aberrant. Additionally, in traumatized tissue, readings can be difficult to obtain due to hematomas (collections of blood). Each sensor 405 may also account for small vessel abnormalities. A weighted average of values from the scans can be taken which should yield better sampling of tissue that is of interest. It should also allow for higher ability of obtaining a reading and maintaining a reading after placement since hematomas would have to block multiple sensors to lose a signal completely. Abnormally high or low values (deviated by a predetermined value such as ten or more percentage points) can be thrown out.

The sensor 405 may further comprise a memory device 635. The memory device 635 may comprise volatile or non-volatile memory or a combination of both. The memory device 635 can comprise any type of machine readable medium. Any machine readable medium can include, but is not limited to, floppy diskettes, optical disks, CD ROMs, magneto optical disk ROMs, RAMs, EPROMs, EEPROMs, magnetic or optical cards, flash memory, or any other type of media/machine readable medium suitable for storing records and/or electronic instructions for a CPU 420A1. The CPU 420A1 can run or execute programs for activating the various components of the sensor 405 to take readings and storing them in the memory device 635. Alternatively, the CPU 420A1 may comprise firmware and/or hardwired circuitry without departing from the scope of the invention.

The CPU 420A1 may also be coupled to a wireless transceiver 660 that uses an antenna 665. The wireless transceiver 660 can employ any one of a number of wireless media such as radio-frequency communications, optical communications, magnetic/inductive communications, acoustic communications, and other like wireless media, as described above in connection with FIG. 4. The wireless transceiver 660 can relay the data produced and recorded by the sensor 405 to a remote monitoring apparatus, such as a monitor 420. Additionally, the data could be sent via satellite or other means to a central monitoring station or even a clinicians phone, pager or other mobile device for distance monitoring or access.

In this way, the sensor 405 may become a portable unit that can be used by the patient and/or monitored by a medical practitioner located at a distance from the patient. With the memory device 635, continuous data can be stored on the sensor 405 without a need to record on a central device such as a processor and display unit 420. This ability to record data on the sensor 405 will allow a sensor to couple with different, remote monitors 420 to allow continual data collection and display of the data. This feature will allow for interchangeability between sensors 405 and remote monitors 420, irrespective of their manufacturer. The data stored in the memory device 635 may be provided with time stamps so that the data can be mapped over time.

Additionally, interchangeability between different sensors 405 for different functions (such as a leg sensor 405 or an arm sensor 405 or a cerebral sensor 405 and a tissue transfer sensor 405) would be recognized by the system 1900 and a set series of alarms or readings would be recorded based on the sensor 405 inserted into the monitor 420 or coupled to the monitor 420 in a wireless manner. Therefore, the same monitor 420 would be able to identify the type of sensor 405 couple to the monitor 429. A single monitor 420 could be compatible with multiple different sensors 405 and display appropriate data and alarms based on the sensor 405 collecting data about the tissue/areas of interest.

The memory device 635 may have a significant amount of capacity and it may allow for notes to be added to patient history. In addition to the reflectance values recorded by the optical receivers 515, the memory device 635 may be able to store other measured parameters taken by other sensors and/or tests. For example, the memory device 635 may also store a patient's blood pressure, temperature, respiratory status (rate, supplemental oxygenation, pulse oximetry values, etc.) over time. Further, any lab work such as lactic acid levels, CBC count, and blood chemistry may be provided and stored in memory device 635.

The sensor 405 can be incorporated into a wound dressing in order to monitor physiological conditions during transportation of injured subjects. This capability would be built into a dressing that can be attached to vacuum devices for management of extremity wound with gross contamination or skin loss.

Figure 8A:
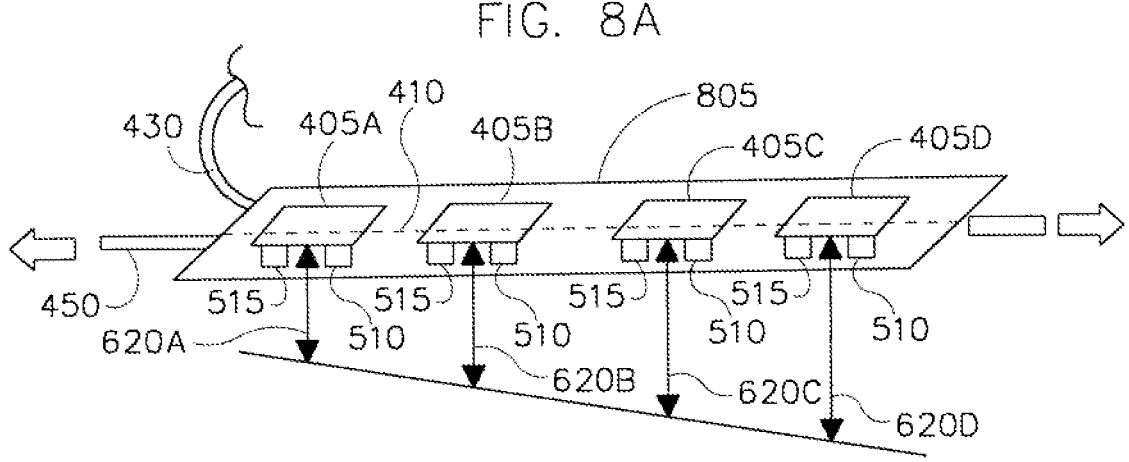
FIG. 8A illustrates a linear array of compartment sensors assembled as a single mechanical unit that can provide scans at various depths according to one exemplary embodiment of the invention.

Referring now to FIG. 8A, this Figure illustrates a linear array 805 of compartment sensors 405 assembled as a single mechanical unit that can provide scans at various depths 620A, 620B, 620C, and 620D. The compartment sensors 405 can be simultaneously activated to produce their scans of various depths 620 at the same time when optical filters are used as will be described more fully below in connection with FIG. 8C. Alternatively, the sensors 405 of the linear array 805 can produce their scans of various depths 620 by controlling a phase or timing of the activation of the sensors 405 so that no two sensors 405 are activated at the same time in order to reduce any potential of optical interference between the sensors 405. This phasing of the sensors can be controlled by the display and control unit 420 of FIG. 4.

The first compartment sensor 405A can provide a first scan depth 620A that is shorter or more shallow than a second scan depth 620B produced by the second compartment sensor 405B. The scan depths 620 can increase in this manner along its longitudinal axis which corresponds with its alignment mechanism 410 so that the linear array 805 matches the one or more depths of a single compartment of interest. As noted above in connection with FIG. 6B, the scan depth 620 of a compartment sensor 405 is function of the separation distance between the optical transmitter 510 and optical receiver 515. For example, a scan depth 620 of a compartment sensor 405 can be decreased as the optical receiver 515 is moved closer along the body of the sensor 405 towards the optical transmitter 510C.

One of ordinary skill in the art recognizes that many of the compartments of the human body have various different geometries and resulting depths relative to the outside skin of a patient. For example, the compartments of the lower human leg 100 tend to have a greater depth or volume adjacent to the knee and generally taper or decrease in depth towards the ankle or foot. Therefore, linear arrays 805 of compartment sensors 405 can be designed to have depths that match a particular geometry of a compartment of interest. To achieve these different scan depths 620, each compartment sensor 405 can have an optical transmitter 510 and an optical receiver 515 that is spaced or separated from each other by an appropriate distance to achieve the desired scan depth 620. If a compartment of interest has a substantially "flat" or "linear" depth relative to the skin surface of a patient, the linear array 805 can be designed such that each compartment sensor 405 produces scans with uniform depths (not illustrated) to match a compartment with such a linear or flat geometry.

Like the single sensor embodiments described above in FIGS. 4-6A which are designed to measure individual compartments, the compartment sensor array 805 may comprise an alignment mechanism 410 that can be positioned so that it corresponds with the longitudinal axis 450 of a particular compartment. The compartment sensor array 805 of FIG. 8A is not provided with any central depth markers 415 like those of the single sensor embodiments since the depth markers 415 may not be needed by the medical practitioner since he or she will be assessing the entire length of a particular compartment with the entire compartment sensor array 805 which is unlike that of the single sensor embodiments. Alternatively, multiple crosshatches and numerical depths (not illustrated) can be positioned over each light source/receptor set to locate where each measurement is obtained for identifying sites of a hematoma, which will be described in more detail in connection with FIGS. 15-16 below. Additionally, these positions could be used to locate appropriate amputation level for diabetics or peripheral vascular disease, which is also described in more detail in connection with FIGS. 15-16 below.

Referring now to FIG. 8B, this figure illustrates a linear compartment sensor array 805 that can include optical transmitters 510 that are shared among pairs of light receptors 515. For example, a single optical transmitter 510A1 can produce light rays 820A, 820B that can be used by two optical receivers 515A1, 515A2 that are disposed at angles of one-hundred eighty degrees relative to each other and the optical transmitter 510A1 along the longitudinal axis and alignment mechanism 410A of the compartment sensor array 805A. As described previously, the light source and receptor separation can be varied to best match the topography of the compartment in the leg or other body part. Larger separation would allow for deeper sampling in the proximal leg versus more shallow depth closer to the ankle.

As discussed above in connection with the single sensor array 805 of FIG. 8A, the sensors 405 of each compartment sensor array 805 illustrated in FIG. 8B can be simultaneously activated to produce their scans at the same time when optical filters (not illustrated in FIG. 8B) are used as will be described more fully below in connection with FIG. 8C. Alternatively, the sensors 405 of each linear compartment sensor array 805 can produce their scans by controlling a phase or timing of the activation of the sensors 405 so that no two sensors 405 are activated at the same time in order to reduce any potential for optical interference between the sensors 405. This phasing of the sensors can be controlled by the display and control unit 420 of FIG. 4.

Like the single sensor embodiment illustrated in FIG. 5A, the compartment sensor array 805 of FIG. 8B can comprise an alignment mechanism 410 for aligning the structure with the longitudinal axis 450 of a compartment as well as a separation device 505A that can be used to divide the physical structure of the paired array 805A, 805B into two separate linear compartment sensor arrays 805A, 805B. The compartment sensor arrays 805 of FIG. 8B may also include labels 555 and an expansion device 535, like those of FIG. 5A. The labels can be positioned on the front and back sides of each compartment sensor array 805. While the optical transmitters 510 and receivers 515 of FIG. 8B are illustrated in functional block form, it is noted that these elements as well as other numbered elements, which correspond to the numbered elements of FIGS. 4-7, work similar to the embodiments described and illustrated in FIGS. 4-7.

Figure 8C:
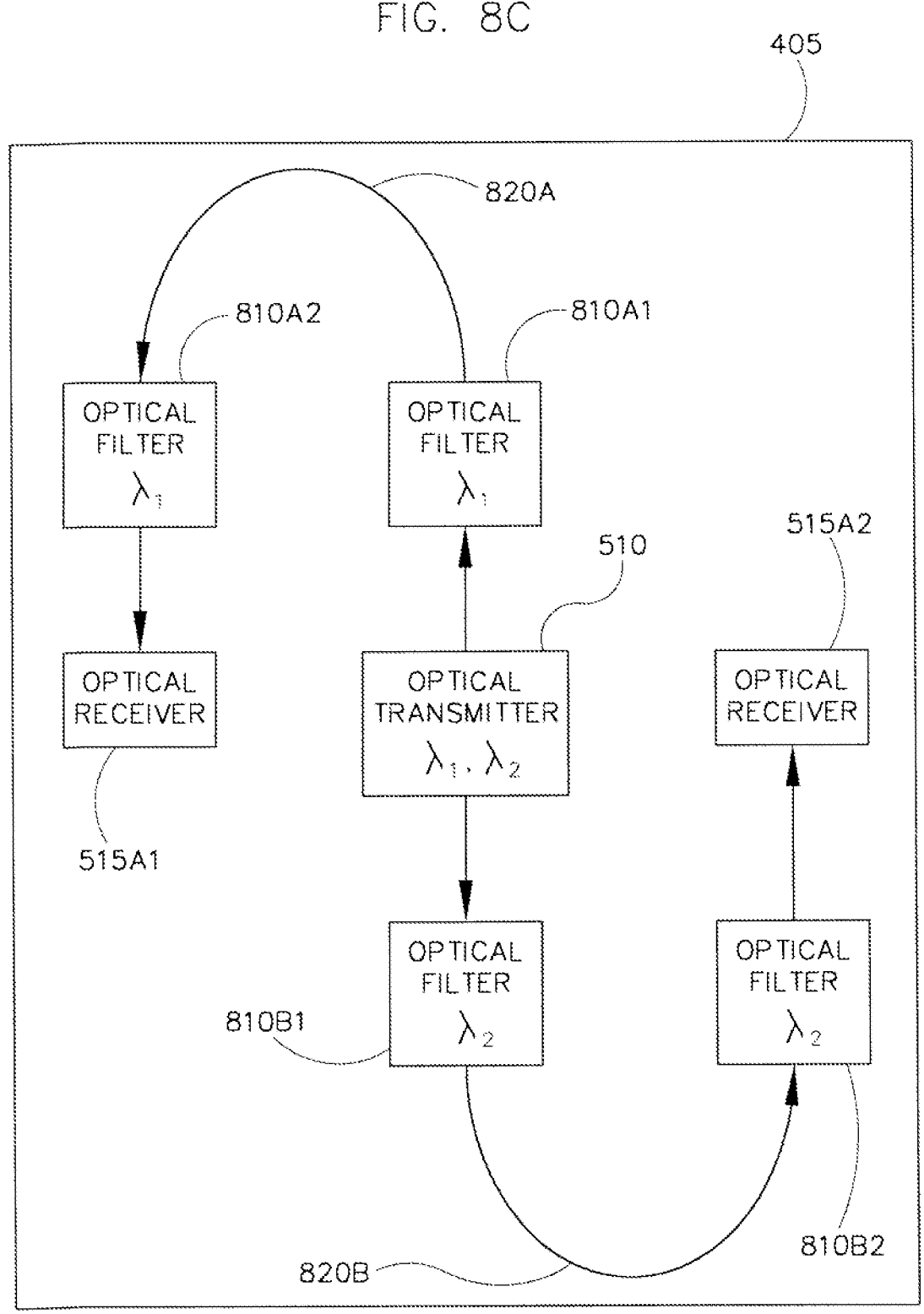
FIG. 8C is a functional block diagram of compartment sensor that illustrates multiple optical receivers that may positioned on opposite sides of a single optical transmitter and that may be simultaneously activated to produce their scans at the same time according to one exemplary embodiment of the invention.

Referring now to FIG. 8C, this figure is a functional block diagram of compartment sensor 405 that illustrates multiple optical receivers 515 that may positioned on opposite sides of a single optical transmitter 510 and that may be simultaneously activated to produce their scans at the same time. This exemplary embodiment can produce scans at the same time by using light with different wavelengths. Using light with different wavelengths can help reduce and substantially eliminate any optical interference that can occur between multiple light rays that may be received by the multiple optical receivers 515. While the optical receivers 515 of FIG. 8C are illustrated in functional block form, it is noted that these receivers 515 as well as other numbered elements, which correspond to the elements of FIGS. 4-7, work similar to the embodiments described and illustrated in FIGS. 4-7.

The two optical receivers 515A1, 515A2 of FIG. 8C may be simultaneously activated when two optical filters 810A, 810B having different wavelengths are used. The first optical filter 810A may have a first wavelength of lambda-one ($\lambda 1$) which is different than a second wavelength of lambda-two ($\lambda 2$) that is the wavelength of the second optical filter 810B1. The optical transmitter 510 can be designed to produce light having wavelengths of the first and second wavelengths which correspond with the first and second optical filters 810A, 810B.

Light 820A with a first wavelength can be produced by the optical transmitter 510 propagating its light through a first optical filter 810A1 that is designed to only let the first wavelength pass through it. Similarly, Light 820B with a second wavelength can be produced by the optical transmitter 510 propagating its light through a second optical filter 810B1 that is designed to only let the second wavelength pass through it. A third optical filter 810A2 corresponding with the first optical filter 810A1 can be designed to only pass the first wavelength such that the optical receiver 515A1 only detects light of the first wavelength. Similarly, a fourth optical filter 810B2 corresponding with the second optical filter 810B1 can be designed to only pass the second wavelength such that the optical receiver 515A2 only detects light of the second wavelength.

In this way, simultaneous different compartment scans can be produced at the same time with light having the first wavelength of lambda-one ($\lambda 1$) and light having the second wavelength of lambda-two ($\lambda 2$), in which the two optical receivers 515A1 and 515A2 share the same optical transmitter 510. This principal of optical receivers 515 sharing the same optical transmitter 510 is also illustrated in FIG. 8B which provides the compartment sensor arrays 805 discussed above. Specifically, any optical transmitter 510/optical receiver 515 group that is positioned along a single alignment mechanism 410 and longitudinal axis 450 can be designed to have a unique wavelength relative to its neighbors along the same line. So this means that each optical transmitter 510/optical receiver 515 group of a particular compartment sensor array 805, such as first array 805A, can be designed to have unique wavelengths relative to each other for illuminating the same compartment. Meanwhile, a neighboring compartment sensor array 805, such as second array 805B, may have the same wavelength arrangement as the first array 805A.

One of ordinary skill in the art recognizes that each light optical transmitter and optical receiver design uses two separate wave lengths to solve for oxy-hemoglobin and deoxy-hemoglobin concentrations, as illustrated in FIG. 7. Therefore, the two optical wavelength design described for FIG. 8C above may translate into four or more wavelengths for each optical transmitter 510 and pair of optical receivers 515. The two wavelength design for FIG. 8C was described above for simplicity and to illustrate how groups of optical transmitters and optical receivers can operate at different wavelengths relative to the groupings.

The invention is not limited to only two optical receivers 515 that share the same optical transmitter 510. The invention could include embodiments where a single optical transmitter 510 is shared by a plurality of optical receivers 515 greater than two relative to the exemplary embodiment illustrated in FIG. 8C.

Referring now to FIG. 9A, this figure illustrates a cross-sectional view of a left-sided human leg 100 that has the four major compartments 905 which can be measured by the compartment sensors 405 according to one exemplary embodiment of the invention. A first compartment 905B (also noted with a Roman Numeral One) of the lower human leg 100 comprises the anterior compartment that is adjacent to the Tibia 910 and Fibula 915. A first compartment sensor 405B is positioned adjacent to the anterior compartment 905B and provides a first oxygenation scan having a depth of 620B.

A second compartment 905A (also noted with a Roman Numeral Two) of the lower human leg 100 comprises the lateral compartment that is adjacent to the Fibula 910. A second compartment sensor 405A is positioned adjacent to the lateral compartment 905A and provides a second oxygenation scan having a depth of 620A.

A third compartment 905D (also noted with a Roman Numeral Three) of the lower human leg 100 comprises the superficial posterior compartment that is behind the Tibia 910 and Fibula 915. A third compartment sensor 405D is positioned adjacent to the posterior compartment 905D and provides a third oxygenation scan having a depth of 620D.

A fourth compartment 905C (also noted with a Roman Numeral Four) of the lower human leg 100 comprises the deep posterior compartment that is within a central region of the human leg 100. A fourth compartment sensor 405C is positioned adjacent to the deep posterior compartment 905C and provides a fourth oxygenation scan having a depth of 620C.

Referring now to FIG. 9B, this figure illustrates a cross-sectional view of a right-sided human leg 100 and possible interference between light rays 820 of simultaneous oxygenation scans made by the compartment sensors 405 into respective compartments of interest according to one exemplary embodiment of the invention. This figure illustrates how light rays 820 produced by respective compartment sensors 405 can interfere with one another. To resolve this potential problem, the activation and hence, production of light rays 820, by the compartment sensors 405 can be phased so that light rays 820 produced by one compartment sensor 405A are not received and processed by a neighboring compartment sensor 405B, 405C. When light is emitted from the compartment sensors 405 through tissue, the light does not travel in a straight line. It is reflected and spreads throughout the whole tissue. Therefore, light interference or noise would be a significant concern for multiple light sources placed in close proximity to each other. Alternatively, and as noted above, each compartment sensor 405 can produce optical wavelengths that are independent of one another in order to reduce any chances of optical interference.

Referring now to FIG. 9C, this figure illustrates a position 930 of a compartment sensor 405C in relation to the knee 927 for the deep posterior compartment 905C of a right sided human leg 100 according to one exemplary embodiment of the invention. As illustrated in FIGS. 9A and 9B discussed above, the deep posterior compartment sensor 405C can be positioned such that the sensor 405C can directly sense the oxygenation levels of this compartment 905C without penetrating or going through another compartment. With respect to FIG. 9C, the deep posterior compartment 905C can be accessed by placing the sensor along the posteromedial aspect of the medial tibia. In other words, palpation of the shin bone will allow the location of the tibia. The sensor 405 should be placed just behind the bone on the inside of the leg along the longitudinal axis 450C of the compartment 905C (not illustrated in this Figure). The compartment sensor 405C can be aligned with the longitudinal axis 450C of the deep posterior compartment 905C through using the alignment mechanism 410C. The compartment sensor 405C can positioned at any point along the longitudinal axis 450C. The location of this deep posterior compartment sensor 405C on the lower leg 100 may be one inventive aspect of the technology since it allows a direct scan of the deep posterior compartment 905C.

Figure 10:
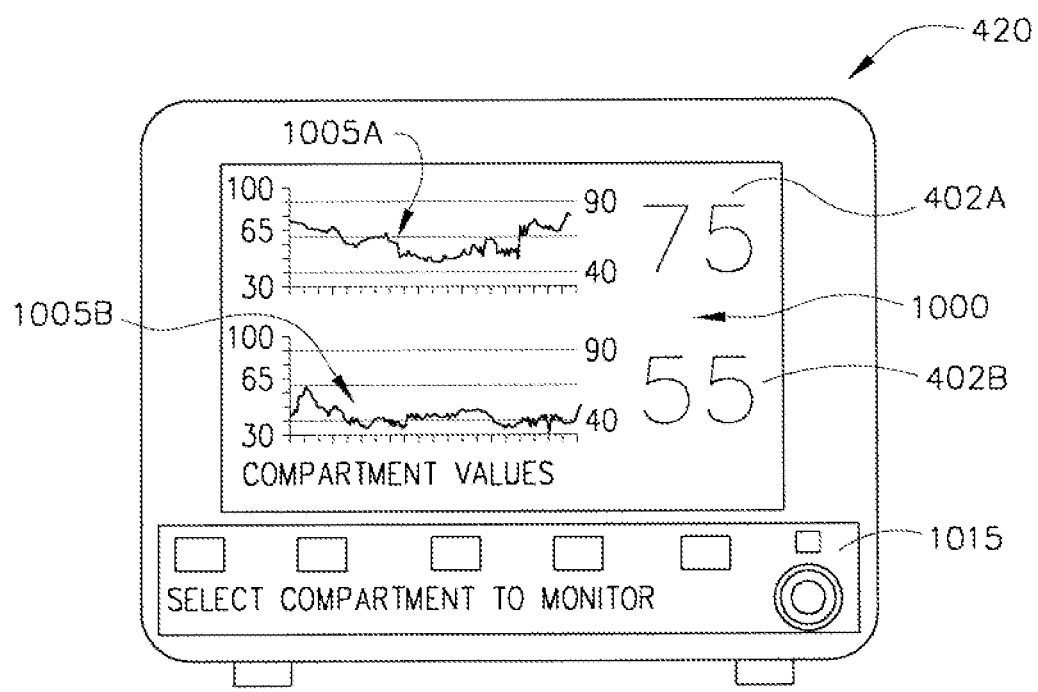
FIG. 10 illustrates an exemplary display of numeric oxygenation values as well as graphical plots for at least two compartments of an animal according to one exemplary embodiment of the invention.

Referring now to FIG. 10, this figure illustrates an exemplary display 1000 of numeric oxygenation values 402 as well as graphical plots 1005 for at least two compartments of an animal according to one exemplary embodiment of the invention. The graphical plots 1005 can display the current instantaneous oxygenation level for each compartment as a point as well as historical data displayed as other points along a line that plots the history for a particular compartment sensor 405. In other words, the X-axis of the plots 1005 can denote time in any increments while the Y-axis of the plots can denote oxygenation levels monitored by a particular sensor 405.

While only two plots are illustrated, multiple plots can be displayed for each respective sensor 405. In compartment sensor array 805 deployments, the graphical plot 1005 can represent an "average" of oxygenation levels measured by the multiple sensors of a particular linear compartment sensor array 805. The display device 420 can include controls 1015 that allow for the selection of one or more compartment sensors 405 or one or more compartment sensor arrays 805 for displaying on the display device 420. The display of historical oxygenation levels of a compartment 905 over time through the plots 1005 is a significant improvement over conventional methods of direct pressure readings of compartments 905 which usually would only allow periodic measurements of compartments 905 on the order of every fifteen or thirty minutes compared to minutes or seconds now measured with the compartment sensors 405 described in this document.

Figure 11:
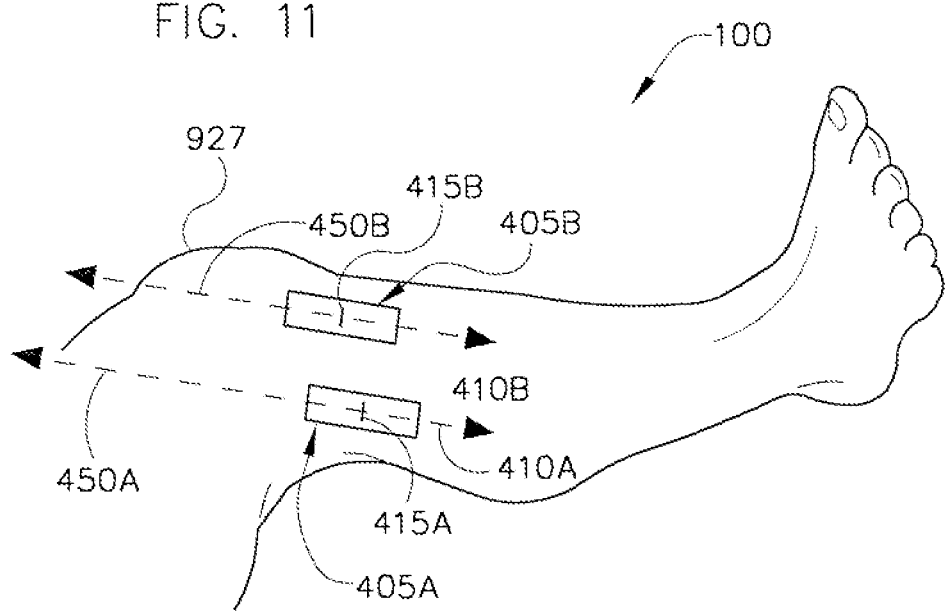
FIG. 11 illustrates single compartment sensors with alignment mechanisms and central scan depth markers that can be used to properly orient each sensor with a longitudinal axis of a compartment of an animal body according to one exemplary embodiment of the invention.

Referring now to FIG. 11, this figure illustrates single compartment sensors 405 with alignment mechanisms 410 and central scan depth markers 415 that can be used to properly orient each sensor 405 with a longitudinal axis 450 of a compartment 905 of an animal body according to one exemplary embodiment of the invention. While the longitudinal axis 450 of a compartment (shown with broken lines) cannot actually be seen on the external surface of a lower human leg 100 by a medical practitioner, a medical practitioner can envision this invisible axis 450 based on the anatomy of the leg, such as looking at the knee 927 and comparing its orientation with the ankle and foot of the leg 100. As described above, the compartment extends from the knee to ankle and the sensor can be placed over a portion or all of the compartment being measured. With these single compartment sensor 405 embodiments, each sensor 405 can be positioned along the length of the longitudinal axis 450 to obtain an oxygenation level for a particular compartment 905 of interest.

Figure 12:
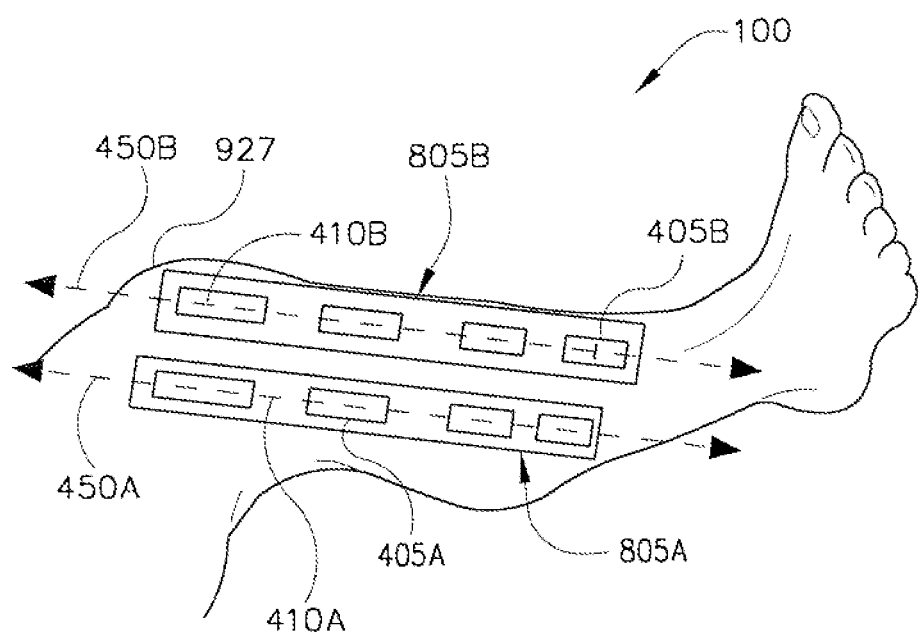
FIG. 12 illustrates compartment sensor arrays with alignment mechanisms that can be used to properly orient each array with a longitudinal axis of a compartment of an animal body according to one exemplary embodiment of the invention.

Referring now to FIG. 12, this figure illustrates compartment sensor arrays 805 with alignment mechanisms 410 that can be used to properly orient each array 805 with a longitudinal axis 450 of a compartment 905 of an animal body according to one exemplary embodiment of the invention. Since compartment sensor arrays 805 will typically occupy close to the entire length of any given longitudinal axis 450 of a compartment 905 of interest, the individual sensors 405 of the compartment sensor array 805 are usually not provided with central scan depth markers 415. In the sensor array embodiments, the arrays 805 are usually provided only with the alignment mechanism 410. However, the central scan depth markers 415 could be provided if desired for a particular application or medical practitioner (or both).

Figure 13A:
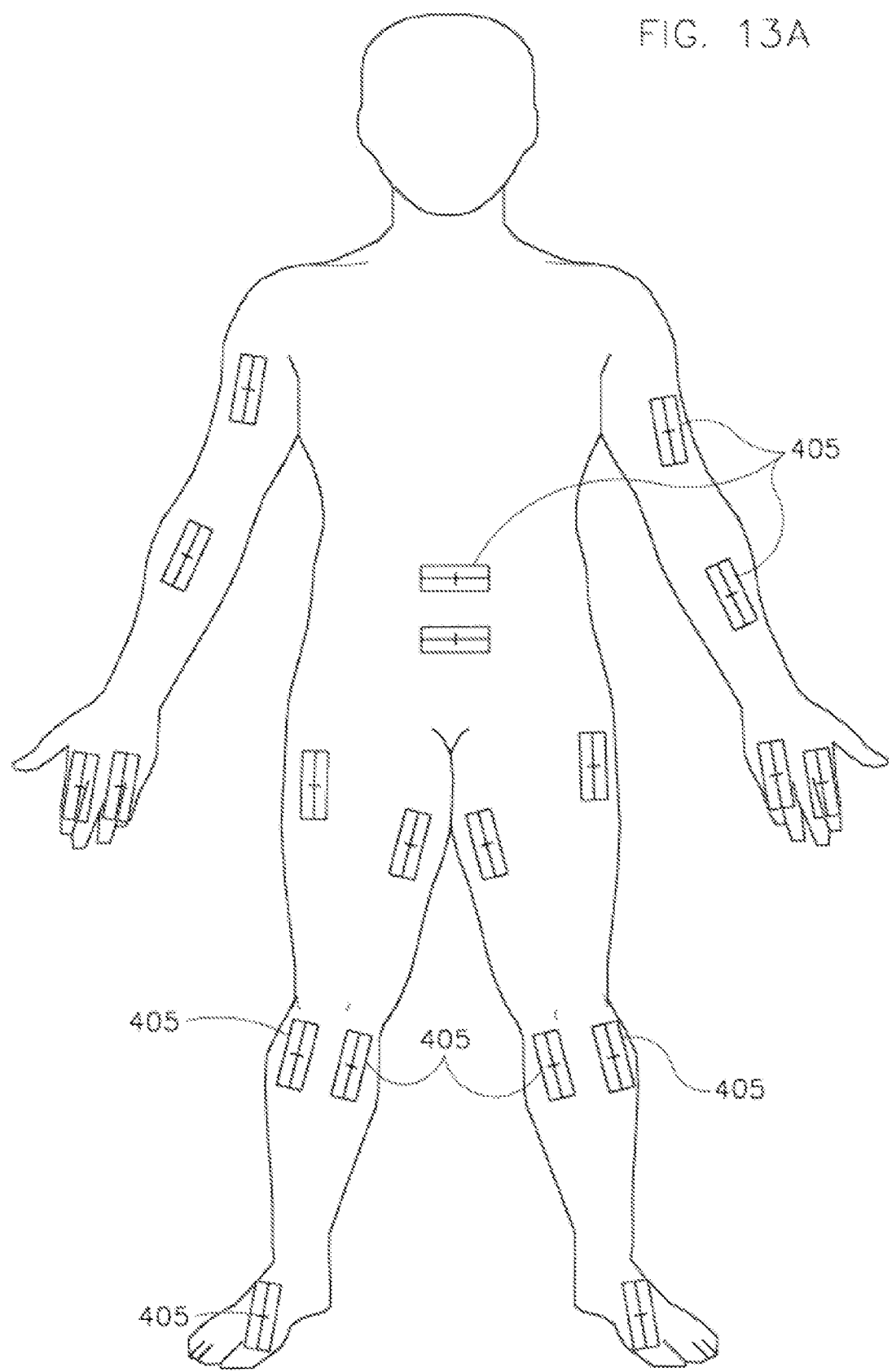
FIG. 13A illustrates various locations for single compartment sensors that can be positioned on a front side of animal body, such as a human, to measure oxygenation levels of various compartments according to one exemplary embodiment of the invention.

Referring now to FIG. 13A, this Figure illustrates various locations for single compartment sensors 405 that can be positioned on a front side of animal body, such as a human, to measure oxygenation levels of various compartments 905 according to one exemplary embodiment of the invention. FIG. 13A illustrates that the invention is not limited to compartment sensors 405 that only measure lower legs 100 of the human body. The compartment sensors 405 can measure various different compartments 905 such as, but not limited to, compartments 905 of the arm, thighs, and abdomen.

Figure 13B:
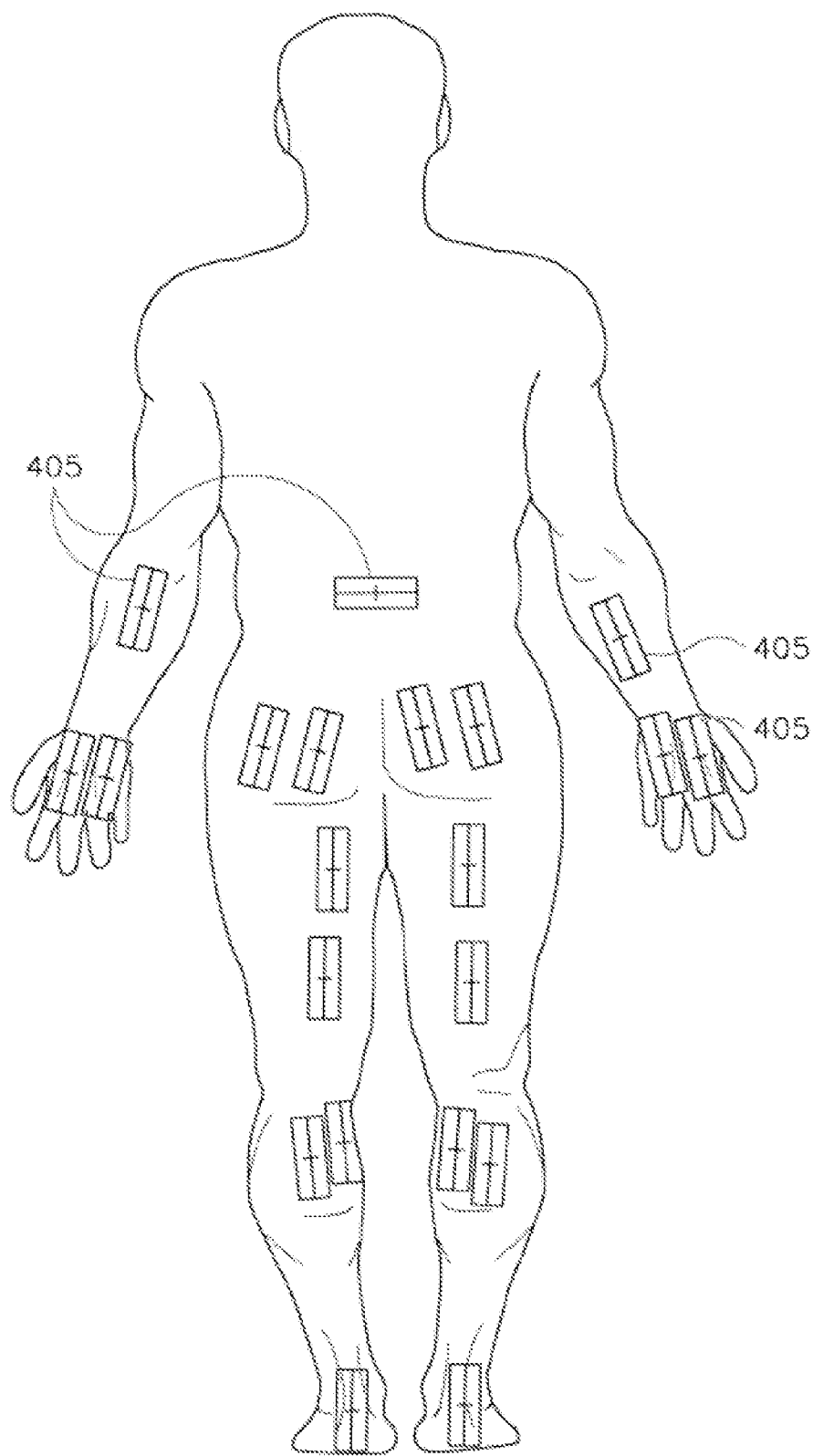
FIG. 13B illustrates various locations for single compartment sensors that can be positioned on a rear side of animal body, such as a human, to measure oxygenation levels of various compartments according to one exemplary embodiment of the invention.

Referring now to FIG. 13B, this Figure illustrates various locations for single compartment sensors 405 that can be positioned on a rear side of animal body, such as a human, to measure oxygenation levels of various compartments 905 according to one exemplary embodiment of the invention. Similar to FIG. 13A above, the compartment sensors 405 shown in this Figure can measure various different compartments 905 such as, but not limited to, compartments 905 of the arm, thighs, and abdomen. Also, while grouped compartment sensors 405 that are coupled together with expansion devices 535 are not illustrated here (such as those described in connection with FIG. 5A above), one of ordinary skill recognizes that such grouped compartment sensors can be substituted anywhere were the single compartment sensors 405 are shown.

Figure 14A:
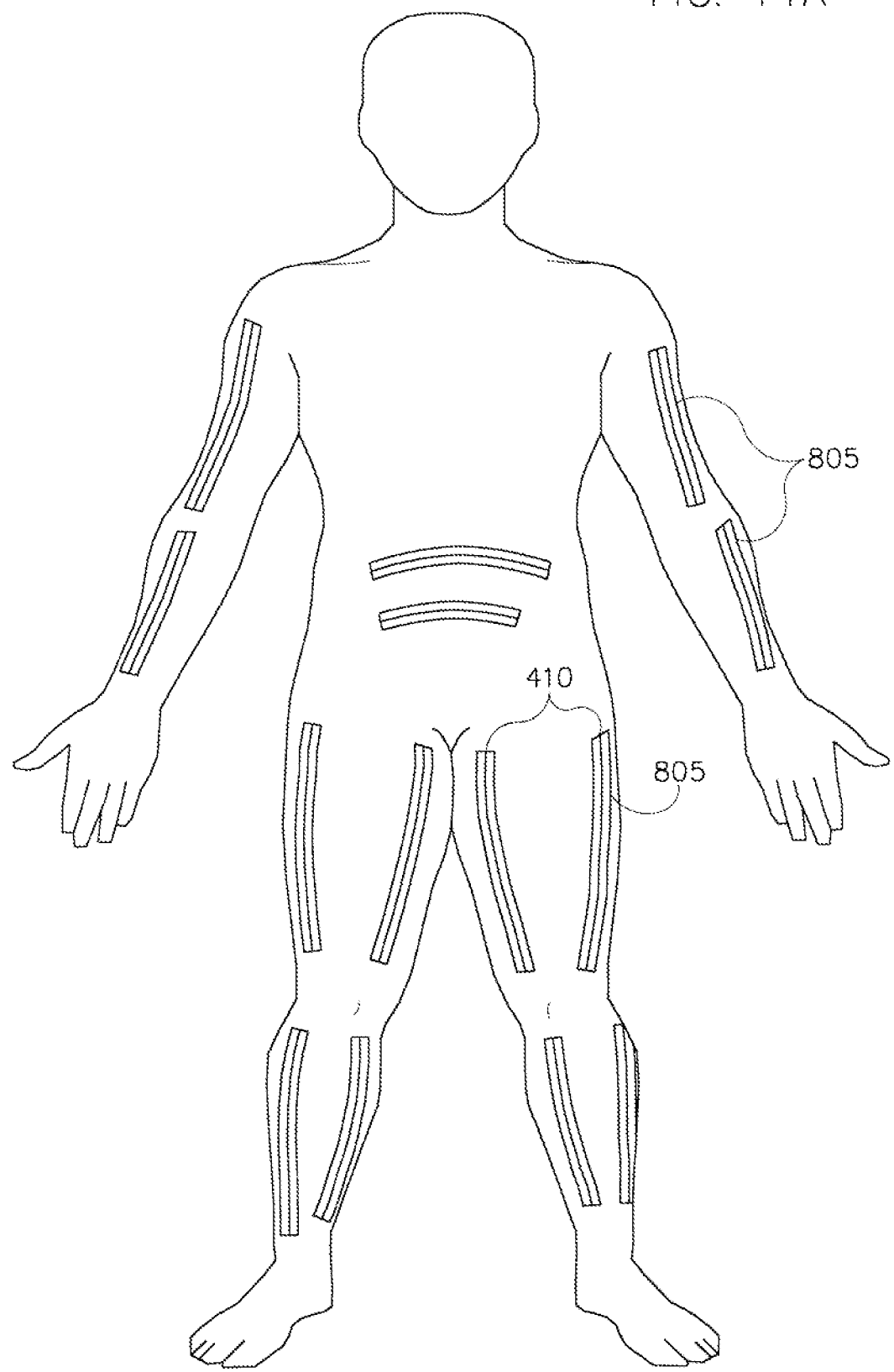
FIG. 14A illustrates various locations for compartment sensor arrays that can be positioned over compartments on a front side of an animal body, such as a human, to measure oxygenation levels of the various compartments according to one exemplary embodiment of the invention.

Referring now to FIG. 14A, this Figure illustrates various locations for compartment sensor arrays 805 that can be positioned over compartments 905 on a front side of an animal body, such as a human, to measure oxygenation levels of the various compartments 905 according to one exemplary embodiment of the invention. Like the single compartment sensor embodiments of FIGS. 13A-13B described above, the compartment sensor arrays 805 can measure various different compartments 905 such as, but not limited to, compartments 905 of the arm, thighs, and abdomen.

Figure 14B:
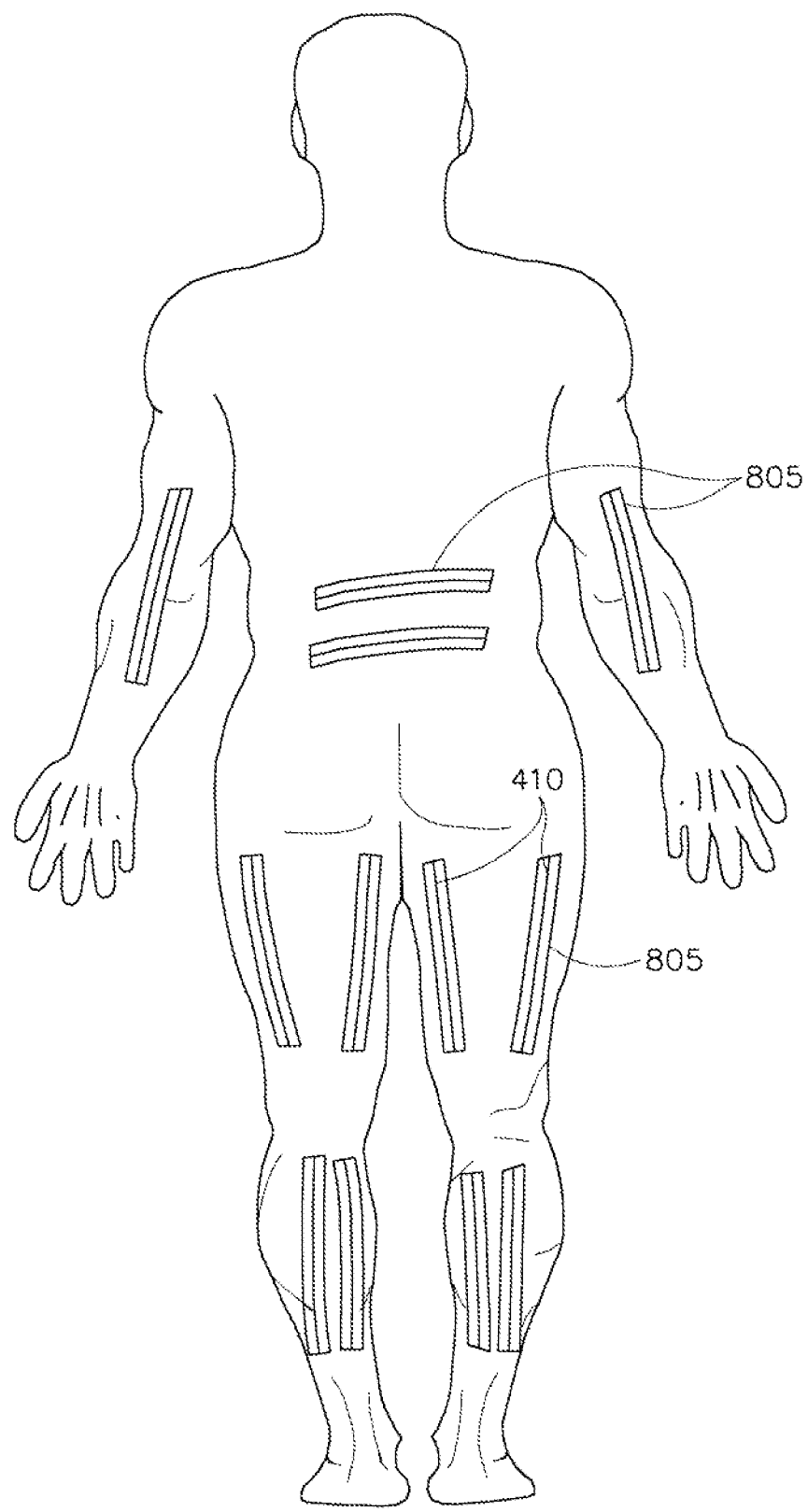
FIG. 14B illustrates various locations for compartment sensor arrays that can be positioned over compartments on a rear side of an animal body, such as a human, to measure oxygenations levels of the various compartments according to one exemplary embodiment of the invention.

Referring now to FIG. 14B, this Figure illustrates various locations for compartment sensor arrays 805 that can be positioned over compartments 905 on a rear side of an animal body, such as a human, to measure oxygenations levels of the various compartments 905 according to one exemplary embodiment of the invention. Also, while grouped compartment sensor arrays 805 that are coupled together with expansion devices 535 are not illustrated here (such as those described in connection with FIG. 8B above), one of ordinary skill recognizes that such grouped compartment sensor arrays 805 can be substituted anywhere were the individual compartment array sensors 805 are shown.

Figure 14C:
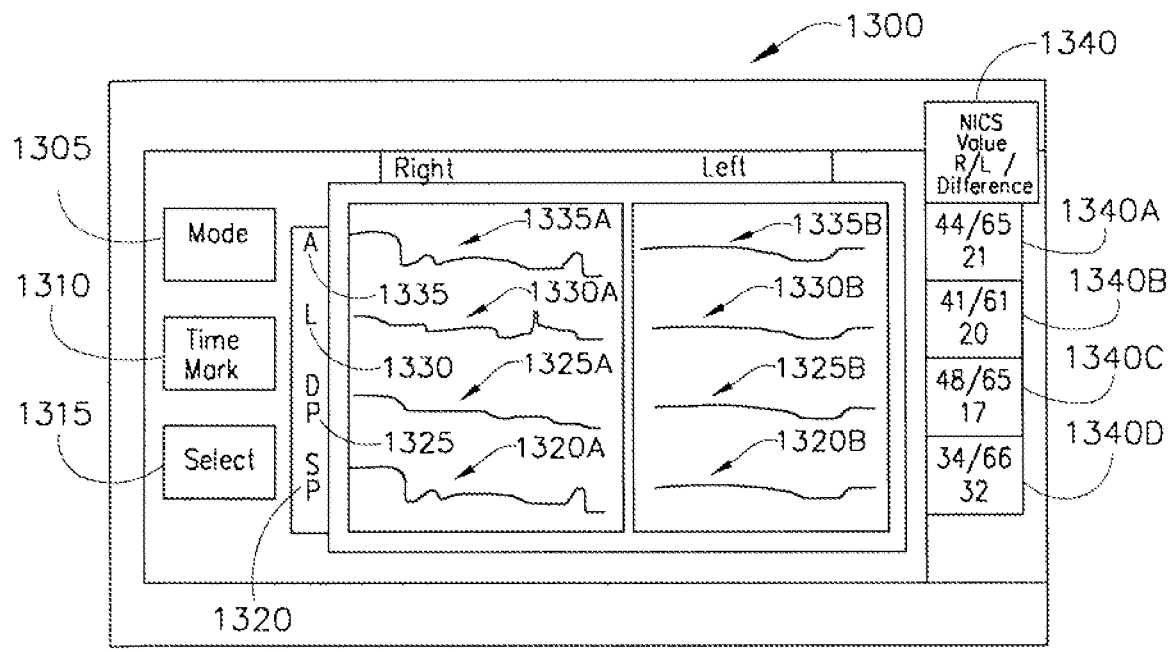
FIG. 14C illustrates an exemplary display and controls for the display device that lists data for eight single compartment sensors according to one exemplary embodiment of the invention.

Referring now to FIG. 14C, this Figure illustrates an exemplary display 1300 and controls for the display device 420 that lists data for eight single compartment sensors 405 according to one exemplary embodiment of the invention. The eight single compartment sensors 405 may be monitoring compartments of two limbs of an animal, such as two lower legs of a human patient. One limb is usually uninjured while the other limb is typically injured, though the system is not limited to unilateral injuries.

The display 1300 may provide up to eight different plots or graphs 1335A, 1330A, 1325A, 1320B, 1335B, 1330B, 1325B, 1320B of data that are taken from the eight different sensors 405 or sensor arrays 805. The first pair of right and left leg sensors may monitor the anterior compartment 905B of FIG. 9A which is displayed with the letter "A" for the first row 1335 of data. The second pair of right and left leg sensors may monitor the lateral compartment 905A of FIG. 9A which is displayed with the letter "L" for the second row 1335 of data. The third pair of right and left leg sensors may monitor the deep posterior compartment 905C which is displayed with the letters "DP" for the third row 1330 of data. The first pair of right and left leg sensors may monitor the superficial posterior compartment 905D which is displayed with the letters "SP" for the fourth row 1320 of data.

The display 1300 may also provide a measure of a difference 1340 in oxygenation levels between the injured limb or region and the uninjured limb or region. This difference may be displayed by listing the two oxygenation levels of each respective limb separated by a slash "/" line. Underneath the two oxygenation levels for a respective pair of sensors for the injured and uninjured limbs, a value which is the difference between the oxygenation levels displayed above it may be listed. For example, for the first oxygenation difference value of 1340A, the oxygenation level for the right leg sensor is the value of forty-four while the value for the left leg sensor is the value of sixty-five. In this exemplary embodiment, the right leg is injured while the left leg is uninjured. The difference value displayed under the two oxygenation levels for the first data set 1340A is twenty-one.

Initial data from patients with extremity injuries measured by the inventor have shown that muscular skeletal injuries cause hyperemia (increased blood flow and oxygen) in the injured extremity. If a compartment syndrome develops, the oxygenation drops from an elevated state to an equal and then lower level with comparison to the uninjured limb. Therefore when comparing injured and uninjured extremities, the injured limb should show increased oxygenation levels. If levels begin to drop in the injured limb compared to the uninjured limb, an alarm or alert can be triggered to warn the medical practitioner. This alarm can be visual or audible (or both).

With the display 1300, a medical practitioner can modify how data is displayed by pressing the "mode" button 1305 on the display 1300 (which may comprise a "touch-screen" type of display). The mode button 1305 permits the medical practitioner to change the display of the screen. This function would allow for selection between multiple different settings to allow for data downloading, changing the time frame for which data is displayed, etc. With the time mark "button" 1310, the medical practitioner can mark or "flag" certain data points being measured for later review. With the select "button" 1315, the medical practitioner can select between the multiple options that can be accessed through the mode button.

While the above description of FIG. 14C mentioned that eight single compartment sensors 405 produced the data of the display 1300 of FIG. 14C, the single compartment sensors 405 can be easily substituted by compartment sensor arrays 805. In such a scenario in which compartment sensor arrays 805 are used to produce the data of display 1300, the displayed values can be an "average" of the values taken from a given array 805. This "average" can be calculated by the processor of the display device 420.

Figure 14D:
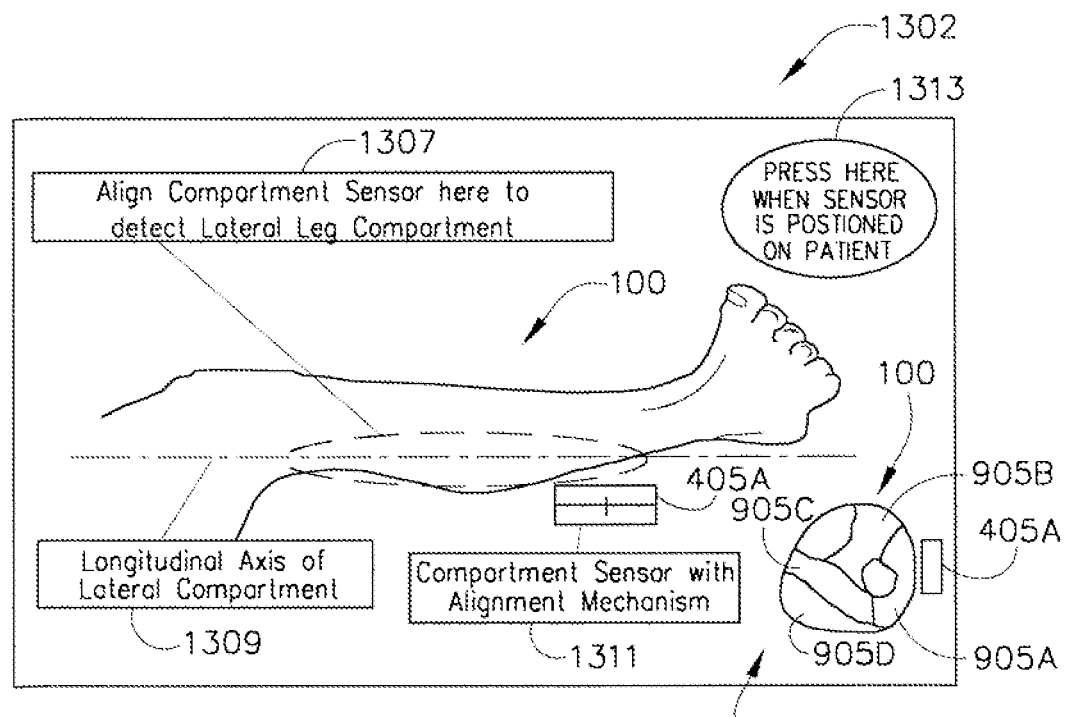
FIG. 14D illustrates an exemplary display of providing users with guidance for properly orienting a single compartment sensor over a compartment of an animal, such as a human leg, according to one exemplary embodiment of the invention.

Referring now to FIG. 14D, this Figure illustrates an exemplary display 1302 of providing users with guidance for properly orienting a single compartment sensor 405 over a compartment of an animal, such as a human leg, according to one exemplary embodiment of the invention. The display 1302 can be generated by display device 420 so that a medical practitioner is provided with instructions and graphical information on how to mount and operate the compartment sensors 405 of the system. The display may provide an illustration of the body part having the compartment of interest. In the exemplary embodiment of FIG. 14D, the compartment of interest is located within the lower human leg 100.

An illustration of the lower human leg 100 is provided in display 1302. On the body part having the compartment of interest, the display device 420 can identify the longitudinal axis 450 by marking or flagging this axis 450 with a text box label 1309. The display 1302 can also identify an illustration of the compartment sensor 405A by marking or flagging this illustration with another text box label 1311. The display 1302 can also identify a general region for a compartment of interest by encapsulating the region with a geometric outline such as an ellipse and marking this ellipse with another text box label 1307.

The display 1302 can also include a miniaturized view 1301 of a cross-section of the compartment of interest, similar to the views illustrated in FIGS. 9A and 9B for this exemplary embodiment that is assessing a lower leg compartment 905. The display 1302 may also allow the user to expand the cross-sectional view 1301 of the compartment of interest by allowing the user to double-click or touch the actual display of the cross-section. Multiple sections including an axial, coronal and/or sagittal view may be included in the on-screen instructions for placement. Upon such action by the user, the display device 420 may enlarge the cross-sectional view 1301 to a size comparable or equivalent to that illustrated in FIG. 9A. Once the medical practitioner has positioned the sensor 405 on the patient over the desired compartment of interest, the display 1302 can be refreshed to include the next compartment of interest.

Figure 15A:
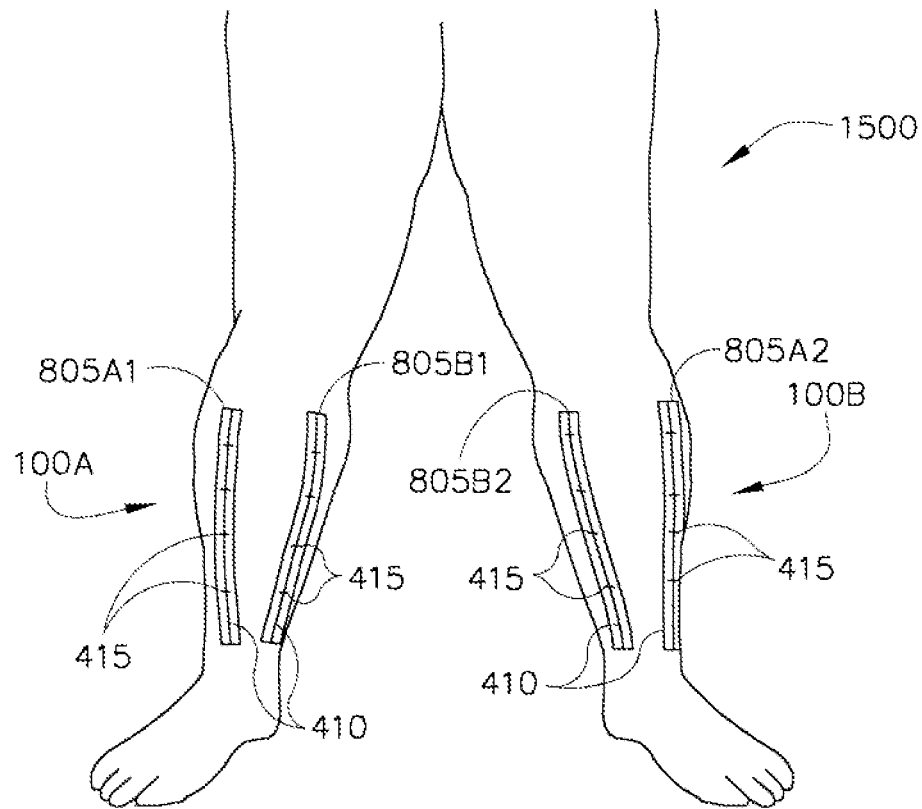
FIG. 15A illustrates a front view of lower limbs, such as two lower legs of a human body, that are being monitored by four compartment sensor arrays according to an exemplary embodiment of the invention.

Referring now to FIG. 15A, this Figure illustrates a front view of lower limbs, such as two lower legs of a human body, that are being monitored by four compartment sensor arrays 805 according to an exemplary embodiment of the invention. The four sensor arrays 805 can be positioned along compartments of interest by orienting the alignment mechanism 410 along the longitudinal axis of a respective compartment. Multiple central scan depth markers 415 and numerical depths (not illustrated in FIG. 15A) can be positioned over each light source/receptor set of a sensor array 805 to locate where each measurement is obtained for identifying sites of a hematoma, which will be described in more detail in connection with FIGS. 15B-16 below.

Figure 15B:
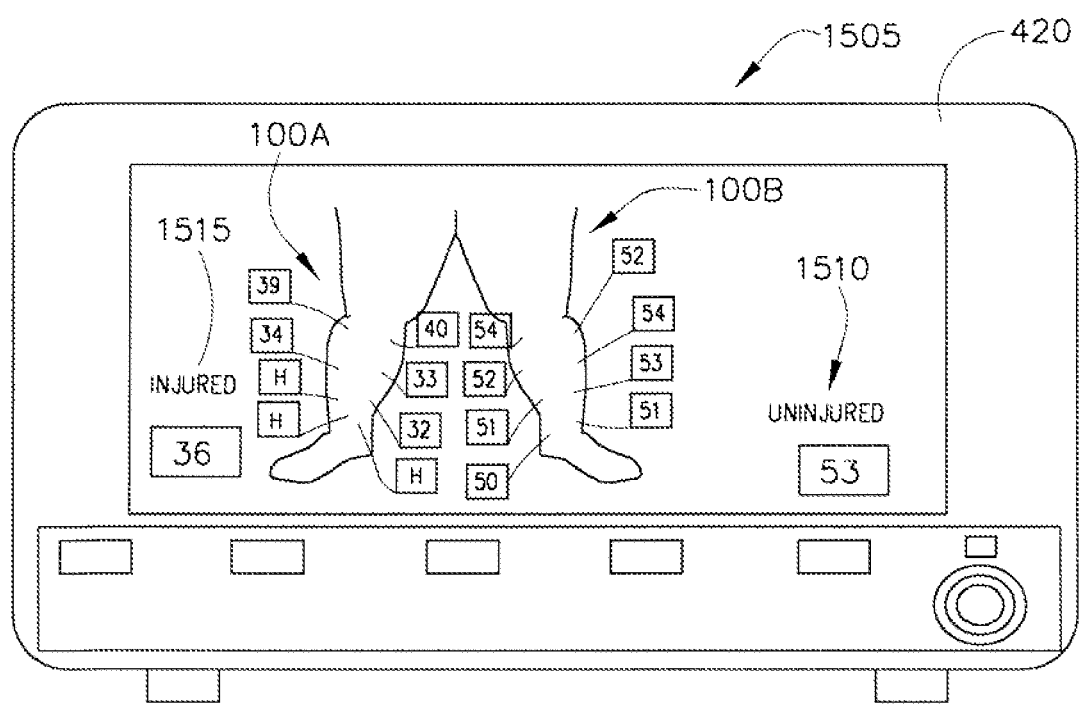
FIG. 15B illustrates a display of the display device that can be used to monitor hematomas and/or blood flow according to one exemplary embodiment of the invention.

Referring now to FIG. 15B, this Figure illustrates a display 1505 of the display device 420 that can be used to monitor hematomas and/or blood flow according to one exemplary embodiment of the invention. The display 1505 can include an average oxygenation level 1515 of thirty-six at an instant of time that is determined from the two compartment sensor arrays 805A1, 805B1 of a patient's right leg 100A which is injured in this exemplary case. Meanwhile, the display 1505 can also include an average oxygenation level 1510 of fifty-three at the same instant of time that is determined from the two compartment sensor arrays 805A2, 805B2 of a patient's left leg 100B which is uninjured in this exemplary case.

The display 1505 can also provide oxygenation values that it is receiving from each of the individual sensors 405 in a first sensor array 805 not illustrated. For the injured right leg 100A illustrated in the display, the oxygenation levels vary between thirty-two and forty-four. However, in the exemplary embodiment illustrated in FIG. 15B, there are three individual sensors 405 (not illustrated in this Figure) of the sensor array 805A1 that are not producing any oxygenation values which have been provided with the letter "H" to denote a possible hematoma. For the uninjured leg 100B, the individual compartment sensors 405 (not illustrated) of the two sensor arrays 805A2, 805B2 have provided oxygenation levels that range between 50 and 54 which are believed to be in the normal range for normal blood flow. Also, While individual sensors 405 that are not illustrated here (such as those described in connection with FIG. 4A above), one of ordinary skill recognizes that such individual compartment sensors 405 can be substituted anywhere were the compartment array sensors 805 are shown.

Figure 16:
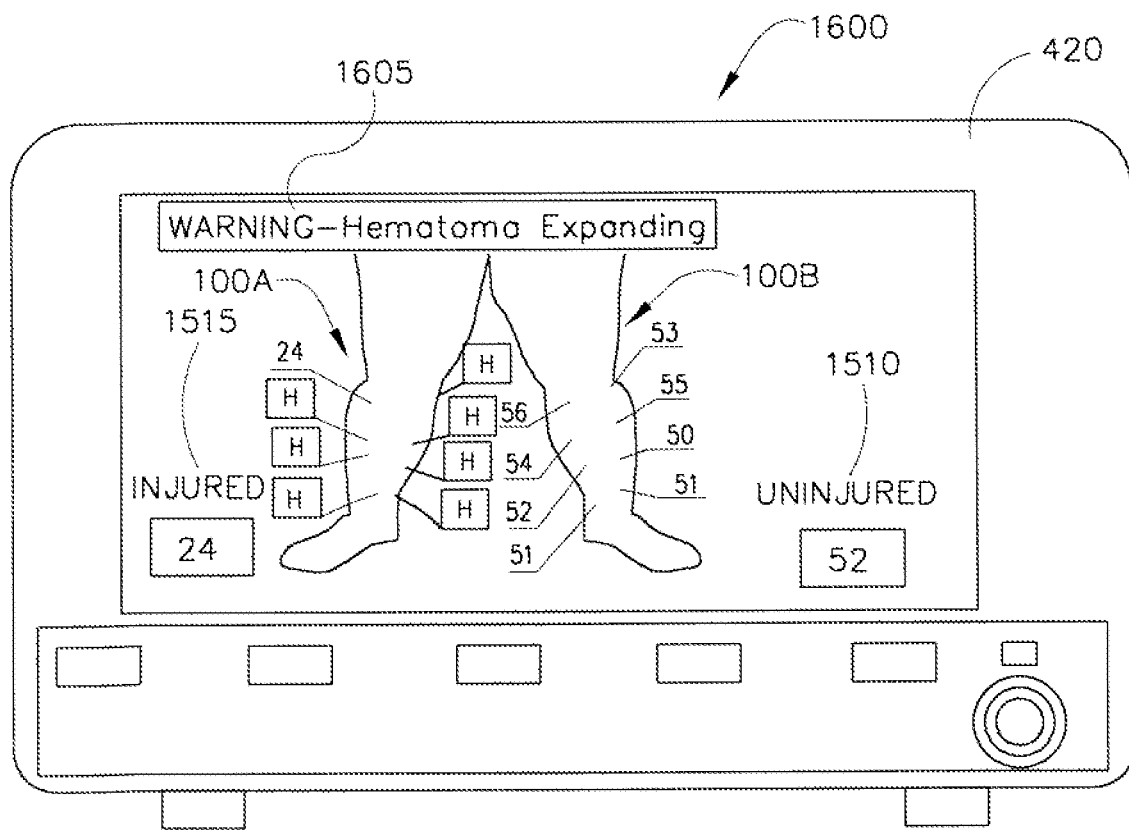
FIG. 16 illustrates a display of the display device for an instant of time after the display of FIG. 15B and which can be used to monitor hematomas and/or blood flow according to one exemplary embodiment of the invention.

Referring now to FIG. 16, this Figure illustrates a display 1600 of the display device 420 for an instant of time after the display of FIG. 15B and which can be used to monitor hematomas and/or blood flow according to one exemplary embodiment of the invention. The display 1600 illustrates that the hematoma or absence of healthy blood flow condition being tracked by sensor arrays 805A1, 805B1 (of FIG. 15A) is expanding. The display 1600 can include a warning message 1605 such as "WARNING—HEMATOMA EXPANDING!" to alert the medical practitioner of the changing conditions of the compartments 905 of interest in the injured or traumatized area. In FIG. 16, the average oxygenation level 1515 of the injured leg 100A decreased in value from thirty-six to twenty-four. Further, the number of individual sensors 405 (not illustrated but values shown) detecting a hematoma or lack of healthy blood flow condition increased from two sensors detecting the condition in FIG. 15B to seven sensors detecting the condition in FIG. 16 as indicated by the "H" values on display 1505. Meanwhile, the average oxygenation level 1515 of the uninjured left leg 100B changed slightly from fifty-three to fifty-two.

With the display 1600 that provides the compartment sensors 405 with "H" values in combination with the central scan depth markers 415 provided on the sensor arrays 805, the medical practitioner can easily locate the physical sites on the leg 100 that contain the hematoma or lack of healthy blood flow. These positions can also be used by the medical practitioner to locate appropriate amputation level for diabetics or peripheral vascular disease, since peripheral vascular disease is typically worse distally (closer to the toes) and gradually improves closer to the knee. The compartment sensor 405 or more specifically the array system 805 can be used to aid a clinician or surgeon in determining the level of amputation for peripheral vascular disease and or diabetes mellitus. By obtaining multiple readings at different levels from the knee to the ankle, the surgeon can determine the appropriate level for amputation. The level of amputation is important since if the tissue is not well perfused, the surgical wound will not heal and require revision surgery and more of the patient's leg must be removed.

Figure 17:
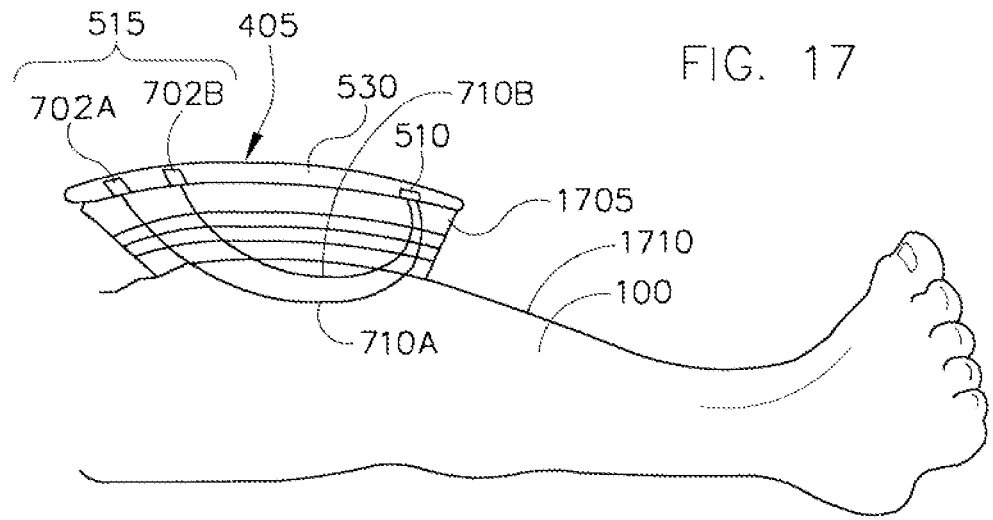
FIG. 17 illustrates a sensor design for measuring the optical density of skin according to one exemplary embodiment of the invention.

Referring now to FIG. 17, this Figure illustrates a sensor design for measuring the optical density of skin according to one exemplary embodiment of the invention. The depth of tissue measurement using NIRS is based on separation of the optical transmitter 510 and the optical receiver (see FIGS. 18A-B). In order to obtain readings of only the skin (very shallow depths), the separation between the optical transmitter 510 and optical receiver 515 would have to be very small and which may not be feasible. In this exemplary embodiment, the sensor 405 can comprise a material 1705 of known optical density that can be positioned between the substrate 530 and the skin 1710. In this way, the light mean paths 710A, 710B will only penetrate upper layers of the leg 100, such as the skin layers 1710. The thickness of the known material 1705 can be varied to adjust for different desired scan depths made by the light mean paths 710A, 710B. Since the optical density of the material 1705 is known, then any near infrared light absorption will be attributable to the layers of tissue of interest. And in this case, the optical density of the skin 1710 can be determined. According to a further exemplary embodiment, one of the photoreceptors 702A, 702B can be removed from the optical receiver 515 in order to decrease the depth of the scan. For example, if the second photoreceptor 702A was removed, the depth of the scan would only extend as deep as the light mean path 710B for the photoreceptor 702B.

The inventor has recognized that skin pigmentation can affect the oxygenation values of a patient that uses near-infrared compartment sensors 405. This effect on oxygenation levels is also acknowledged in the art. See an article published by Wassenar et al. in 2005 on near-infrared system (NIRS) values. As with solar light, skin pigmentation caused by the biochemical melanin is a major factor in light absorption. In the inventor's research, skin pigmentation has been demonstrated to be a significant factor in measuring oxygenation levels among patients. The inventor has discovered that there was approximately a ten point difference when comparing low pigmentation subjects (Caucasians, Hispanics & Asians) with higher pigmented subjects (African American). The pigmented subjects had average scores of approximately ten points lower when compared to non-pigmented subjects. See Table 1 below that lists data on the difference between measured oxygenation levels of uninjured patients due to skin pigmentation.

TABLE #1

Difference in measured oxygenation levels between White and Dark Pigmentation Skinned Subjects

| Avg | White | Dark | Diff | p value |
|---|---|---|---|---|
| Anterior | 60 | 51 | 9 | <0.0001 |
| Lateral | 61 | 52 | 9 | <0.0001 |
| Deep Post | 66 | 53 | 13 | <0.0001 |
| Sup Post | 66 | 52 | 14 | <0.0001 |

N=10 (White) and 17 (Dark) (This study compared 10 white subjects to 17 darker pigmented subjects)
Statistics used a non paired, two tail student t-test for p-values
P values show very statistically significant differences between white (Caucasian, Asian & Hispanic) vs. Dark (African American) subjects The p-value can be described as the chance that these findings were due to chance alone. In all four compartments, the chance of finding the difference (9-14) in average value between the two groups (dark and white) was less than 0.01% or less than 1 out of 10,000. In other words the likelihood of these findings occurring by chance alone is very unlikely. By convention, statistically significant findings are considered to be less than 5% or a p-value of <0.05 in comparison. See APPENDIX A for the raw data that supports this data.

Conventional studies (Wassenar et al., 2005 and Kim et al., 2000) have showed that when subjects increase their activity, dark pigmented people tend to have higher rates of loss of signal.

There have been no attempts as of this writing to account for skin pigmentation, or optical density, in oxygenation levels detected with sensors like the compartment sensor 405 discussed above. Therefore, the design illustrated in FIGS. 17-18 have been developed by the inventor to account for pigmentation optical density. With the embodiments of FIGS. 17-18, skin pigmentation influences can be calibrated and accounted for when measuring oxygenation levels with sensors 405 that use near infrared light absorption principles. In this way, true or more accurate oxygenation levels of subcutaneous tissue such as muscle, cerebral matter or organ tissue may be obtained. This calibration or pigmentation accounting would also allow for comparison of values between different patients, since each individual will likely have different skin pigmentation values.

Figure 18A:
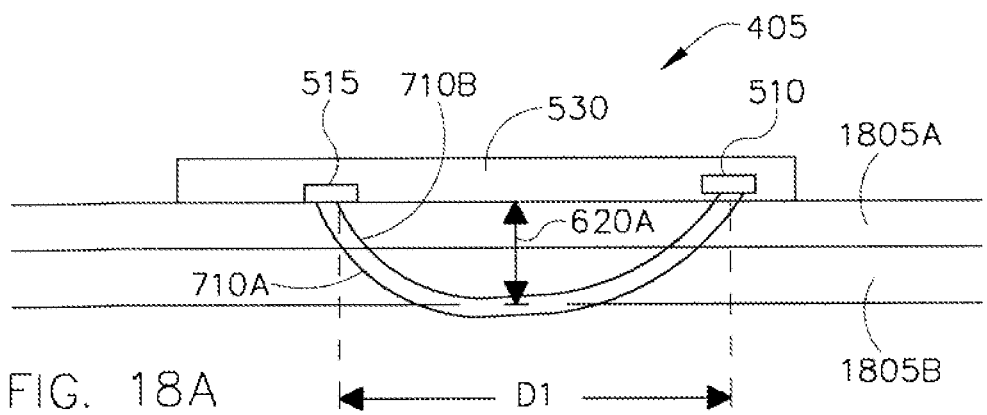
FIG. 18A illustrates a sensor that can penetrate two layers of skin to obtain optical density values according to one exemplary embodiment of the invention.

Referring now to FIG. 18A, this Figure illustrates a sensor 405 that can penetrate two layers of skin 1805A, 1805B to obtain optical density values according to one exemplary embodiment of the invention. The distance D1 between the optical transmitter 510 and optical receiver 515 can be predetermined based on the scan depth 620A that is desired.

Figure 18B:
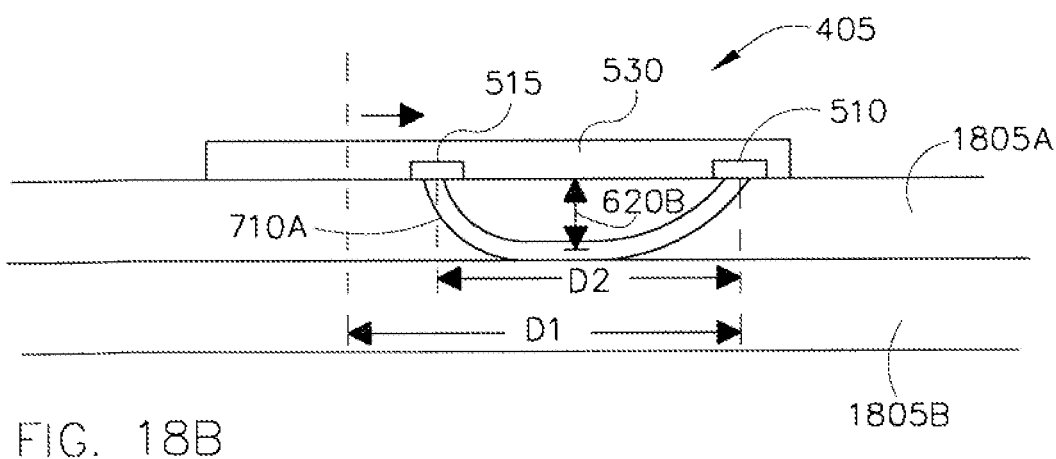
FIG. 18B illustrates a sensor that can penetrate one layer of skin according to one exemplary embodiment of the invention.

Referring now to FIG. 18B, this Figure illustrates a sensor 405 that can penetrate one layer of skin 1805A according to one exemplary embodiment of the invention. This figure demonstrates how the depth of measurement for oxygenation levels using the sensors 405 that operate according to near infrared light absorption principles is usually directly proportional to the optical transmitter and optical receiver separation distance D. In FIG. 18B, the separation distance D2 is smaller than that of the separation distance D1 of FIG. 18A. Accordingly, the central scan depth 620B of FIG. 18B is also shorter than the central scan depth 620A of FIG. 18A.

According to one exemplary embodiment of the invention, the separation D1 and D2 between the optical transmitter 510 and optical receiver 515 can range between approximately five millimeters to two centimeters. This separation distance D can be optimized to obtain an accurate reading of only the skin in the particular area of interest. One of ordinary skill in the art recognizes that skin is not a constant depth or thickness throughout a human body. Therefore, the depth 620 of the scan of a sensor 405 for which it is designed (ie. the leg for compartment syndromes) may preferably be designed to vary to obtain an accurate optical density value for skin in that specific body location.

Figure 18C:
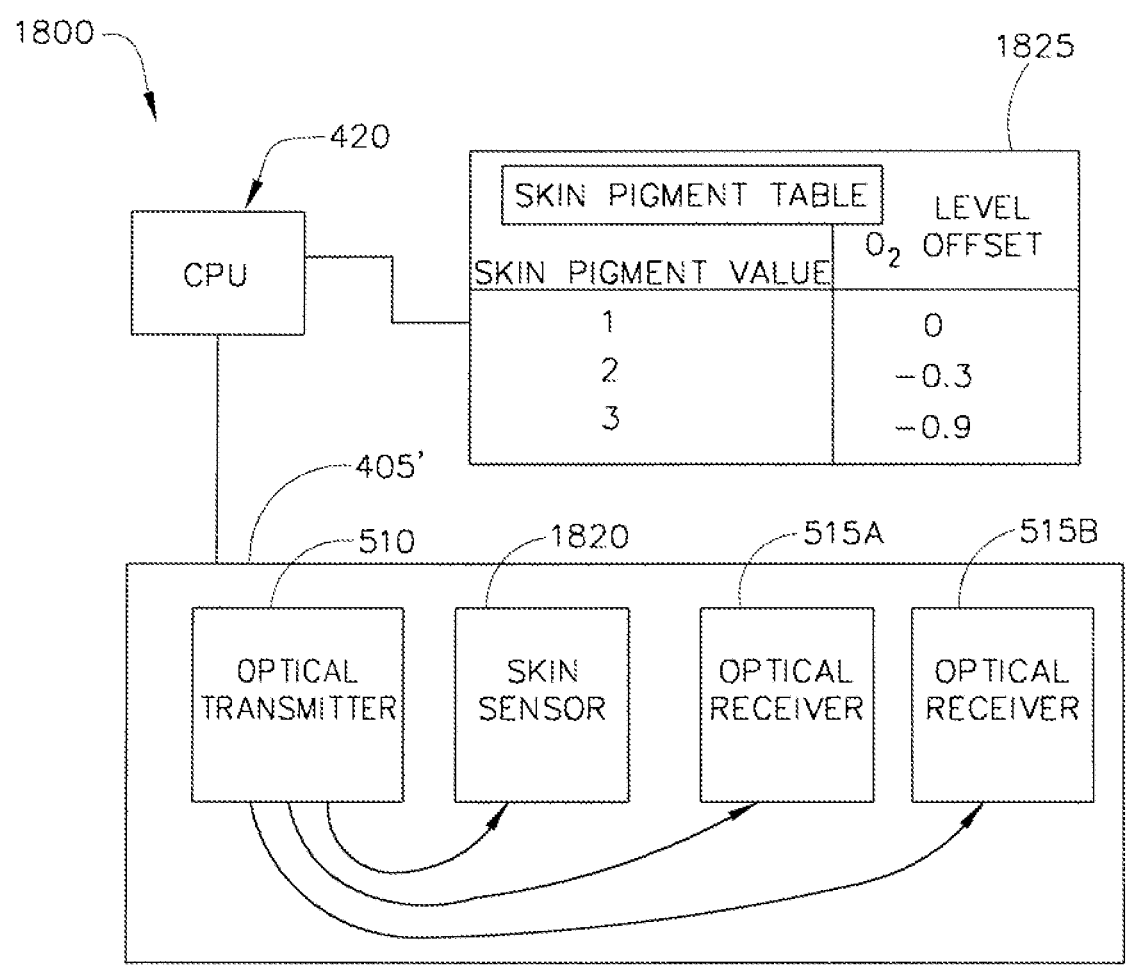
FIG. 18C illustrates a modified compartment monitoring system that can correlate skin pigmentation values with skin optical density values in order to provide offset values for oxygenation levels across different subjects who have different skin pigmentation according to one exemplary embodiment of the invention.

Referring now to FIG. 18C, this figure illustrates a modified compartment monitoring system 1800 that can correlate skin pigmentation values with skin optical density values in order to provide offset values for oxygenation levels (derived from near infrared light absorption principles) across different subjects who have different skin pigmentation according to one exemplary embodiment of the invention. The system 1800 can comprise a central processing unit of the display device 420 or any general purpose computer. The CPU of the display device 420 can be coupled to a compartment sensor 405' that has been modified to include a skin pigment sensor 1820.

The skin pigment sensor 1820 may be provided with a known reflectance and that can be used to calibrate the compartment sensor 405' based on relative reflectance of skin pigment which can affect data generated from oxygenation scans. For example, the skin sensor 1820 can comprise a narrow-band simple reflectance device, a tristimulus colorimetric device, or scanning reflectance spectrophotometer. Conventional skin sensors available as of this writing include mexameter-18 (CK-electronic, Koln, Germany), chromameters, and DermaSpectrometers. Other devices appropriate and well suited for the skin sensor 1820 are found in U.S. Pat. No. 6,070,092 issued in the name of Kazama et al; U.S. Pat. No. 6,308,088 issued in the name of MacFarlane et al; and U.S. Pat. No. 7,221,970 issued in the name of Parker, the entire contents of these patents are hereby incorporated by reference.

The skin sensor 1820 can determine a standardized value for skin pigmentation of a patient by evaluating the melanin and hemoglobin in the patient's skin. Once the skin melanin or pigment value is determined it can be correlated to its calculated absorption or reflectance (effect) on the oxygenation levels using a predetermined calibration system, such as the skin pigment table 1825 illustrated in FIG. 18C. From the skin pigment table 1825, the CPU 420 can identify or calculate an oxygenation offset value that can be incorporated in tissue hemoglobin concentration calculations for deep tissue oxygenation scans. Accounting for skin pigmentation will usually allow for information or values to be compared across different subjects with different skin pigmentation as well as using the number as an absolute value instead of monitoring simple changes in value over time.

Figure 19:
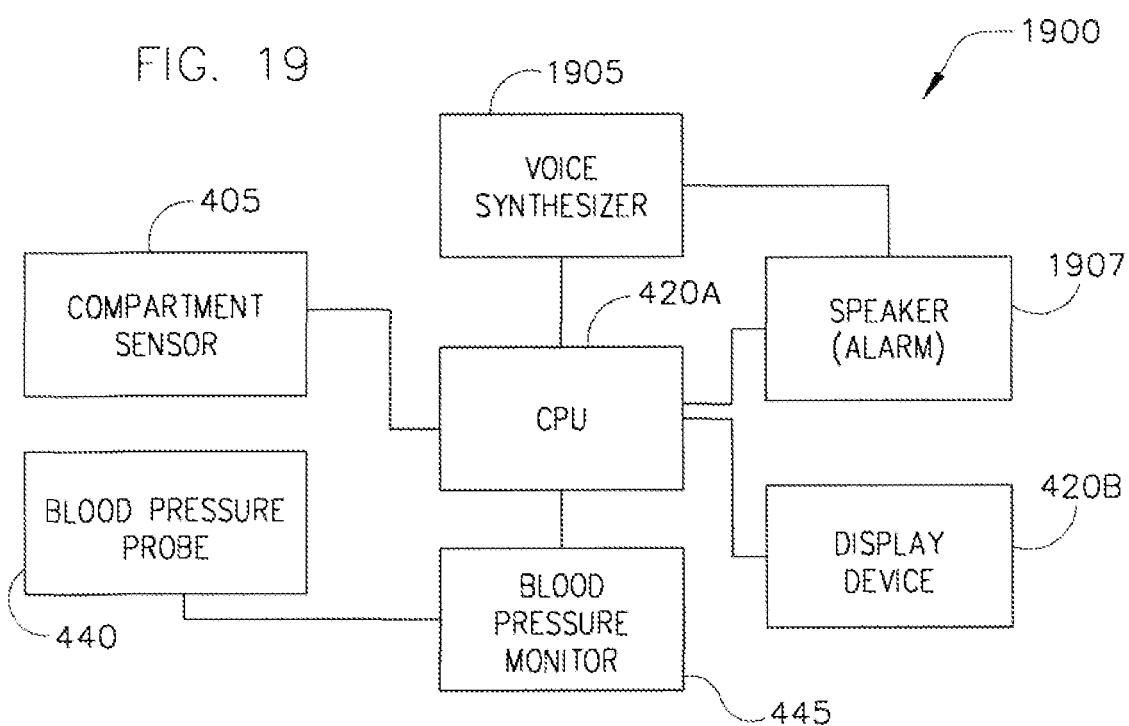
FIG. 19 is a functional block diagram of the major components of a compartment monitoring system that can monitor a relationship between blood pressure and oxygenation values according to one exemplary embodiment of the invention.

Referring now to FIG. 19, this figure is a functional block diagram of the major components of a compartment or oxygenation monitoring system 1900 that can monitor a relationship between blood pressure and oxygenation values according to one exemplary embodiment of the invention. The compartment monitoring system 1900 can include a CPU 420A of a display device 420B that is coupled to compartment sensors 405, a blood pressure probe 440, and a blood pressure monitor 445. The CPU 420A may also be coupled to a voice synthesizer 1905 and a speaker 1907 for providing status information and alarms to a medical practitioner.

The CPU 420A can receive data from the blood pressure monitor 445 in order to correlate oxygenation levels with blood pressure. The CPU 420A can activate an alarm, such as an audible or visual alarm (or both) with the voice synthesizer 1905 and speaker or displaying a warning message on the display device 420B when the diastolic pressure of a patient drops. It has been discovered by the inventor that perfusion can be significantly lowered or stopped at low diastolic pressures and when compartment pressures are greater than the diastolic pressure. According to one exemplary embodiment, in addition to activating an alarm, the CPU 420A of the compartment monitoring system 1900 can increase a frequency of data collection for oxygenation levels and/or blood pressure readings when a low blood pressure condition is detected by the oxygenation sensing system 1900.

Figure 20:
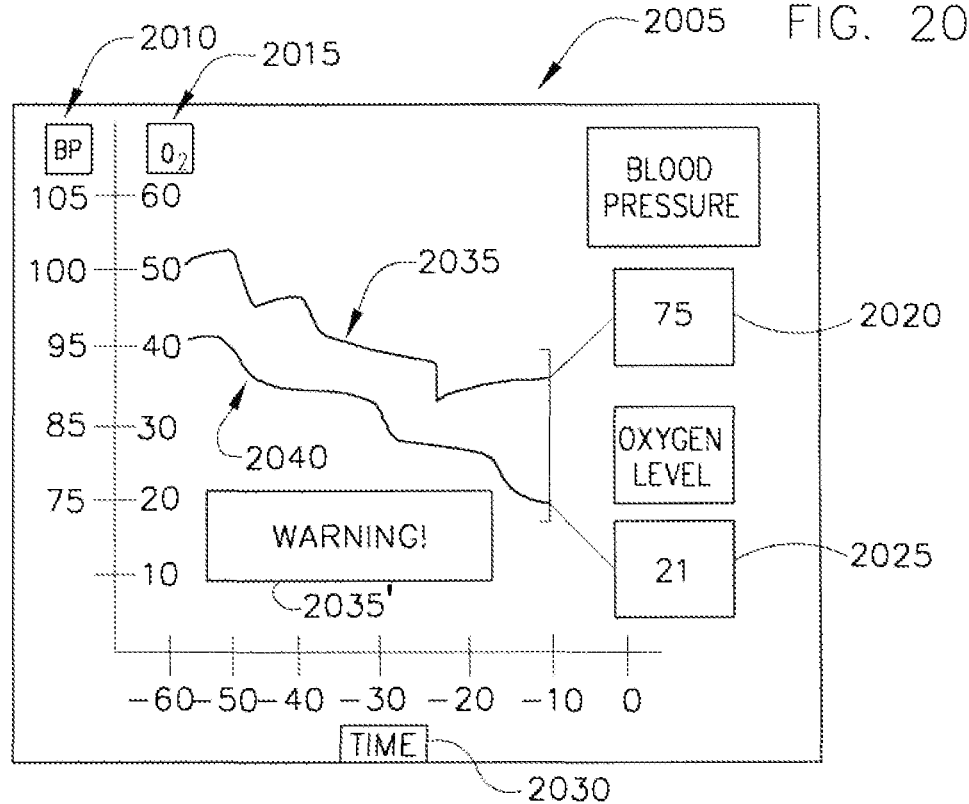
FIG. 20 is an exemplary display that can be provided on the display device and which provides current blood pressure values and oxygenation levels of a compartment of interest according to one exemplary embodiment of the invention.

Referring now to FIG. 20, this figure is an exemplary display 2005 that can be provided on the display device 420 and which provides current blood pressure values 2020 and oxygenation levels 2025 of a compartment of interest according to one exemplary embodiment of the invention. Display 2005 can be accessed by activation of the mode switch 1305 of FIG. 14.

In addition to displaying current blood pressure values 2020 and oxygenation levels 2025, the display 2005 can further include graphs that plot a blood pressure curve 2035 and an oxygenation level curve 2040. The blood pressure curve 2035 can represent blood pressure data taken over time that is plotted against the time axis 2030 (X-axis) and the blood pressure axis 2010 (first Y-axis values). The oxygenation level curve 2040 can represent oxygenation levels taken over time that is plotted against the time axis 2030 (X-axis) and the oxygenation level axis 2010 (second Y-axis values).

In this way, the relationship between blood pressure and potential compartment pressure based on the oxygenation levels can be directly tracked and monitored by a medical practitioner. As noted above, it has been discovered by the inventor that perfusion can be significantly lowered or stopped at low diastolic pressures and when compartment pressures are greater than the diastolic pressure. So when the blood pressure of a patient starts to drop and if the oxygenation levels of a compartment being tracked also start to drop, the CPU 420A can sound an audible alarm and display a warning message 2035' to the medical practitioner to alert him or her of this changing condition. This correlation between hemoglobin concentration (oxygenation levels) and diastolic pressure can be used to estimate intra-compartmental pressures without having to use invasive, conventional needle measurements.

Additionally, a running average of oxygenation values over a certain time period can be calculated and displayed. The time period could be altered by the m between multiple time periods from seconds to minutes to even hours. The purpose of the running average would be to limit the amount of variability of the oxygenation values displayed on the screen. The current instantaneous value that is displayed in existing models is very labile. By using a running average, the trends can be monitored and the instantaneous changes can be smoothed out. This ability to decrease volatility would be important to prevent continual alert triggering if an alarm value was set by the medical practitioner.

In addition, with blood pressure input as described above, the diastolic, systolic and/or mean arterial pressure (MAP) can be displayed (not illustrated) against time on the same graph. Using the two data series of oxygenation and diastolic blood pressure, an estimate of perfusion pressure (diastolic pressure minus intra-compartmental pressure) can also be estimated by the CPU 420A.

Figure 21:
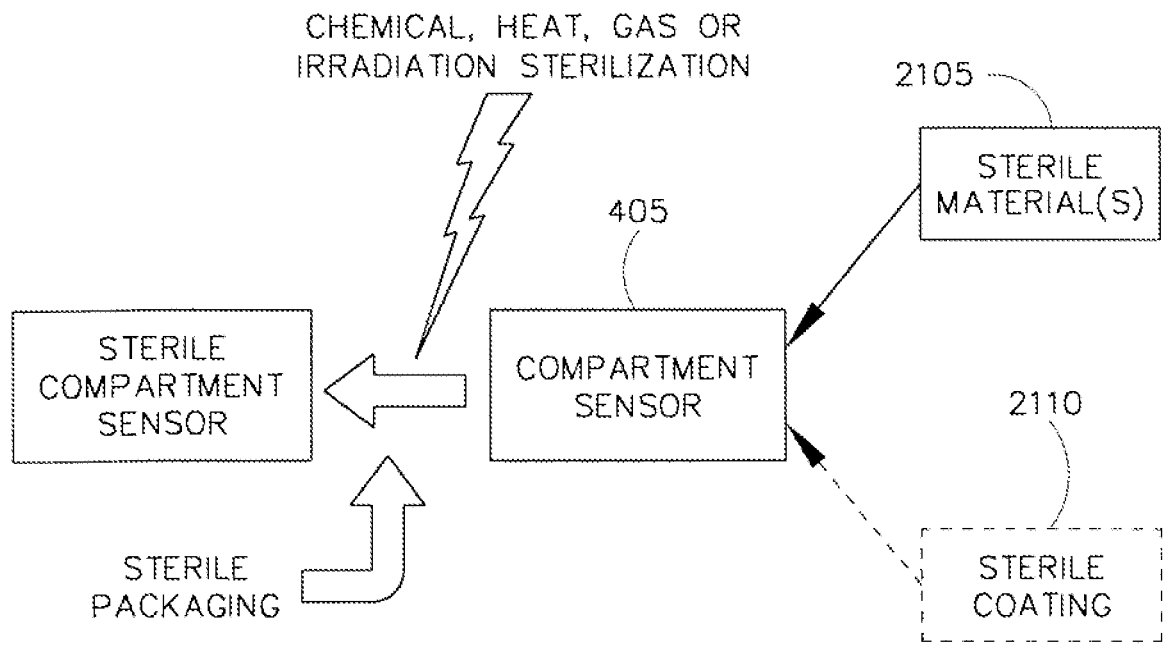
FIG. 21 is a functional block diagram that illustrates sterilized material options for a compartment sensor according to one exemplary embodiment of the invention.

Referring now to FIG. 21, this figure is a functional block diagram that illustrates material options for a compartment sensor 405 according to one exemplary embodiment of the invention. Functional block 2105 indicates that the structure of the compartment sensor can be made with sterile materials. For example, the substrate 530 (not illustrated) of the sensor 405 may be made of anyone or combination of the following materials: various polymers such as the polyurethanes, polyethylenes, polyesters, and polyethers or the like may be used. Alternatively, each compartment sensor can be made with a sterile coating 2110 that encapsulates the compartment sensor 405. The sterile coating can be applied during manufacturing of the sensor 405 or it can be applied after manufacturing and provided as a container or sealable volume. Additionally, once the unit is constructed and finished, the device can be sterilized using one or more off multiple processes including but not limited to chemical, heat, gas or irradiation sterilization.

Figure 22:
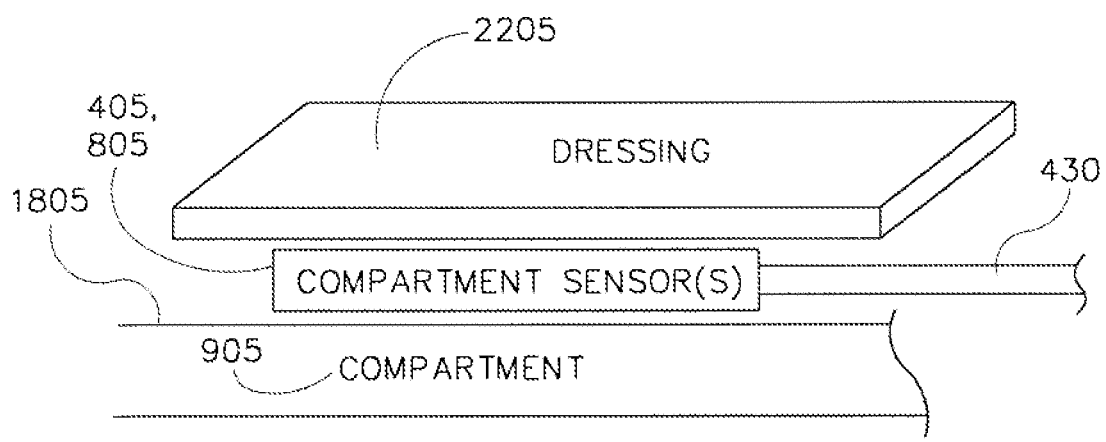
FIG. 22 illustrates an exemplary clinical environment of a compartment sensor where the sensor can be positioned within or between a dressing and the skin of a patient according to one exemplary embodiment of the invention.

Referring now to FIG. 22, this figure illustrates an exemplary clinical environment of a compartment sensor 405 where the sensor 405 can be positioned within or between a dressing 2205 and the skin 1805 of a patient according to one exemplary embodiment of the invention. Since the inventive compartment sensor 405 can be made with or enclosed by sterile materials as noted in FIG. 21 above, the compartment sensor 405 or an sensor array 805 can be positioned between a dressing 2205 and a skin layer 1805 of a patient intra-operatively. In this way, a medical practitioner can monitor a compartment 905 of interest without the need to remove the dressing 2205 or adjust the position of the compartment sensor 405.

Case Studies Using Compartment Sensors 405 and Conventional Pressure Measuring Methods Case I In 2007, a 44 year old Caucasian male fell 20 feet sustaining an isolated closed proximal tibia fracture with extension into the knee. Initial treatment included external fixation for stabilization on the day of injury. During surgery the compartments were firm but compressible. At post operative check revealed that the compartments were more firm. There was mild pain with passive stretch, though the patient was diffusely painful throughout both lower extremities. Intra-compartmental pressures were measured for all four compartments using a conventional needle method with a Striker device (Stryker Surgical, Kalamazoo, MI). The anterior and lateral pressures measured 50 mm Hg and the superficial and deep posterior compartments were 48 mm Hg. The diastolic pressure was 90 mm Hg resulting in a 40 mm Hg perfusion pressure.

Tissue oxygenation ($StO_2$) or oxygenation levels were evaluated using two compartment sensors 405. The oxygenation levels were approximately 80% in all four compartments. The compartment sensors 405 were placed on the lateral and deep posterior compartments for continual monitoring, which maintained oxygenation values near 80%. Higher percentage oxygenation levels indicate more perfusion and higher oxy-hemoglobin concentrations.

All clinical decisions were based of the clinical symptoms and pressure measurements and not on the oxygenation levels. Two hours passed and compartment pressures were repeated. The anterior and lateral compartments remained at 50 mm Hg. The superficial and deep posterior compartments rose to 50 mm Hg as well. The patient's diastolic pressure remained at 90 mm Hg maintaining 40 mm Hg of perfusion pressure. The oxygenation values remained near 80% for both the lateral and deep posterior compartments. Clinical symptoms were monitored closely throughout the night.

Approximately 24 hours after the initial injury, the patient became more symptomatic and began requiring more pain medication. Intra-compartmental measurements were repeated. The anterior and lateral compartments remained at 51 mm Hg. The superficial and deep posterior compartments measured 61 mm Hg and 63 mm Hg respectively. However, the diastolic pressure dropped to 74 mm Hg decreasing the perfusion pressure to 11 mm Hg. Based on the pressure measurements and clinical symptoms, the patient underwent fasciotomy and was found to have no gross evidence of muscle necrosis or neuromuscular sequelae at late follow up.

Throughout the monitoring period, the lateral compartment maintained an oxygenation level of approximately 80%. The oxygenation levels in the deep posterior compartment began in the eighties and started to drop approximately three hours after the second compartment pressure measurement. At time of fasciotomy, the oxygenation level for the deep posterior compartment was 58%. The gradual decline in muscle oxygenation mirrored the decrease in perfusion pressure over an extended period of time.

This first case suggests that the compartment sensors 405 can be used to continually monitor an injured extremity. Initially, the patient had elevated intra-compartmental pressures, but the perfusion pressure was greater than 30 mm Hg. The ensuing increase in clinical symptoms and decrease in perfusion pressure correlated with the gradual decrease in oxygenation levels. Impaired perfusion was reflected in a decline in the oxygenation levels. These results are consistent with a previous study by Garr et al. who showed a strong correlation between oxygenation levels and perfusion pressures in a pig model. This case also demonstrates the ability of compartment sensors 405 to differentiate between compartments in the leg since the oxygenation levels in the lateral compartment remained elevated while the deep posterior values declined.

Case II

Also in 2007, a 32 year old Hispanic male sustained an isolated, closed Schatzker VI tibial plateau fracture after falling from a scaffold. On initial evaluation, the patient had tight compartments, but there were no clinical symptoms of compartment syndrome. Active and passive range of motion resulted in no significant pain. Based on the concerns for the tense leg, intra-compartmental pressure measurements were obtained using a Stryker device.

All compartments were greater than 110 mm Hg. The patient's blood pressure was 170/112 mm Hg. The decision to perform a four compartment fasciotomy was made. The compartment sensors 405 were placed on the deep posterior compartment as well as the lateral compartment for continual monitoring. The lateral compartment was unable to give a consistent reading due to hematoma interference. The initial reading for the deep posterior was an oxygenation level of 65%. The deep posterior tissue oxygenation level steadily declined from 65% to 55% over the hour of preoperative preparation.

Upon intubation, a sharp drop in the oxygenation levels from 55% to 43% was observed. The anesthesia record showed a concomitant drop in blood pressure at the time of induction from 171/120 mm Hg to 90/51 mm Hg. The patient underwent an uneventful fasciotomy and external fixation. Tissue examination showed no gross signs of muscle necrosis and at nine months follow-up there were no signs of sequelea. The oxygenation level monitoring of the compartment was acutely responsive and showed real time changes to a decline in perfusion pressure in an injured extremity.

The responsiveness of the compartment sensors 405 to intra-compartmental perfusion pressure is demonstrated by this second case study. This patient was initially asymptomatic even though his compartments were over 110 mm Hg in all compartments. The oxygenation levels from the compartment sensors 405 were able to detect gradual perfusion declines over the hour prior to fasciotomy. Prior to induction of anesthesia, the patient was able to maintain some tissue oxygenation by maintaining a high diastolic blood pressure. Once the patient was anesthetized during intubation, the diastolic pressure was significantly reduced. The oxygenation levels of the compartments dropped within thirty seconds of induction because the slight perfusion gradient was completely abolished by the induced hypotension.

Case III

In 2007, a 62 year old Asian male suffered a closed midshaft tibia fracture in a motor vehicle crash. The patient was unresponsive and hypotensive at the scene of the accident and intubated prior to arrival. Upon presentation, the patient was hypotensive with a blood pressure of 90/55 mm Hg. The injured leg was clinically tight on examination.

Oxygenation levels were measured for all four compartments. The oxygenation levels were approximately at 50% for the anterior and lateral compartments while the two posterior compartments were approximately at 80%. The compartment sensors 405 were placed on the anterior and superficial posterior compartments for continued monitoring. Intra-compartmental pressures were measured at 50 mm Hg and 52 mm Hg in the anterior and lateral compartments respectively using the conventional Striker device (needle pressure measuring method). The superficial and deep compartment pressures were 19 mm Hg and 20 mm Hg respectively. After the patient was stabilized by the trauma team, he underwent fasciotomy. There were no gross signs of muscle necrosis and no complications at 7 months follow-up. Muscle oxygenation was able to differentiate between compartments with hypoperfusion and adequate perfusion in a hypotensive and intubated patient.

This third case is evidence that the compartment sensors 405 are useful in assessing established or existing compartment syndromes. The compartment sensors 405 can provide useful information in patients that are unable to give feedback during a clinical examination such as this patient who was intubated and hypotensive upon examination. These findings correlate with the findings by Arbabi et al. who demonstrated oxygenation levels to be responsive in hypotensive and hypoxic pigs in a laboratory setting. The compartment sensors 405 can distinguish between different compartments and their respective perfusions. Clinically, in this case, the whole leg was tense, but intra-compartmental pressures were only elevated in the anterior and lateral compartments. The oxygenation levels measured by the compartment sensors 405 were proportional to the perfusion pressure with low values in the anterior and lateral compartments, but elevated values in the two posterior compartments.

Conclusion for Three Case Studies:

These three cases suggest that compartment sensors 405 are responsive and proportional to perfusion pressures within the injured extremity. These findings support previous studies documenting the importance of perfusion pressure and not an absolute value in the diagnosis of compartment syndrome. The compartment sensors can distinguish between compartments and is useful in the unresponsive, intubated and hypotensive patient. Lastly, the compartment sensors 404 have the potential to offer a continual, noninvasive and real time monitoring system that is sensitive in the early compartment syndrome setting. In all three cases, a difference in oxygenation levels was demonstrated prior to any irreversible tissue injury.

Case IV

A 60 year old Middle Eastern male was shot in the right thigh. Initially the thigh was swollen but the patient was comfortable. After approximately 12 hours after the initial injury the patient began to complain of increasing pain and required more pain medication. The thigh was more tense upon clinical exam. The patient was taken to the OR for fracture fixation and potential fasciotomy of the thigh.

NIRS sensors were placed on the anterior, posterior and medial (adductors) compartments of the thigh. Values for the injured side were similar or decrease when compared to the uninjured side. As previously described, injured tissue should show increased values due to hyperemia. The injured side anterior, posterior and medial values were 54, 53 and 63 respectively. The uninjured values for the anterior, posterior and medial were 51, 55 and 63 respectively.

The compartment pressures were measured in all three compartments. The intra-compartmental pressures for the anterior, posterior and adductors were 44, 59 and respectively. Once the patient was induced for anesthesia and the patient's blood pressure dropped from 159/90 to 90/61, the patients NIRS values dropped within in 30 seconds of the his blood pressure drop. Once the blood pressure was dropped and the perfusion pressure was eliminated, the new values for the anterior, posterior and medial compartments were 29, 40 and 35.

Study: Sphygmomanometer Model & Invention's Sensitivity & Responsiveness

A study was conducted to determine the sensitivity and responsiveness of the inventive compartment monitoring system 400. Specifically, the purpose of the study was to evaluate the invention over the anterior compartment with a cuff around the thigh at different pressures (simulating a compartment Syndrome) to show responsiveness to increasing pressures in the leg.

The inventor's hypothesis was that the inventive compartment monitoring system 400 will show normal oxygenation at levels below pressures equivalent to compartment syndrome. Once pressures become equal to the diastolic blood pressure, it was believed the inventive system 400 would show significant deoxygenation because the capillary perfusion pressure will be passed. Continued monitoring will be obtained until a plateau or nadir is obtained.

Materials & Methods:

Thigh Cuff Pressures: 0 mmHg: Baseline;
Increase cuff by 10 mmHg and hold for 10 minutes;
At the end of each ten minute period blood pressure and NIRS values were obtained;
Repeat incremental increases until obtain decreased oxygenation level readings; and
Observe post release response & time to return to baseline Outcomes:

It was confirmed that the compartment monitoring system 400 is sensitive to changing pressures. A correlation with decreased perfusion was discovered once the pressure approaches diastolic pressure. The inventive system 400 does not reflect complete vascular compromise until tourniquet pressure supersedes systolic blood pressure because of venous congestion. These findings are consistent with previously described studies.

Statistical Analysis:

A significant difference is observed once tourniquet pressure equals the diastolic pressure (Perfusion pressure of zero). The venous congestion phenomenon which has been described with the tourniquet model for compartment syndromes maintains some flow until cuff pressure is raised to above systolic pressure (no flow). Venous congestion is the phenomenon when the higher systolic blood pressure is able to overcome the tourniquet pressure applied to the leg during that burst of pressure created by the heart's contraction when the tourniquet compression is above diastolic pressure but below systolic pressure.

Figure 23:
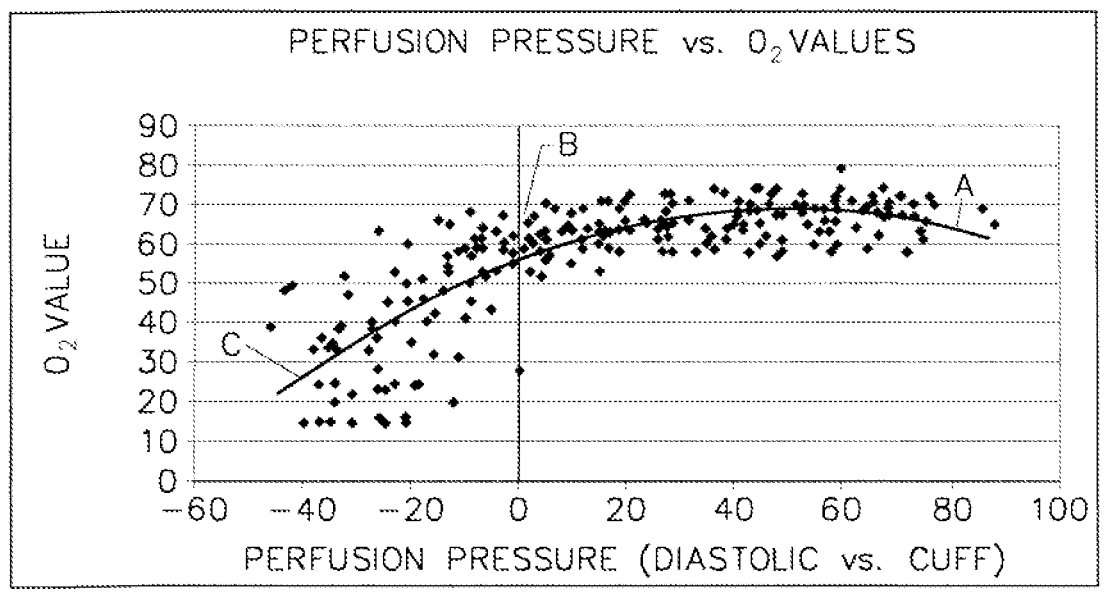
FIG. 23 is a graph of perfusion pressure plotted against oxygenation levels of a study conducted to determine the sensitivity and responsiveness of the inventive compartment monitoring system according to one exemplary embodiment of the invention.

Referring now to FIG. 23, this figure is a graph 2300 of perfusion pressure plotted against oxygenation levels ($O_2$) of the study conducted to determine the sensitivity and responsiveness of the inventive compartment monitoring system 400. The section between points A and B show the combined points of all subjects studied during the study when the tourniquet pressure was below the diastolic pressure. As shown in the graph, the grouping is mostly flat and does not show any decrease as the tourniquet pressure is increased. After point B between point B and C, the tourniquet pressure is above the diastolic pressure and the perfusion pressure becomes zero or negative. During this section of the graph, there is a significant drop in muscle oxygenation. The data points in FIG. 23 use the actual compartment monitoring values, which as described above, can vary based on skin pigmentation. Therefore, there is a wider range of values in oxygenation numbers and a wider spread of data points. See APPENDIX B for the raw data that supports this graph 2300.

Figure 24:
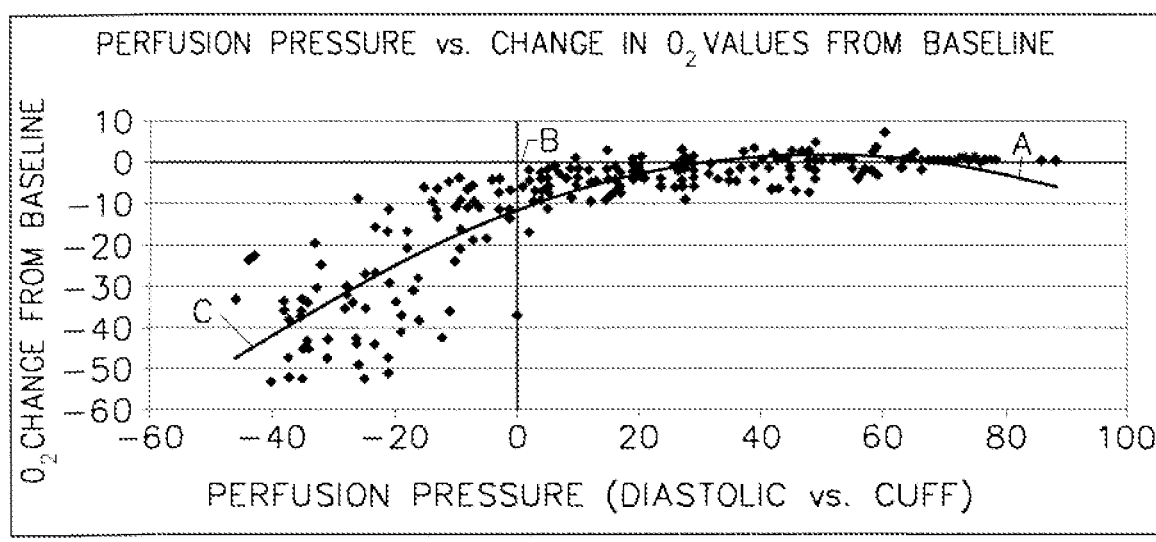
FIG. 24 is a graph of perfusion pressure plotted against a change in the oxygenation levels from a baseline for each subject of the study conducted to determine the sensitivity and responsiveness of the inventive compartment monitoring system according to one exemplary embodiment of the invention.

Referring now to FIG. 24, this figure is a graph 2400 of perfusion pressure plotted against a change in the oxygenation levels ($O_2$) from a baseline for each subject of the study conducted to determine the sensitivity and responsiveness of the inventive compartment monitoring system 400.

In the FIG. 24, the change from baseline was used instead of the absolute number presented by the compartment sensor. The effects of pigment were removed when change from baseline values was used. Baseline was defined as the value before the tourniquet was placed. The spread between data points is much less. As shown again between points A and B, there is a very small and gradual decrease in tissue oxygenation until point B (moving from high perfusion pressures to lower perfusion pressures or from right to left). Once the perfusion pressure, becomes zero or negative, the change from baseline was much larger and more rapid. Both graphs show how the tissue oxygenation is highly sensitive to perfusion pressure and the critical point is when the perfusion pressure changes from positive to negative. As described above, the diagnosis of compartment syndrome is based on the perfusion pressure (diastolic pressure minus compartment pressure). Therefore, the compartment monitoring system 400 has the capability to show real-time changes in perfusion prior to any irreversible tissue damage. See APPENDIX B for the raw data that supports this graph 2300.

This study supports the theory that oxygenation levels measure with the compartment sensors 405 decrease as perfusion pressure also decreases (Perfusion pressure=diastolic−cuff pressure). The study also indicates that there are no significant changes in measured oxygenation levels until there is increase above the diastolic pressure. The findings of this study as illustrated in FIGS. 23 and 24 correlate with previous studies using other determinants of flow (Xenon clearance; Clayton, 1977; Dahn, 1967; Heppenstall, 1986; Matava, 1994).

Study of Established Acute Compartment Syndromes:

Based on the clinical evaluation in established acute compartment syndrome patients the diagnosis of compartment syndrome was made. Its purpose was to evaluate the ability of the inventive compartment monitoring system 400 to detect hypoperfusion in the different compartments of the lower leg. This evaluation was made to demonstrate the invention's sensitivity to increased pressures versus uninjured legs.

Hypothesis:

There will be a significant difference between the injured and uninjured values of the compartment monitoring system 400. There will also be an inverse relationship between compartment pressures and measured oxygenation levels by the sensors 405. In other words, the oxygenation values would be directly proportional to perfusion pressures.

Material & Methods:

Oxygenation levels and pressure measurements for each compartment in established compartment syndromes were obtained. Readings for both legs were compared for each compartment.

Unknowns:

How will thick subcutaneous fat affect the compartment sensors 405?

What values will we obtain for the posterior compartments?

Preliminary Results:

Hyperemia (increased oxygenation levels) for fractures without any compartment syndrome symptoms has been demonstrated by the inventors studies (Table #3 and #4). In early compartment syndromes, the oxygenation values were equal between the two different legs. Once the compartment syndrome became advanced, and the perfusion pressure was decreased or eliminated, the oxygenation values in the injured leg dropped below the uninjured leg. There was some difficultly in obtaining oxygenation levels over a hematoma. Therefore, when oxygenation values between the two legs become equal, there should be concern for a compartment syndrome and fasciotomy should be considered. Once the injured levels drop below the uninjured leg, a fasciotomy should be performed.

Oxygenation levels are extremely responsive to changes in perfusion in regards to pressure changes. Compartment sensors 405 can differentiate between compartments. Oxygenation levels can work and are accurate in intubated patients. Oxygenation levels do respond over extended time periods and over very short periods of time and rapid changes in intra-compartmental pressures.

Oxygenation levels and hyperemia are maintained at least two to three days post injury or surgery. Post-operative values are also high in the operated on leg—~69-72 (Standard deviation of 9-12) with an average difference of 15-17%. The compartment sensors 405 work as a noninvasive tool. Oxygenation levels can be monitored by sensors 405 over extended periods of time. Compartment sensors 405 do respond to changes in perfusion both gradual and sudden. The sensors 405 can differentiate between different compartments.

TABLE #2

Comparison of Oxygenation Levels between Injured Limb and Non-injured Limb

| Avg | Injured | Uninjured | Diff | p value |
|---|---|---|---|---|
| Anterior | 46 | 54 | −6 | 0.07 |
| Lateral | 45 | 54 | −9 | 0.01 |
| Deep Post | 54 | 68 | −14 | 0.05 |
| Sup Post | 50 | 60 | −10 | 0.04 |

Significant difference using one tailed, paired student t-test was used for statistical analysis.

In three out of four compartments, the p-value showed statistical significance (p-value<0.05). The one compartment that was not less than 0.05, the anterior compartment, the p-value was 0.07 which is very close to 0.05. As described below, the normal situation should be the opposite. The injured side should be and is shown to be significantly higher when compared to the uninjured side. The p-value can be described as the chance that these findings were due to chance alone. By convention, statistically significant findings are considered to be less than 5% or a p-value of <0.05 in comparison. This means that there is a 5% chance that these findings are due to chance alone and that there is no difference between the two groups. See APPENDIX A for the raw data that supports this data.

Study of Fracture Hyperemia with Inventive Compartment Monitoring System 400

A study of fracture hyperemia with the inventive compartment monitoring system 400 was made. The purpose of this study was to examine non compartment syndrome patients with fractures of the lower leg.

Hypothesis:

The injured leg will show a hyperemic response to injury and have elevated blood flow causing an increase in oxygenation values.

Materials & Methods:

Compare uninjured leg to injured leg to see if there is a statistical and reproducible increase at time of injury. The data is important to describe normal fracture response to compare with compartment syndrome response.

Results:

Patients have approximately 15 pts higher on the injured side compared to the uninjured side. Time of measurement was approximately 16 hours post injury (range 2,52).

TABLE #3

Oxygenation Values for Injured versus Uninjured Lower Leg Measurements.

| Avg | Injured | Uninjured | Diff | p value |
|---|---|---|---|---|
| Anterior | 69 | 55 | 14 | <0.0001 |
| Lateral | 70 | 55 | 15 | <0.0001 |
| Deep Post | 74 | 57 | 17 | <0.0001 |
| Sup Post | 70 | 56 | 14 | <0.0001 |

N=26 (there were 26 subjects examined in this study.)
Statistical analysis calculated p-values using a two tailed, paired student t-test.

In normal lower leg fracture situations without vascular injury or compartment syndrome, comparison between injured and uninjured legs show that the injured leg should be significantly higher with and average elevation of between 14 and 17 points. This finding is consistent with the hyperemia associated with injury. This effect is a long lasting effect that lasts over 48 hours after injury and surgery as seen by these results. The p-value can be described as the chance that these findings were due to chance alone. In all four compartments, the chance of finding the difference (14-17) in average value between the two groups (injured and uninjured) was less than 0.01% or less than 1 out of 10,000. In other words the likelihood of these findings occurring by chance alone is very unlikely. By convention, statistically significant findings are considered to be less than 5% or a p-value of <0.05 in comparison. See APPENDIX A for the raw data that supports this data.

TABLE #4

Oxygenation Values for Injured versus Uninjured Lower Leg Measurements 2 Days After Surgery.

| Avg | Injured | Uninjured | Diff | p value |
|---|---|---|---|---|
| Anterior | 71 | 55 | 16 | <0.0001 |
| Lateral | 70 | 54 | 16 | <0.0001 |
| Deep Post | 73 | 58 | 15 | <0.0001 |
| Sup Post | 73 | 56 | 17 | <0.0001 |

N=17 (This study included 17 patients)
Average time of measurement was 71 hours after injury and 44 hours after operation The p-value can be described as the chance that these findings were due to chance alone. In all four compartments, the chance of finding the difference (15-17) in average value between the two groups (injured and uninjured) was less than 0.01% or less than 1 out of 10,000. In other words the likelihood of these findings occurring by chance alone is very unlikely. By convention, statistically significant findings are considered to be less than 5% or a p-value of <0.05 in comparison. See APPENDIX A for the raw data that supports this data.

TABLE #5

Uninjured Controls Comparing Right and Left Leg Differences.

| Avg | Right | Left | Diff | Avg Val |
|---|---|---|---|---|
| Anterior | 55 | 54 | 1 | 55 |
| Lateral | 56 | 54 | 2 | 56 |
| Deep Post | 60 | 58 | 2 | 59 |
| Sup Post | 59 | 58 | 1 | 58 |

N=to 25 (There were 25 patients included in this study.)
No difference was found between right and left sides.

These findings are important for two different reasons. First, the difference between the two legs was very small (on average between 1 or 2 points). Therefore, the other findings that show significant differences between legs cannot be explained as normal variance. Uninjured patients have oxygenation values between the two legs that are typically very similar (within 1-5 points of each other). Second, normal oxygenation values for uninjured subjects were in the high 50's. This value varied based on pigmentation of the skin as showed above. See APPENDIX A for the raw data that supports this data.

Exemplary Method for Monitoring Oxygenation Levels of a Compartment

Figure 25:
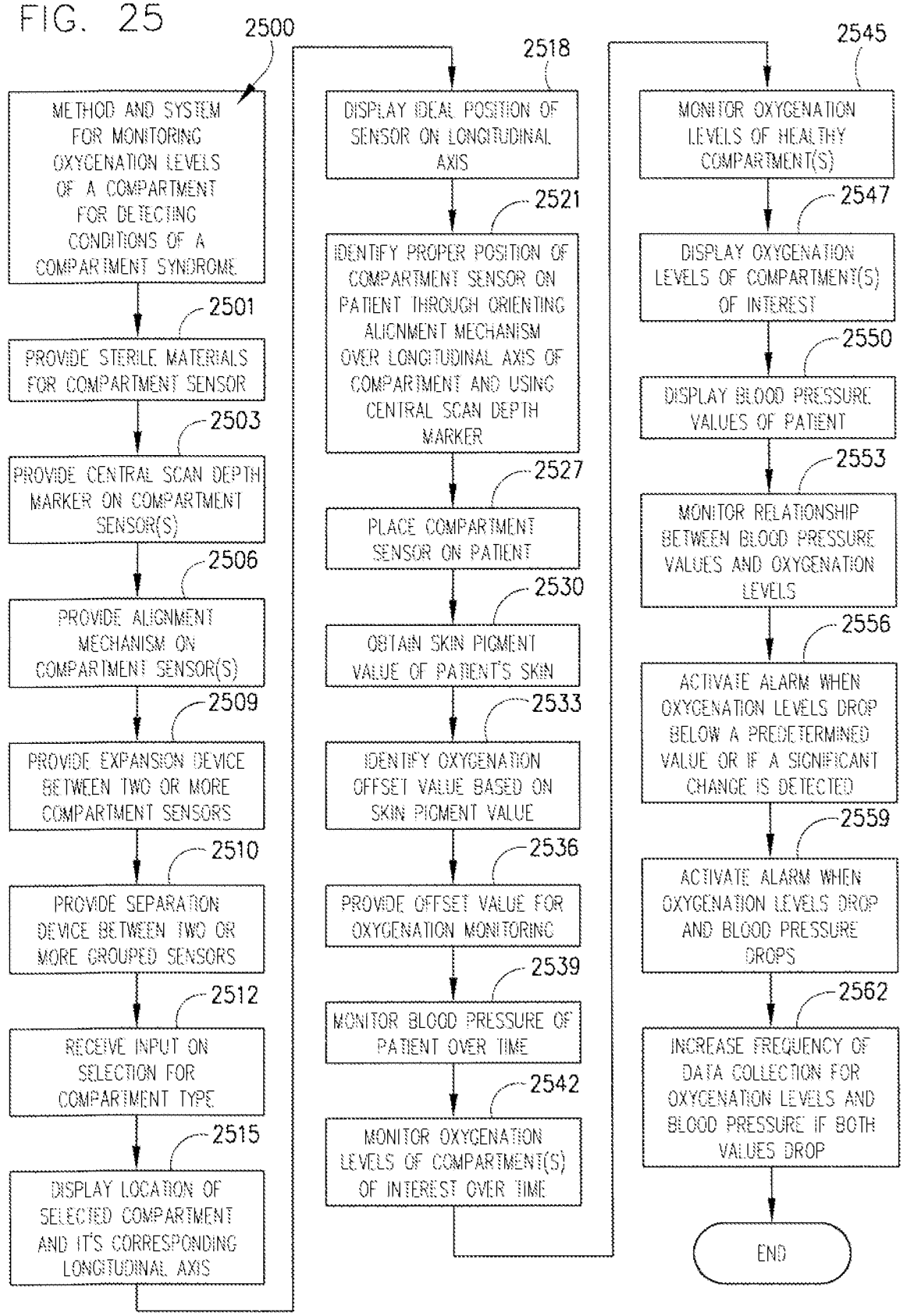
FIG. 25 is a logic flow diagram illustrating an exemplary method for monitoring oxygenation levels of a compartment according to one exemplary embodiment of the invention.

Referring now to FIG. 25, this figure is logic flow diagram illustrating an exemplary method 2500 for monitoring oxygenation levels of a compartment according to one exemplary embodiment of the invention. The processes and operations of the inventive compartment monitoring system 400 described below with respect to the logic flow diagram may include the manipulation of signals by a processor and the maintenance of these signals within data structures resident in one or more memory storage devices. For the purposes of this discussion, a process can be generally conceived to be a sequence of computer-executed steps leading to a desired result.

These steps usually require physical manipulations of physical quantities. Usually, though not necessarily, these quantities take the form of electrical, magnetic, or optical signals capable of being stored, transferred, combined, compared, or otherwise manipulated. It is convention for those skilled in the art to refer to representations of these signals as bits, bytes, words, information, elements, symbols, characters, numbers, points, data, entries, objects, images, files, or the like. It should be kept in mind, however, that these and similar terms are associated with appropriate physical quantities for computer operations, and that these terms are merely conventional labels applied to physical quantities that exist within and during operation of the computer.

It should also be understood that manipulations within the computer are often referred to in terms such as listing, creating, adding, calculating, comparing, moving, receiving, determining, configuring, identifying, populating, loading, performing, executing, storing etc. that are often associated with manual operations performed by a human operator. The operations described herein can be machine operations performed in conjunction with various input provided by a human operator or user that interacts with the computer.

In addition, it should be understood that the programs, processes, methods, etc. described herein are not related or limited to any particular computer or apparatus. Rather, various types of general purpose machines may be used with the following process in accordance with the teachings described herein.

The present invention may comprise a computer program or hardware or a combination thereof which embodies the functions described herein and illustrated in the appended flow charts. However, it should be apparent that there could be many different ways of implementing the invention in computer programming or hardware design, and the invention should not be construed as limited to any one set of computer program instructions.

Further, a skilled programmer would be able to write such a computer program or identify the appropriate hardware circuits to implement the disclosed invention without difficulty based on the flow charts and associated description in the application text, for example. Therefore, disclosure of a particular set of program code instructions or detailed hardware devices is not considered necessary for an adequate understanding of how to make and use the invention. The inventive functionality of the claimed computer implemented processes will be explained in more detail in the following description.

Further, certain steps in the processes or process flow described in the logic flow diagram must naturally precede others for the present invention to function as described. However, the present invention is not limited to the order of the steps described if such order or sequence does not alter the functionality of the present invention. That is, it is recognized that some steps may be performed before, after, or in parallel other steps without departing from the scope and spirit of the present invention.

Referring again to FIG. 25, Step 2501 is the first step in the process 2500 for monitoring oxygenation levels of a compartment according to one exemplary embodiment of the invention. In step 2501, a compartment sensor 405 may be manufactured from sterile materials as described above in connection with FIG. 21. Alternatively, a compartment sensor 405 can be encapsulated with sterile materials so that it can be used in a surgical environment or so that it can be place adjacent to wounds (or both).

In step 2503, a central scan depth marker 415 can be provided on a compartment sensor 405. In step 2506, an alignment mechanism 410 can also be provided on the compartment sensor 405 to allow a medical practitioner to orient a sensor 405 along a longitudinal axis of a compartment of interest.

In step 2509, an expansion device 535 may be provided between two or more grouped compartment sensors 405 as illustrated in FIG. 5A. In step 2512, the processor and display device 420 may receive input from a user on the type of compartment that is to be monitored by the inventive system 400.

In step 2515 and in response to the input of step 2512, the display device 420 can display a location of the selected compartment of interest such as illustrated in FIG. 14D. The display device 420 can also display the longitudinal axis 450 of the compartment of interest. Next, in step 2518, the display device 420 may display an ideal or optimal position for the compartment sensor 405 along the longitudinal axis of the compartment of interest as illustrated in FIG. 14D.

In step 2521, with the information from steps 2515-2518, the medical practitioner can identify a proper position of the compartment sensor on a patient through orienting the alignment mechanism 410 with the longitudinal axis of the compartment and by using the central scan depth marker 415.

In step 2527, the compartment sensor 405 can be placed on the patient. In step 2530, the compartment sensor can obtain a skin pigment value of the patient's skin through using a skin sensor 1820 as illustrated in FIG. 18C or thorough using a shallow sensor 405 as illustrated in FIG. 17. In step 2533, the processor 420A can determine an oxygenation offset value based on the skin pigment value obtained in step 2530.

Next, in step 2536, the offset value from step 2533 can be used during oxygenation level monitoring. In step 2539, the blood pressure of the patient can be monitored with a probe 440 and blood pressure monitor as illustrated in FIGS. 4 and 19. In step 2542, the system 400 can monitor the oxygenation levels of one or more compartments of interest over time. In step 2545, the system 400 can also monitor the oxygenation levels of healthy compartments to obtain a baseline while monitoring the compartments adjacent to an injury or trauma as illustrated in FIG. 15B.

In step 2547, the oxygenation levels of compartments of interest can be displayed on the display device 420 as illustrated in FIGS. 10, 14C, 15B-C, 16, and 20. In step 2550, the blood pressure of the patient can also be displayed on the display device as illustrated in FIG. 20. In step 2553, the display device 420 and its processor can monitor the relationship between the blood pressure values and oxygenation levels as illustrated in FIG. 20.

In step 2556, the display device 420 can activate an alarm in the form of an audible or visual message (or both), when the oxygenation levels drop below a predetermined value or if a significant change in the levels is detected as illustrated in FIG. 20. In step 2559, the display device can also activate an alarm in the form of an audible or visual message (or both), when both the oxygenation levels and blood pressure drop simultaneously or if one of them falls below a predetermined threshold value as described in connection with FIG. 20.

In step 2562, the display device 420 and its processor can increase a frequency of data collection for oxygenation levels and blood pressure values if both values drop. The exemplary process then ends.

ALTERNATIVE EXEMPLARY EMBODIMENTS

The inventive compartment monitoring system 400 could also be used for free flap as well as tissue transfer monitoring. Currently skin color and capillary refill are used to evaluate flap viability. This practice requires repeated examinations and subjective criteria. The conventional method requires leaving skin exposed or taking down dressings which can be very labor intensive. As a solution to the conventional approach, a sensor 405 can be sterilized and it can record average oxygenation levels over time. The sensor 405 can be placed on the flap (free or transferred).

The compartment sensor 405 can also be used to monitor oxygenation of tissue transferred for vascular patency. Specifically, for hand or any upper extremity surgery, the compartment sensor can be used to monitor the progress of revascularization of fingers, hands and arms based on measured oxygenation levels. The sensor 405 can be applied to the injured extremity once vascular repair has been performed in order to continue monitoring of vascular repair. A baseline of a corresponding uninjured or healthy extremity can be made once repair to the injured extremity is done—before closure—in order to get a baseline value while looking at the repair. Sensors 405 for this application will also need to be sterilized and be able to conduct scans with depths of at least 0.5 centimeters.

Figure 26:
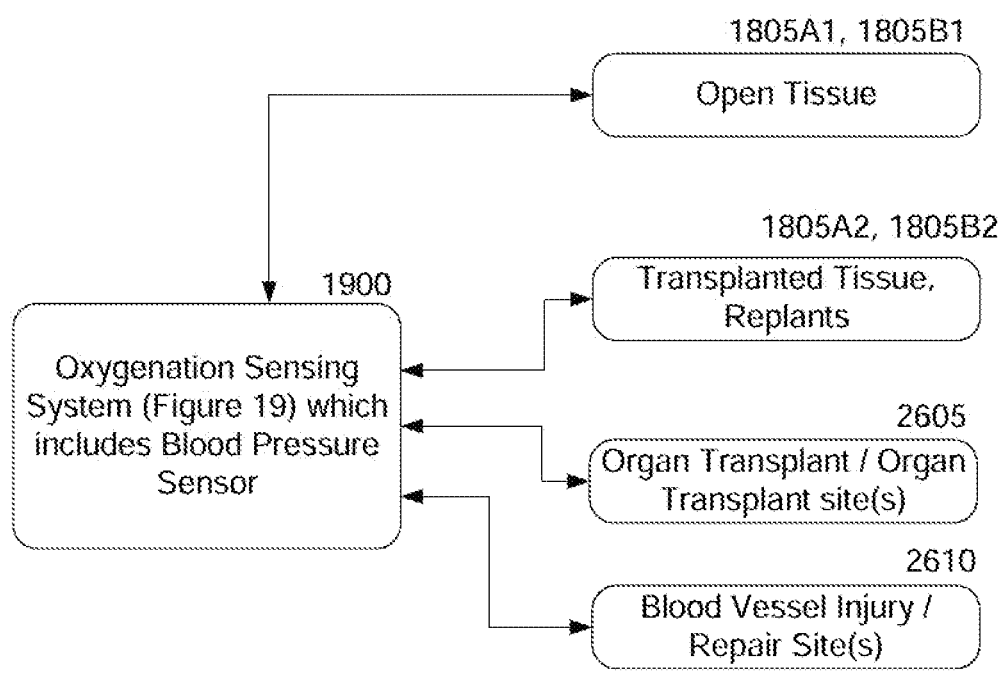
FIG. 26 is a functional block diagram illustrating additional applications of and Oxygenation Sensing System of FIG. 19 such as in Wound Management/Monitoring/Healing according to one exemplary embodiment of the invention.

Referring now to FIG. 26, this Figure is a functional block diagram illustrating additional applications of and Oxygenation Sensing System 1900 of FIG. 19 such as in Wound Management/Monitoring/Healing according to one exemplary embodiment of the system.

Other applications of the Oxygenation Sensing System 1900 include, but are not limited to, the following:

Traumatized Tissue 1805A1, 1805B1 Management/Monitoring/Healing of FIG. 26

In this exemplary application of the oxygenation sensing system 1900, the properties of traumatized tissue 1805A1, 1805B1 will be taken into account by the oxygenation sensing system 1900. One of ordinary skill the art recognizes that traumatized tissue 1805A1, 1805B1 does not have the same qualities as uninjured tissue: Injured tissue may become hyperperfused along with an elevated temperature. Bleeding may be present as well as other physiological alterations. One of ordinary skill the art recognizes that the physiological state of tissue is very different in injured tissue or diseased tissue. Since the body cannot differentiate between unplanned trauma (an accident) versus planned trauma (surgical intervention), this concept includes post surgical tissue.

Injured tissue often becomes a "Privileged" area relative to other healthy body parts in that the body will typically maintain increased perfusion over other areas that are not injured even in times of poor global perfusion (hypotension). The oxygenation sensing system 1900 may be designed to accommodate or to account for the different physiological states of injured or traumatized tissue 1805A1, 1805B1.

Specifically, predetermined or pre-programmed algorithms in the oxygenation sensing system 1900 may be used in the setting and monitoring of traumatized or wounded tissue. The oxygenation sensing system 1900 may track an Erythema index, temperature, or other modalities or any combination of factors, which can help differentiate traumatized tissue versus non-traumatized tissue. The oxygenation sensing system 1900 may be designed to anticipate certain characteristics for tissue monitoring depending upon the state of the tissue such as whether the tissue has been injured or has not been injured (traumatized/non-traumatized tissue). Alarms 1907 of the oxygenation sensing system 1900 may be set based on the type of tissue being monitored.

The sensors 405 of the oxygenation sensing system 1900 may be sterilized in order for use during evaluation of open wounds, such as illustrated in FIG. 21. The oxygenation sensing system 1900 may be used to conduct an initial evaluation in perfused tissue (that may include, but is not limited to, muscle, skin, soft tissue, and/or organs). The oxygenation sensing system 1900 can aid in determining what should be debrided (dead tissue—not perfused) versus what is viable tissue.

The oxygenation sensing system 1900 can also help identify tissue with adequate microcirculation (Capillaries, arterioles & veinules). This is especially beneficial in the evaluation of mangled extremities and for determining if an extremity is salvageable. The oxygenation sensing system 1900 may also help with determining if amputations are indicated or if attempted salvage should be considered. The oxygenation sensing system 1900 may assist in the assessment of vascularity of the extremity large vessels and small vessel perfusion. The oxygenation sensing system 1900 may detect devitalized tissue, which when allowed to persist, may become a nidus for infection. One of ordinary skill in the art recognizes that it is important to debride all dead/devitalized tissue to prevent or minimize the risk of infection.

The readings from oxygenation sensing system 1900 may indicate whether a limb and/or tissue is perfused and has the ability to heal. One of ordinary skill in the art recognizes that healing is generally based on the ability of the tissue to obtain nutrients from the blood that is perfused throughout any given tissue.

Transplanted Tissue/Flaps Management/Monitoring/Healing 1805A2, 1805B2

For Transplanted Tissue/Flaps Management/Monitoring/Healing, each sensor 405 of the oxygenation sensing system 1900 usually must be sterile to allow placement during a surgical procedure. Each sensor 405 may be placed over the anastomosis (connection of two or more ends of a vessel as in a repair of an artery or vein) in order to get a direct read on tissue around the connection of the arteries & veins that supply the transplanted tissue.

The placement of a sensor 405 at distal tips of tissue allows for monitoring of the most sensitive tissue for tracking poor perfusion and/or necrosis. These areas are call "watershed" areas where the tissue is at most risk for compromised perfusion. The oxygenation sensing system 1900 may allow for early warnings of decreased perfusion. Each sensor 405 of the oxygenation sensing system 1900 may be placed on tissue during a procedure once vessels are anastomosed. An initial reading from each sensor 405 may be determined in the operating room in order to obtain a baseline reading. Since the body cannot differentiate traumatized tissue from "surgical trauma" performed by a surgeon, the tissue characteristics are similar to traumatized tissue and would be expected to have similar findings and values. Post surgical tissue should have a "privileged" state of increased perfusion to promote healing.

Usually, each sensor 405 of the oxygenation sensing system 1900 is maintained in the same position over the transplanted tissue in order to monitor the vascular flow to the transplanted tissue. If the NIRS values detected by each sensor 405 start to decrease past a certain threshold, an alarm, such as the audible alarm 1907, may be activated in order to warn the medical practitioner that the flap or transplanted tissue is threatened.

If a signal of a sensor 405 from the oxygenation sensing system 1900 is lost (such as during hematoma formation) an alarm, such as the audible alarm 1907, is signaled. The oxygenation sensing system 1900 can help detect an anastomosis rupture or thrombosis (blockage). Early detection can allow for early intervention such as anastomosis repair or canulation to prevent flap/graft failure due to extended lack of perfusion/ischemia. One of ordinary skill in the art recognizes that an Anastomosis rupture can cause death of the transferred tissue as well as patient death through exsanguination if not diagnosed and treated early and accurately. A sentinel bleed is a small bleed at the site of anastomosis that typically is small in nature but is indicative of vessel rupture or disruption. If the vessel is large and the patient is on anticoagulation (typical), the blood loss can be significant and ultimately lead to exsanguination. Bleeding that may occur below the skin may be detected with oxygenation sensing system 1900 and is usually not detectable by medical practitioners in a timely manner. Additionally, hematoma detection through signal loss could play a role in early detection.

The oxygenation sensing system 1900 may detect three common ways transplanted tissue 1805A2, 1805B2 fails: A) Arterial clot/rupture. Such an event usually causes decreased oxygenation due to lack of new blood with oxygen being brought into the transplanted tissue. B) Venous occlusion/ clot. Poor outflow from transplanted tissue may usually result in venous engorgement and an overall drop in tissue oxygenation due to increased venous blood (deoxygenated) present in the tissue. C) Hematoma development (which is usually due to a vessel rupture) can potentially cause a loss of signal, which may be an event for oxygenation sensing system 1900 to activate an alarm, such as audible alarm 1907.

Another application for oxygenation sensing system 1900 includes the monitoring of the transfer of tram flaps and tissue 1805A2, 1805B2. For these applications, the sensors 405 should be sterilized so that they can be positioned on the site of interest very early after the procedure to obtain an initial reading on the operating room (OR) table. The oxygenation sensing system 1900 may provide data that quantitatively measures oxygenation of transferred tissues.

The oxygenation sensing system 1900 may sense conditions for organ transplant 2605 monitoring. Typically, a host versus graft reaction will generally cause an immune response in a patient to vascular supply affecting the vascular flow to the organ. Poor perfusion which can possibly be combated with additional immune suppression may also be detected by oxygenation sensing system 1900. The oxygenation sensing system 1900 may detect conditions that allow for early surgical intervention for revisions if needed/ possible.

The Oxygenation sensing system 1900 may also be used to revascularize tissue due to chronic vascular insufficiency 2610. The oxygenation sensing system 1900 may be able to manage/monitor/and/or promote healing of revascularized tissue. The oxygenation sensing system 1900 may detect conditions related to bypass graft patency. With bypass graft patency, chronic poor tissue perfusion of distal extremities (typically the lower extremity) can be treated by bypassing poor vasculature with a biological or synthetic graft to restore blood flow to distal tissue. Specifically, poor large vessel perfusion 2610 is bypassed to allow for an adequate supply of blood to distal tissue as understood by one of ordinary skill in the art. Any anastomosis can be monitored with a sensor 405 to insure the vessel connection is intact and functioning correctly and remaining open.

The oxygenation sensing system 1900 may promote extremity healing in chronic disease conditions. For example, diabetes usually causes peripheral vessel disease resulting in the need for extremity (typically foot/leg) amputation. Other autoimmune and vasculitis are other medical conditions which can also cause poor perfusion in extremities. One of ordinary skill in the art recognizes that wounds do not heal if they are poorly perfused. Each sensor 405 can be used to determine the ability of the tissue to heal in order to determine the level of amputation. This application is similar to the use in the traumatized/mangled extremity and determining what injured tissue to debride versus what to save.

The oxygenation sensing system 1900 may also monitor tissue replantation 1805A2, 1805B2. Specifically, the system may monitor the status of reattaching tissue that has been traumatically amputated. For example, such tissue may include, but are not limited to, fingers, hands, arms, feet or legs. The oxygenation sensing system 1900 may help a medical practitioner monitor anastomosis integrity and distal flow. Specifically, the oxygenation sensing system 1900 may help a medical practitioner monitor anastomosis of both arterial inflow and venous outflow. One of ordinary skill in the art recognizes that replants can fail if not provided with adequate outflow. Replantation typically requires two veins to one artery to allow for adequate blood flow in and out of the replant area.

The oxygenation sensing system 1900 may be useful in monitoring vessel injuries and/or vessel repairs 2610. Such injuries may include, but are not limited, to a laceration to a major arterial supply and/or extremity/organ. One of ordinary skill in the art recognizes that reperfusion can cause tissue death or compartment syndrome due swelling once blood flow is restored to the tissue. The oxygenation sensing system 1900 may provide data that allows for post operative/ repair monitoring similar to the transplant of tissue as discussed above and the system can insure the vessel repair is adequate and remains open. Each sensor 405 of the oxygenation sensing system 1900 can also monitor tissue pressure to diagnose acute compartment syndrome due to reperfusion injury.

The oxygenation sensing system 1900 can also assist with collecting data to help a medical practitioner to decide what is the appropriate treatment for a given tissue region. The oxygenation sensing system 1900 may also assist the medical practitioner with determining if a selected procedure has been completed successfully. For example, with a fasciotomy, uninformed or unfamiliar medical practitioners can fail to release all compartments. Meanwhile, one of ordinary skill in the art recognizes that a complete release of all compartments allows for restoration of hyperemia and return of blood flow. An inadequate release from a fasciotomy can occur if the fascia is not released proximal and distally enough or if skin is not released in some cases. A percutaneous release may lead to incomplete release. During and after the fasciotomy, the oxygenation sensing system 1900 may be able to detect hyperemia. If the treated region does not become hyperemic, then such a condition may be a sign of incomplete release or lack of release (missed the compartment) from the fasciotomy. Additionally, if the fasciotomy is performed too late, the tissue may be dead already. In this case, a lack of return of blood flow would indicate to the surgeon the need for debridement to prevent infection.

Another procedure in which oxygenation sensing system 1900 may also assist the medical practitioner to determine if a selected procedure has been completed successfully is revascularization 2610. The oxygenation sensing system 1900 may detect if restoration of blood flow has been achieved for a particular site. Hyperemia is expected once blood flow is restored due to a reperfusion effect. The oxygenation sensing system 1900, as noted above, can detect hyperemia for a particular region. Additionally, the system could be used to determine if the bypass is sufficient to restore flow or if additional measures need to be taken.

The oxygenation sensing system 1900 may also help a medical practitioner to determine the success of a bypass surgery. The oxygenation sensing system 1900 may detect if a bypass anastomosis is present and if adequate blood flow downstream relative to the bypass region has been restored. The oxygenation sensing system 1900 may determine if the operated vessel is open and if any related extremity is receiving adequate blood flow.

The oxygenation sensing system 1900 may also help a medical practitioner to quantitatively measure the success of operations related to: reperfusion injury; ACS; transplanted tissue 1805A2, 1805B2; replantation 1805A2, 1805B2; and the like. For transplanted tissue 1805A2, 1805B2, the oxygenation sensing system 1900 may detect anastomosis and provide data that indicates whether the transplanted tissue is healing and not dying. For operations related to replantation 1805A2, 1805B2, the oxygenation sensing system 1900 may provide data to indicate whether blood flow is restored to a severed limb. The oxygenation sensing system 1900 may also provide data to indicate whether a vessel injury and its related repair have been successful. Specifically, the sensors 405 can measure oxygenation of replanted tissue. Exemplary depths in which the sensors 405 can scan include, but are not limited to, depths of about one centimeter or even less (such as for fingers).

For reperfusion injuries, the oxygenation sensing system 1900 can provide reperfusion monitoring. The oxygenation sensing system 1900 can monitor initial hyperperfusion and may provide data to indicate if perfusion has increased or decreased for a particular tissue region.

The oxygenation sensing system 1900 may be used to detect other conditions such as Exertional Compartment Syndrome (Chronic) caused by exercise or other types of physical activities. For detecting this condition, the sensors 405 can be the same as those used to detect ACS in injured tissue. For exertional compartment syndrome, the regions of interest will most typically be in the legs or forearms of the patient. The oxygenation sensing system 1900 may be used to detect conditions in highly trained and conditioned athletes. The oxygenation sensing system 1900 may be provided with a base algorithm that compares highly trained athletes compared to recreational athletes and untrained individuals.

The base algorithm for the oxygenation sensing system 1900 for detecting exertional compartment system should account for the different physiological conditions associated with exercising. The oxygenation sensing system 1900 may require readings for pre-exercise, intra-exercise, and post-exercise to properly calibrate the algorithm. The algorithm may take into account that unlike ACS, exertional compartment syndrome may be present in an environment in which muscles swell with blood and have increased metabolites. These differences between ACS and exertional compartment syndrome may usually be accounted for in the base algorithm for oxygenation sensing system 1900.

The sensors 405 for detecting exertional compartment syndrome may have a placement similar to the placement used to detect ACS. However, the sensors 405 may be provided with additional mechanical features such as, but not limited to, additional cord length, spring biased cords, etc. to allow for activities like jogging and/or marching by the patient. Other mechanical features may include, but are not limited to, additional adhesive or straps positioned on sensors 405 to insure adequate sensor skin connection. Additionally, the sensors could be attached to a mobile unit that allows for monitoring while covering large distances. Further, the sensors 405 may be positioned within a sleeve 3710 for accurate sensor placement that will not allow for movement of the sensors 405 relative to the region of interest, as illustrated in FIG. 37. The sensors 405 and their mechanical features may be designed to function properly in the presence of exercise by-products such as sweat from the human body during the physical exertion of the patient being monitored with the oxygenation sensing system 1900. Additionally, the sleeve 3710 or attachment device should not cause changes in flow due to excessive compression.

Sensors could be used in a wireless fashion or only record data to be analyzed once plugged into a monitor system after training is complete. A memory device can record data then be retrieved later in order to limit the size and weight of the monitoring system.

This concept can be carried over into athletic or military training to guide optimization of physical training without exceeding the tolerance of the muscle. A mobile unit or one placed in a backpack or other carrying device could guide intensity of workouts and training, For detecting exertional compartment syndrome, the oxygenation sensing system 1900 may be provided with features for reducing or eliminating noise from the movement of the sensors 405. For example, the oxygenation sensing system 1900 may be provided with software and/or hardware to implement noise reduction algorithms caused by physical movement of the sensors 405. In the exertional compartment syndrome monitoring scenario erythema/pigment monitoring may not be evaluated since it is unlikely that the tissue of interest is traumatized. However, other chemical and environmental factors (such as but not limited to pH and temperature) may affect the local tissue.

The oxygenation sensing system 1900 may provide data that helps a medical practitioner to assess tissue viability. The oxygenation sensing system 1900 may be used to monitor superficial trauma on patients. The oxygenation sensing system 1900 may replace the prior art black lamps which have been used in the past for evaluating tissue perfusion. Prior art devices are typically intrusive and bulky and are not passive solutions for monitoring and testing perfusion.

Oxygenation sensing system 1900 may also provide a guide to a medical practitioner for amputation procedures. The oxygenation sensing system 1900 may be useful for patients with diabetes and who may need amputation of a limb due to complications arising from this disease. The oxygenation sensing system 1900 may determine a level of amputation for adequate blood flow in lower extremity ulcers/infected regions. In other words, the oxygenation sensing system 1900 can help the medical practitioner determine a level or the "line" to draw for amputating a limb. The oxygenation sensing system 1900 allows a medical practitioner to determine at what level of a limb will heal due to the detection of adequate blood flow by the sensors 405 positioned on the limb of interest. In this monitoring for detecting the level of amputation, the position of the sensors 405 can be similar to those used for detecting compartment syndrome to evaluate muscle. Sensors 405 designed for shallow scans may be used to monitor skin values.

Referring to FIG. 32, this figure is logic flow diagram illustrating an exemplary method 3200 for assessing tissue conditions to assist medical practitioners in determining an amputation "line" according to one exemplary embodiment of the invention. This method describes steps that can be used with either the oxygenation sensing system 1900 or the combined system 2700 as discussed below.

Step 3205 is the first step in the process 3200 in which baseline oxygenation values for a cross-section of the population of patients with a common medical trait and/or condition are identified. For example, baseline oxygenation values may be established for patients having diabetes. Oxygenation values may be taken from several patients having diabetes and having a need for amputation of an extremity.

A minimum oxygenation value may be determined from this population of patients that indicates healthy tissue compared to tissue that may need to be the debrided or amputated. One of ordinary skill in the art recognizes that the invention is not limited to patients having diabetes. The invention may address any population of patients having a common medical trait and/or condition such as a disease so that a baseline level of oxygenation values may be established for the patients having a common medical trait and/or condition and who need amputation of an extremity.

Next, in step 3210, the oxygenation sensors 405 may be applied along a length of an extremity that may require amputation. The sensors 405 should be positioned along tissue which is healthy as well as along tissue which will likely need amputation.

In step 3215, the oxygenation sensing system 1900 monitors all the sensors 405 positioned along the length of the extremity. Subsequently, in step 3220, the oxygenation sensing system 1900 displays NIRS values for the sensors 405 positioned along the length of the extremity.

In step 3225, the oxygenation sensing system 1900 compares NIRS values between the respective sensors 405 positioned along the length of the extremity. Next, in step 3230, the oxygenation sensing system 1900 identifies sensors having relatively low values based upon the comparison made among the line of sensors 405. In step 3235, the oxygenation sensing system 1900 compares the values from the sensors 405 to the baseline established for the patients having a common medical trait and/or condition.

In step 3240, the oxygenation sensing system identifies the sensors 405 which have NIRS values that correspond to the baseline set of values that indicate amputation may be needed for an area of tissue. Next, in step 3245, the oxygenation sensing system 1900 displays visuals identifying sensors 405 that may correspond to the amputation "level" or "line" on the extremity of the patient. The process then ends.

The oxygenation sensing system 1900 may also be used to monitor organ perfusion 2605. Such monitoring is beneficial for operations relating to organ transplantation. The oxygenation sensing system 1900 may be used to help a medical practitioner assess acute grafts and to determine if the host body has rejected the transplantation. The oxygenation sensing system 1900 may also monitor abdominal compartment syndrome as well as the perfusion of internal organs such as, but not limited to, the kidneys, liver, spleen, and bowel (small & large intestines).

The oxygenation sensing system 1900, especially the sensors 405, may be adapted or designed for specific body types, such as obese individuals having layers of fatty tissue. Problems could arise if sensors 405 with normal scan depths designed for normal body types (having nominal fatty layers) are used for monitoring obese individuals. Different scaled sensors 405 having deeper scan depths may be provided for obese individuals due to excess layers of skin and fat tissue that are normally present with obese body types.

The oxygenation sensing system 1900 may help determine if skin ready for surgery 1805A1 such as for a pilon fracture. A pilon fracture is a comminuted fracture of the distal tibia. The fracture usually includes a long oblique fracture extending medial to lateral as well as a fracture extending to the tibiotalar articular surface. It results from an axial loading injury, with impaction of the talus upon the tibial plafond.

Current methods prior to treating a pilon fracture require a medical practitioner to estimate if swelling has decreased enough to allow for healing (i.e., such as if the skin has wrinkles). This prior art subjective judgment of the medical practitioner can now be replaced with sensors 405 which may help determine if skin is well perfused and not stretched too tight. The oxygenation sensing system 1900 may be used in the operating room (OR) to determine if skin closure is too tight and if it is not allowing adequate blood flow to tissue to allow for healing. This data from the oxygenation sensing system 1900 will allow the medical practitioner to quantitatively determine if the wound should be left open to heal.

The oxygenation sensing system 1900 can generally help a medical practitioner to monitor skin perfusion. The oxygenation sensing system 1900 may be used at the time of an attempted closure and it may help prevent skin/wound complications and dehiscence. The oxygenation sensing system 1900 may help to detect if good blood flow is present for wound healing. Current, conventional methods for assessing good blood flow require human observations to determine if skin is wrinkling.

The oxygenation sensing system 1900 may be used to help a medical practitioner determine if a patient is experiencing hypotension and/or Shock 2605 or anemia. The oxygenation sensing system 1900 may be used in an emergency room, an intensive care unit (ICU), or an operating room (OR). If the oxygenation system 1900 detects decreasing NIRS values, then the combined system 2700 may determine that these decreasing NIRS values are likely due to lower serial hemoglobins (Hgb) or hematocrits (Hct). Table 6 provided and discussed below provides just one example of how certain conditions of a patient may indicate the presence or existence of hemorrhaghic shock or anemia.

The oxygenation sensing system 1900 may be designed to allow for comparable values across a variety of patients by utilizing adjusted values. For example, short monitoring of tissue may sometimes provide raw values from the oxygenation sensing system 1900 that may be very erratic and vary widely. However, continual monitoring with the oxygenation system 1900 may provide a baseline and allow a medical practitioner to adjust for values after the baseline is established. The oxygenation system 1900 may have off-set values that may adjust readings for variations of skin pigment, erythema, age, vasculature status, respiratory status, demographics, tobacco use, and cardiac/health risks.

In summary, the oxygenation sensing system 1900 may comprise one or more algorithm(s) to account for different variations in person being monitored in order to get an "adjusted value" that can be compared across individuals of different skin color, age, weight, sex, and/or injury status. The oxygenation system 1900 may also establish predetermined threshold values for normal perfusion, hypoperfusion, as well as values that assess viable tissue versus nonviable tissue. Additionally, the assessment of the patient such as but not limited to the American Society of Anesthesiology (ASA) physical status classification could be built into the algorithm to allow for warnings earlier in higher risk individuals.

Figure 27:
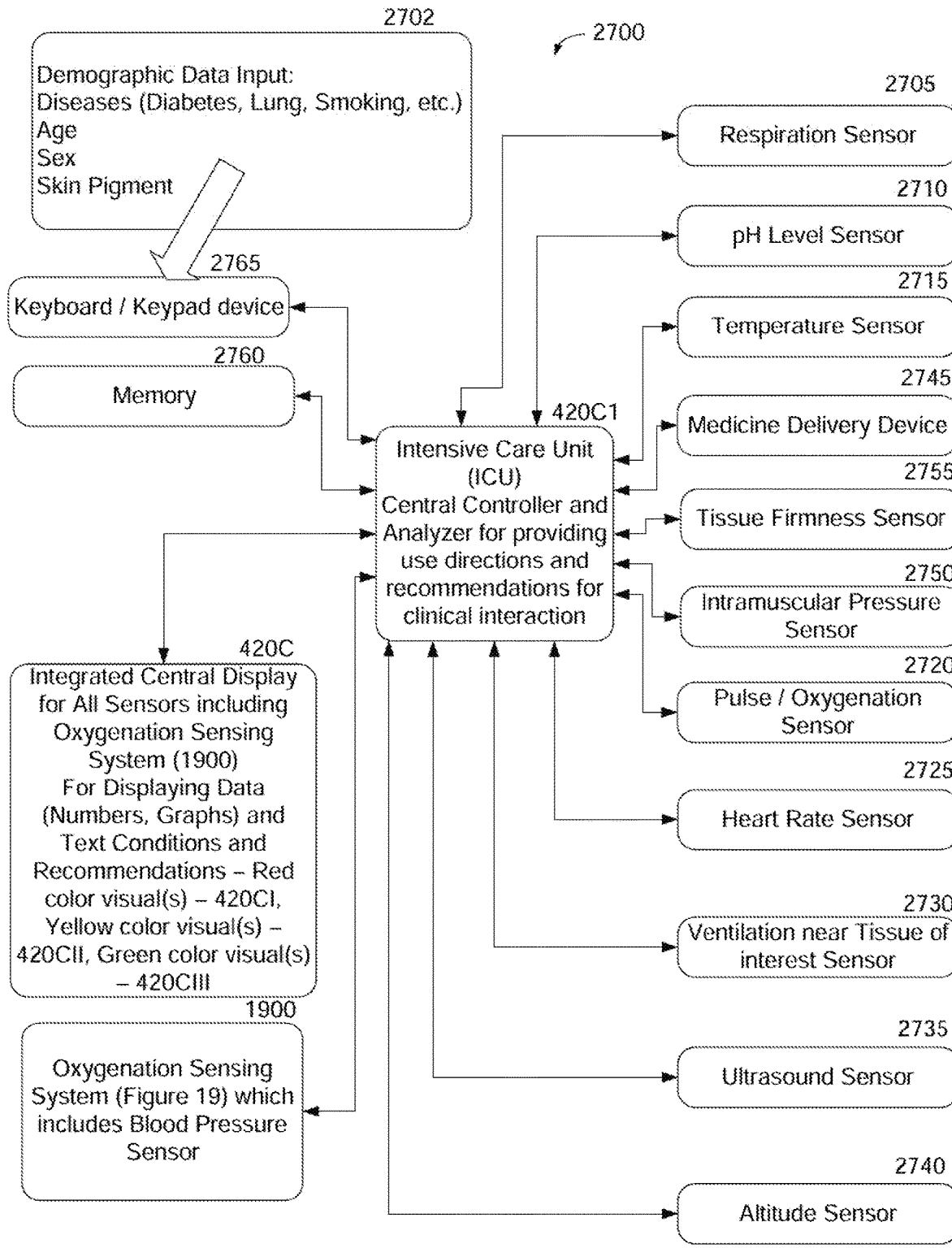
FIG. 27 is a functional block diagram of an intensive care unit (ICU) central controller and analyzer according to one exemplary embodiment of the invention.

Referring now to FIG. 27, this Figure is a functional block diagram of an intensive care unit (ICU) central controller and analyzer 420C1 according to one exemplary embodiment of the inventive system. According to this exemplary embodiment, the oxygenation sensing system 1900 described in FIG. 19 can be made to be compatible with an ICU central controller 420C1 which may be coupled to other sensors and systems.

For example the ICU central controller 420C1 may be coupled to a respiration sensor 2705, a pH level sensor 2710, a temperature sensor 2715, a pulse oxygenation sensor 2720, a heart rate sensor 2725, a ventilation sensor 2730, an ultrasound sensor 2735, and an altitude sensor 2740 as well as a monitor to determine pressure on the injured area under the dressings. The ICU central controller 420C1 can provide directions on use of its system components. The ICU central controller 420C1 may have analyzing hardware or software or both for providing recommendations for clinical interventions based on the data it collects from the various sensors as well as data 2702 that may be entered via keyboard 2765 by an operator that is specific to a patient. The ICU central controller 420C1 may provide its directions, data, and recommendations on a display device 420C.

In another exemplary embodiment, the ICU central controller 420C1 can be part of an existing sensor system such as a heart rate and/or respiratory monitoring system. According to such an exemplary embodiment, the oxygenation sensing system 1900 would be designed to be compatible with the ICU central controller 420C1 with the appropriate hardware and/or software (i.e. compatible connector, compatible application programming interfaces—APIs, etc.).

The system 2700 may provide a complete ACS smart device that combines monitoring, diagnosing, and treating up to fasciotomy. The system 2700 may intelligently combine all known technology and data to provide medical practitioners with guidelines. The system 2700, and particularly its oxygenation sensing system 1900, may obtain NIRS values and interpret them based on trends in values.

The central controller 420C1 may function as a data collection device which obtains data from ICU devices. The central controller 420C1 may obtain directly blood pressure (BP), pulse ox, lab values, demographic data and may replace an ICU monitor.

The combined system 2700 may include an intramuscular pressure device 2750 for monitoring muscle pressure and for filtering exudates. The intramuscular pressure device 2750 may comprise an ultrafiltration catheter for pressure reading and a fluid removal system.

The combined system 2700 may further comprise a medicine delivery system 2745 that may operate in a manner similar to a drip line setup found in an ICU that would automatically administer medication to affect cardiovascular status. The medicine delivery system may administer drugs such as, but not limited to, pressors to increase blood pressure to allow for elevated perfusion pressures. The system 2700, via medicine delivery system 2745, may administer medicines automatically based on monitored conditions. For example, if the system 2700 via the oxygenation sensing system 1900 detects decreasing NIRS values, then the central controller 420C1 could issue a command to the medical delivery system 2745 to administer a pressor. The medical delivery system 2745 may comprise a small pump for moving liquid medicines into a patient. This system could deliver medicines or other entities such as but not limited to intravenous fluid boluses or blood products.

The combined system 2700 may also comprise a tissue firmness device 2755 to measure how firm an extremity is and to determine how tense the extremity is. The ability to compress the tissue is a subjective measurement clinicians use to assess injured extremities. As noted previously, the combined system 2700 may also include an ultrasound sensor 2735. The ultrasound sensor 2735 may measure the vibration or wave characteristics of the fascia. The data from each of the sensors of the combined system 2700 may be time stamped by the central controller 420C1 for review and archival purposes. The data may be stored in the memory device 2760 which can comprise volatile or non-volatile memory (or both).

Other Uses of a Combined System 2700 for Patient Monitoring and Medical Management Indications The combined system 2700 may incorporate the vital signs and NIRS values in order to give recommendations for clinical intervention. The combined system 2700 may also provide various levels of alarms for the medical practitioner. For example, the combined system 2700 may have a series of color-coded visual indicators to provide a relative status of different conditions for patient. According to one exemplary embodiment, the combined system 2700 may display a red color coded alarm display 420CI, a yellow color-coded alarm display 420CII, and a green color-coded alarm display 420CIII.

According to one exemplary embodiment, the red color-coded alarm display 420CI may indicate a danger condition such as low perfusion, or that NIRS and blood pressure are in phase or that NIRS values are demonstrating a decreasing trend. A yellow color-coded alarm display 420CII may indicate a moderate drop or downward trend with perfusion existing at minimal levels. This yellow alarm may also indicate that blood pressure and the NIRS values are beginning to become in phase. The combined system 2700, and particularly the central controller 420C1, may recommend considering other modalities to evaluate perfusion such as intracompartmental pressure measurements, pressors, and/or transfusions. Meanwhile, the green color-coded alarm display 420CIII may indicate that there are no signs of poor or below-normal perfusion levels.

The oxygenation sensing system 1900 of the combined system 2700 may activate an audible alarm 1907 or anyone of the visual alarms 420CI-CIII (any combination thereof) to indicate low blood pressure and decreasing NIRS values. The combined system 2700 may recommend transfusions, intravenous fluids, and/or pressors. In non-traumatized or traumatized patients the oxygenation sensing system 1900 could be placed on the leg 100 to monitor patient perfusion status. Poor cardiac function of a patient will usually cause decreased levels of perfusion. So the combined system 2700 may utilize the heart rate sensor 2725 in such situations for monitoring heart failure patients.

The respiration sensor 2705 may be used by the combined system 2700 to detect increased respirations as well as pH levels (elevated lactic acid typically is associated with lower respiratory alkalosis). The combined system 2700 by monitoring the respiration sensor 2705 in combination with the oxygenation sensing system 1900 may signal an alarm, such as the audible alarm 1907 or any one of the visual alarms 420CI-CIII (or any combination thereof), to increase oxygen supplementation or to recommend intubation for a patient.

The combined system 2700 may use the pH level sensor 2710 to detect changes in pH levels of the patient. A change in pH level of the patient in combination with a decrease in NIRS values detected by the oxygenation sensing system 1900 may cause the combined system 2702 signal alarm such as the audio alarm 1907 or a visual alarm 420CI (or both) to indicate the patient has poor resuscitation. Such a condition may typically be found in patients who have had a replacement of blood products after a large amount of blood loss due to an injury or because of surgery.

The intensive care unit 420C1 of the combined system 2700 may record vital signs detected by the heart rate sensor 2725 and the pulse/oxygenation sensor 2720 in a memory device 2760 coupled to the intensive care unit 420C1. The oxygenation sensing system 1900 may be designed so that it is compatible with programs of common intensive care units 420C1. If the oxygenation sensing system 1900 detects decreasing NIRS values in combination with changes in vital signs such as heart rate, blood pressure, and/or respiration, then the intensive care unit 420C1 indicate that tissue perfusion may be reaching a vulnerable point. When this vulnerable point is conveyed by the intensive care unit 420C1, then a medical practitioner may be required to intervene with the patient.

The combined system 2700 may also monitor and calculate if blood products are needed by a patient. Similar to serial hemoglobins (Hgb) or hematocrits (Hct), the NIRS values detected by the oxygenation sensing system 1900 may be used to monitor perfusion during or after surgery, such as after hip or knee replacements or other surgeries or trauma. If the oxygenation sensing system 1900 detects decreasing NIRS values, then the combined system 2700 may determine that these decreasing NIRS values are likely due to lower Hgb or Hct. The combined system 2700 may be designed to track transfusions given to the patient so that it may correlate if a particular transfusion increases the Hgb or Hct levels in a patient. According to this exemplary embodiment, the combined system 2700 becomes a noninvasive means of monitoring blood transport of oxygen in an intra or post-operation (post-op) setting.

During surgery or after surgery due to continued bleeding either under the skin or through a wound, a patient may lose a significant amount of blood that the patient becomes anemic. Typically, this condition is followed through serial blood draws that examine factors such as hemoglobin concentrations or hematocrits. Additional things such as lactic acid levels and other factors can also be examined. All these blood draws require needle sticks and can be difficult in sicker patients that have poor vascular systems. The ability of the oxygenation system would be to follow the values through a noninvasive means.

Opposite to traumatized tissue, non-traumatized tissue is not "privileged" and will have shunting of blood flow away from it to more vital organs such s the brain, heart and other vital organs. As a patient becomes anemic, the oxygenation in distal extremities will fall indicating a stressed condition. By correlating decreasing oxygenation values in the extremity or other areas of the body with decreasing Hct or Hgb a standardization and guideline can be determined which would alleviate the need for repeated lab draws. The reverse can also be said regarding the monitoring of oxygenation levels as blood products are replaced. An increase in oxygenation values would be expected as blood is replaced. The combined system 2700 may use predetermined tables such as Table 6 provided below in order to help make assessments about a patient. Table 6 provided below provides just one example of how certain conditions of a patient may indicate the presence or existence of Hemorrhagic shock and/or Anemia.

Shock is a state of inadequate perfusion, which does not sustain the physiologic needs of organ tissues. Many conditions, including blood loss but also including nonhemorrhagic states such as dehydration, sepsis, impaired autoregulation, obstruction, decreased myocardial function, and loss of autonomic tone, may produce shock or shocklike states. Hemorrhagic shock is a condition in which blood loss exceeds the body's ability to compensate and provide adequate tissue perfusion and oxygenation. This frequently is due to trauma, but it may be caused by spontaneous hemorrhage (e.g., gastro intestinal bleeding, childbirth), surgery, and other causes. Most frequently, clinical hemorrhagic shock is caused by an acute bleeding episode with a discrete precipitating event. Less commonly, hemorrhagic shock may be seen in chronic conditions with subacute blood loss.

In addition to helping a medical practitioner to determine shock in a patient, the combined system may also assist the medical practitioner with determining the existence of anemia. Anemia is a condition of the blood where there is not enough oxygen carried to the body's cells. Anemia usually occurs over a longer period of time compared to the suddenness of hemorrhagic shock. Shock occurs can occur within seconds or minutes while anemia generally occurs over hours and days and is systemic. Oxygen is mostly transported on hemoglobin molecules in red blood cells. Anemia is present when amounts of red blood cells and/or hemoglobin are below normal. The most common sign of anemia is fatigue. A patient may also feel weak, dizzy, or just not well. An anemic patient may become pale, feel cold and easily short of breath. The patient's blood pressure may become low and heart rate may become rapid.

Table 6 provides exemplary values, therefore, one of ordinary skill the art recognizes that other values/ranges within this table may be adjusted depending upon the subjective conditions of a particular patient and/or adjustments provided by one or more medical studies in the field.

By utilizing the values in Table 6, the combined system 2700 may help a medical practitioner formulate a proper diagnosis of the presence or existence of hemorrhagic shock or intra/post operative anemia.

TABLE 6

CLASSIFICATION OF HEMORRHAGIC SHOCK/ANEMIA

|  | Compensated (Anemia) | Mild (Anemia) | Moderate (Shock) | Severe (Shock) |
| --- | --- | --- | --- | --- |
| Blood Loss (mL) | ≤1000 | 1000-1500 | 1500-2000 | >2000 |
| Heart rate (bpm) | <100 | >100 | >120 | >140 |
| Blood pressure | Normal | Orthostatic change | Marked fall | Profound fall |
| Capillary refill | Normal | May be delayed | Usually delayed | Always delayed |
| Respiration | Normal | Mild increase | Moderate tachypnea | Marked tachypnea: respiratory collapse |
| Urinary output (mL/h) | >30 | 20-30 | 5-20 | Anuria |
| Mental status | Normal or agitated | Agitated | Confused | Lethargic, obtunded |

In addition to the conditions listed in Table 6 provided above, the combined system 2700 may include NIRS values detected by the oxygenation sensing system 1900 as part of a shock assessment. As apparent to one of ordinary skill the art and as illustrated in the several figures, the location of measurement for the shock assessment can vary. For example, the location of measurement may include, but is not limited to, the arm, leg, foot, hand, torso, abdomen, buttock, and/or multiple sites, such as illustrated in FIGS. 13A, 13B so that the medical practitioner may have different options based on the local effects of trauma to the tissue at a particular site on the patient.

One of ordinary skill in the art will appreciate that injury to tissue causes the injured tissue to become "privileged"

with increased blood flow to the injured area at the expense of non-injured areas. This means that the medical practitioner may have a need to monitor multiple locations of the patient since the injured area being monitored may have abnormally high readings and may not be responsive to global body perfusion changes. For example, an injury or operation to the leg may cause increased values in the injured area (leg) which may be resistant to global changes since the normal response is to shunt blood to the injured area to promote healing. Therefore, a different location than the injured site is required to monitor the global hematologic status of the body, such as perhaps the arm or contralateral leg. The monitoring site needs to reflect the changes in the body's hematologic status, which would not be the case in a "preferred" location such as a site of injury.

Figure 33A:
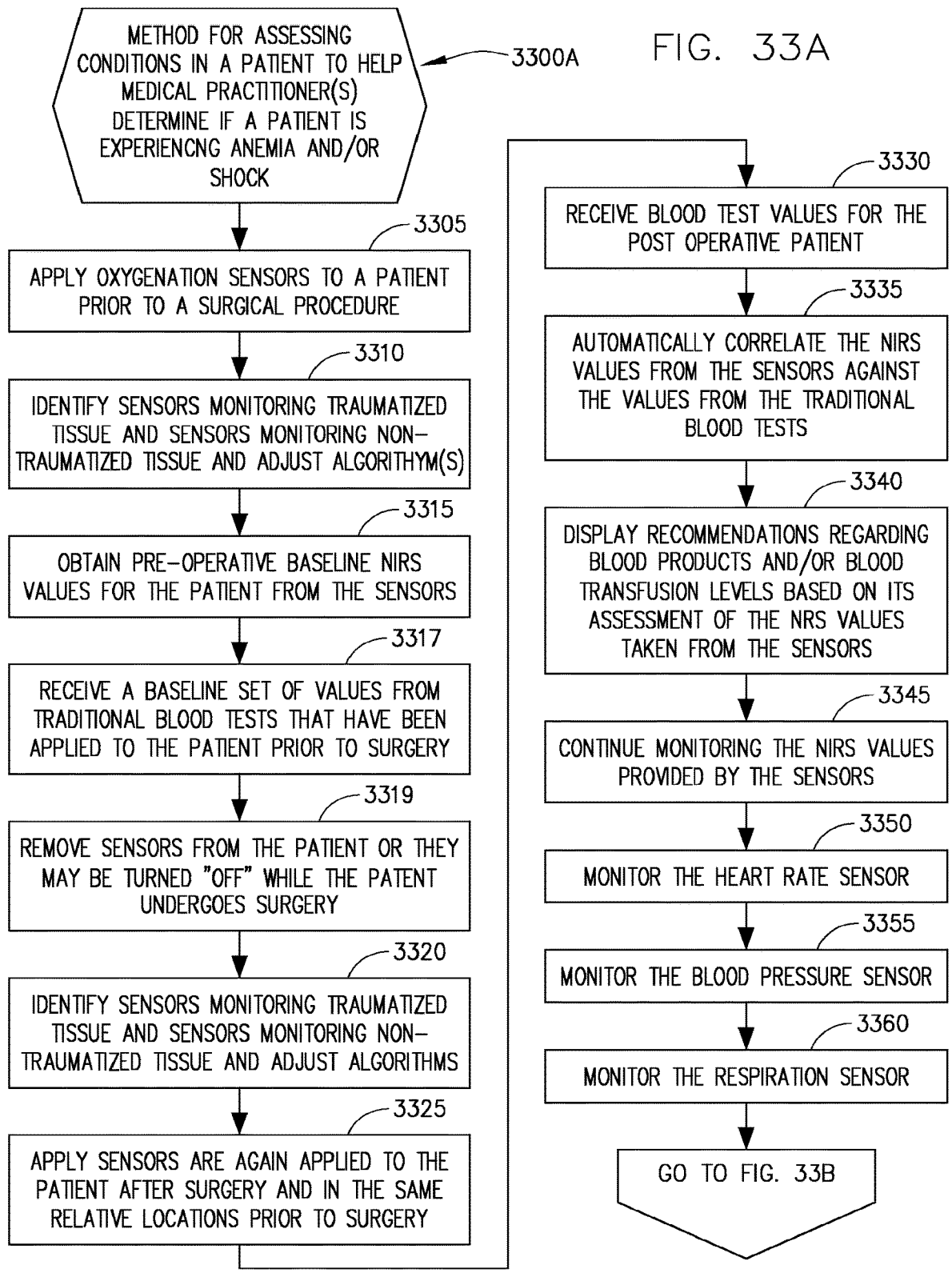

Referring to FIG. 33A, this figure is logic flow diagram illustrating an exemplary method 3300 for assessing conditions in a patient to help medical practitioners determine if a patient is experiencing anemia and/or shock according to one exemplary embodiment of the invention. The method 3300 also provides a non-invasive way to determine if a patient needs additional blood products and/or transfusions. This method 3300 describes steps that can be used with the combined system 2700 as discussed above.

Step 3305 is the first step in the process 3300 the oxygenation sensors 405 are applied to a patient prior to a surgical procedure. In step 3307, which is similar to steps 2860 and 3060, the medical practitioner may identify which sensors 405 are monitoring healthy or "non-traumatized" tissue and which sensors 405 are monitoring traumatized tissue. As noted above with respect to FIG. 26, injured tissue often becomes a "Privileged" area relative to other healthy body parts in that the body will typically maintain increased perfusion over other areas that are not injured even in times of poor global perfusion (hypotension). The oxygenation sensing system 1900 and/or combined system 2700 may be designed to accommodate or to account for the different physiological states of injured or traumatized tissue 1805A1, 1805B1. Either system 1900 or 2700 may adjust its one or more monitoring algorithms depending upon the state of the tissue.

Also, in this step 3307, either system 1900 or 2700 may automatically identify which tissue is traumatized and which is not. The systems 1900 and 2700 may make these determinations based on detected tissue characteristics (such as temperature, erythema, etc.). They systems 1900 and 2700 may then use non-traumatized tissue as a control relative to the monitored traumatized tissue as discussed above and below.

Next, in step 3310, the combined system 2700 obtain this preoperative baseline NIRS values for the patient from the sensors 405. In step 3315, the combined system 2700 may also receive a baseline set of values from traditional blood tests that have been applied to the patient prior to surgery. In this step 3315, this baseline set of values from traditional blood tests may be entered via the keyboard 2765 or these values may be transferred from another computer system to the intensive care unit 420C1 of the combined system 2700. The traditional blood tests may include, but are not limited to, those which establish levels of hemoglobin (Hgb) and hemocrit (Hct) within the blood of the patient.

In step 3317, the sensors 405 may be removed from the patient or they may be turned "off" while the patient undergoes surgery. In step 3319, which is similar to steps 2860, 3060, and step 3307, the medical practitioner may identify which sensors 405 are monitoring healthy or "non-traumatized" tissue and which sensors 405 are monitoring traumatized tissue. As noted above with respect to FIG. 26, injured tissue often becomes a "Privileged" area relative to other healthy body parts in that the body will typically maintain increased perfusion over other areas that are not injured even in times of poor global perfusion (hypotension). The oxygenation sensing system 1900 and/or combined system 2700 may be designed to accommodate or to account for the different physiological states of injured or traumatized tissue 1805A1, 1805B1. Either system 1900 or 2700 may adjust its one or more monitoring algorithms depending upon the state of the tissue.

Also, in this step 3319, either system 1900 or 2700 may automatically identify which tissue is traumatized and which is not. The systems 1900 and 2700 may make these determinations based on detected tissue characteristics (such as temperature, erythema, etc.). They systems 1900 and 2700 may then use non-traumatized tissue as a control relative to the monitored traumatized tissue as discussed above and below.

Next, in step 3320, the oxygenation sensors 405 are again applied to the patient after the surgery and in the same relative locations prior to surgery. In step 3325, the combined system 2700 monitors the NIRS values for the post operative patient from the sensors 405.

In step 3330, the combined system 2700 may receive blood test values for the post operative patient. Similar to step 3315, these values from traditional blood tests may be entered via the keyboard 2765 of these values may be transferred from another computer system to the intensive care unit 420C1. In step 3335, the combined system 2700 may automatically correlate the NIRS values from the sensors 405 against the values from the traditional blood tests. In this step 3335, the combined system 2700 may determine what type of blood products as well as what to a volume of blood transfusions may be necessary to restore "normal" levels of Hct and/or Hgb in the patient.

In step 3340, the combined system 2700 may display its recommendations regarding blood products and/or blood transfusion levels based on its assessment of the NIRS values taken from the sensors 405. In step 3345, the combined system 2700 may continue monitoring the NIRS values provided by the sensors 405.

In step 3350, the combined system 2700 may monitor the heart rate sensor 2725. In step 3355, the combined system 2700 may also monitor the blood pressure sensor 440 within the oxygenation sensing system 1900. In step 3360, the combined system 2700 may also monitor the respiration sensor 2705. The process then continues to step 3365 in FIG. 33B.

In step 3365 of FIG. 33B, the combined system 2700 may compare the monitored data from each of the sensors to a predetermined table or a set of tables such as Table 6 discussed above which lists values for one or more medical conditions. Next, in decision step 3370, the combined system 2700 A. determines if the data corresponds to the certain medical conditions outlined in the predetermined table(s) such as Table 6. This means that in decision step 3370, with the specific exemplary table of Table 6, the combined system 2700 may determine if the patient is experiencing an anemic condition and/or a shock condition based on the values in the table. One of ordinary skill the art recognizes that the invention is not limited to table 6 that outlines conditions and/or properties of anemia and shock. The invention may address any one of a variety of medical conditions based on the values listed for each sensor which are provided in the one or more predetermined tables.

If the inquiry to decision step 3370 is positive, then the "YES" branch is followed to step 3375. If the inquiry to decision step 3370 is negative, then the "NO" branch is followed and the process returns back to step 3325.

In step 3375, the combined system 2700 may activate an alarm and display the medical conditions on the display device 420C that appear to correspond with the values presented in the one or more predetermined tables. The alarm may comprise an audio or visual alarm (or both).

The combined system 2700 may also take into account the presence of pressors, also known as medication that may be used to increase the blood pressure and to potentially allow for increased perfusion in areas with elevated tissue pressure. Pressors are typically used to increase the cardiac output in order to maintain body perfusion. Pressors may be prescribed by the medical practitioner as a way to help prevent acute compartment syndrome by increasing the blood pressure so that it can over come increases in intra-compartmental pressures. If a particular patient happens to be on a pressor, then the combined system 2700 may be able to account for the use of this medication in an algorithm by accessing predetermined tables that have been derived from patients who have been on pressors while being monitored by the combined system 2700. Alternatively or in addition to, the medical practitioner may be warmed by the combined system 2700 then the NIRS values detected by the oxygenation sensing system 1900 may be altered by these types of medications. In a similar manner, the combined system 2700 may also take into account other drugs that impact other sensors of the combined system 2700 such as drugs that may impact respiration which may impact readings by the respiration sensor 2705 as well as drugs that may affect the heart which may impact the heart rate sensor 2725.

The blood pressure monitor for 440 may provide diastolic values as well as Mean arterial pressure (MAP) values. The combined system 2700 may use these values to assess artier vascular function as understood by one of ordinary skill the art. The combined system 2700 may detect or sense a presence of shock when it detects that the blood pressure values have decreased. An arterial line may be provided with the blood pressure monitor 442 help monitor the blood pressure of a patient.

The temperature sensor 2710 of the combined system 2700 may be designed to detect key temperature changes which may affect ability of enzymes to perform efficiently. The performance of enzymes may have an impact on blood clotting, oxygenation transportation (hemoglobin), and other functions known to one of ordinary skill the art.

The pulse-ox sensor 2710 may be used to monitor lung capacity for oxygen exchange. The data from this sensor 2710 may allow for insight into the whole body oxygen transport.

The altitude sensor 2740 may be useful in situations in which the patient is transported through various different altitudes such as during military operations in which a patient is transported by helicopter or flight evacuation planes to a medical facility. The altitude sensor 2740 may be able to assess and determine causes of changes in pressure within closed compartments such as, but not limited to, the fascia of extremities, organs, intracranial pressures, and the like.

The heart rate sensor 2725 may be able to detect circulatory capabilities of the subject and may help detect the presence of shock. The combined system 2700 may monitor an increased heart rate with the heart rate sensor 2725 and decreased NIRS values with the oxygenation sensing system 1900 which may cause the combined system to sound the audible alarm 1907 and/or one of the visual alarms 420CI-CIII to suggest to the medical practitioner that a transfusion may be needed by the patient.

The respiration sensor 2705 may be able to indicate whether a patient has poor oxygenation are not. The combined system 2700 may use the signals from the respiration center 2705 and the NIRS values from the oxygenation sensing system 1900 to determine whether a patient has poor ability to oxygenate, and if this condition exists, the combined system 2700 may activate an alarm to suggest increasing oxygen supplementation or intubation of the patient.

The pH sensor 2710 may indicate poor resuscitation if the combined system 2700 also detects changes in NIRS values from the oxygenation sensing system 1900.

The demographic data input 2702 may help the combined system 2700 determine if a patient has certain diseases which may affect perfusion, such as diabetes, peripheral neuropathy, and small vessel disease. The demographic data input 2702 may also help the combined system to determine if a patient may have lung disease, conditions associated with smoking/EtOH (Alcohol), and conditioned associated with old age. The demographic data input 2702 may also allow for a medical practitioner to input a sex of the patient as well as the ability to assign pigment values based on pigment type. If pigment data is provided by the medical practitioner, then the combined system 2700 may access predetermined charts such as the pigment chart developed by Taylor et al. 2006.

The NIRS sensors 405 of the combined system 2700, and particularly of the oxygenation sensing system 1900, may be provided with different sizes to correspond with patients having various sizes. For example, the NIRS sensors 405 may be provided in at least three different sizes such as small, medium, and large as illustrated in FIG. 34. These variations in sizes for the sensors 405 may allow for the monitoring of various different body sizes such as for fat, average, and skinny people due to the different scan depths that may be achieved through varying the distance "d" between the light source 510 and the light receiver 515 for a particular sensor 405. The sizes of the sensors 405 may also be tailored for the specific body part being monitored, such as for the leg, forearm, thigh, and/or foot as illustrated in FIG. 35. In FIG. 35, the sensor 405 has a predetermined shape that corresponds to a finger of a human. The variations in sizes for the sensors 405 may allow for the isolation of tissue at specific depths based on the body part being monitored. The sensors 405 may be provided with predetermined scan depths based on a MRI study in which limbs of the human body have been scanned to determine the average depths for each compartment of the human body. Scan depths for each sensor 405 can be achieved by the type of light source provided on each sensor 405 as well as the geometry of the sensor 405 and arrangement in a sensor array 805 for the oxygenation sensing system 1900 in order to best fit the compartment being monitored.

The system 2700 may communicate with multiple sensor types that are coupled to the system 2700 which includes the oxygenation sensing system 1900. Other sensor types may include, but are not limited to, a cerebral monitor, an organ monitor such as the heart rate sensor 2725 and the respiration sensor 2705, a spine monitor, and other like monitors. The system 2700 may provide and display directions for use of a sensor, such as each sensor 405 and the initiation/calibration of each sensor 405 as it establishes communications with system 2700.

The system 2700 can provide sensor directions in order to educate medical practitioners on how to use/place sensors 405 at start up when either the system 2700 is powered on or when a new sensor 405 establishes communications with the system 2700. The system 2700 may also allow a medical practitioner to bypass the instructions/directions on the system 2700 if the medical practitioners familiar with the device/application of the system 2700.

The system 2700 may have multiple different sockets or inputs from multiple different pad/monitoring input sources based on the function of a particular sensor 405. Different sockets or inputs may allow for different uses of a particular sensor 405. The sockets or inputs may have labels 3605 which match labels positioned on each sensor 405 so that correct sockets and inputs are utilized in so that medical practitioners are not confused when attaching the sensors 405 to the system 2700 as illustrated in FIG. 36. Each socket can be made to only fit certain sensors that will be labeled specifically for that use. In other words, each socket 3610 of a sensor 405 or sockets 3610 for a set of sensors 405 may be provided with unique geometric shapes as illustrated in FIG. 36. Additionally, based on what socket is used, different algorithms can initiated based on what function the sensor 405 for which it is to be used.

A disconnect mechanism 3615 as illustrated in FIG. 36 can be incorporated into the system 2700 that allows the sensors 405 to be disconnected quickly and easily for patient transfer, etc. This mechanism 3615 will allow for easy disconnection but also easy reconnection, so sensors 405 are not reconnected incorrectly. Color coding 3620 or different connection mechanisms for each line can insure appropriate reconnection to the accurate site. By using different fitting connection/locking mechanisms 3615 for each line, it insures that only the correct two ends of a line can be attached together.

As noted previously, sensors 405 to may store a unique identifier for the system 2700 to recognize. Therefore, if the sensors 405 are unplugged then reattached, the information will be retrieved from previous measurements. In this way, if a change from previous readings occurred while the sensor 405 was unplugged (i.e., the patient was taken for a diagnostic test) the change would be recognized by the system 2700 once the sensor 405 was reattached.

Additionally, a memory device and mobile monitor may be provided that can be temporarily attached to sensors 405 in order to retain data while the sensors are unplugged from the combined system 2700. As noted above, the sensor 405 itself could retain data for processing after it removal or if the sensor was switched between different intensive care units 420C1.

The system 2700 may be provided with a keyboard/keypad 2765 so that patient information, such as demographic data 2702, may be entered by a medical practitioner. The keyboard/keypad 2760 5A be coupled to the system 2700 by a wired or wireless link.

System 2700 may take advantage of controls also referred to as uninjured or areas of anatomy which are not of interest to the system 2700. The system 2700 may take baseline measurements of the controls in order to compare them with the areas of anatomy which are of interest to the system 2700. For bilateral lower extremity injuries, system 2700 may use one or more forearms as a control. The upper extremity of the patient should usually be shunted if it is uninjured relative to the bilateral lower extremity injuries. The system 2700 may also take into account that injured tissue may become hyperemic and adjust its measurements accordingly.

The system 2700 may help the medical practitioner locate the compartments of a human leg. Specifically, the system may help the medical practitioner locate the Anterior, Lateral & Superficial Compartments (these compartments can be accessed over any area due to the superficial nature), and Deep posterior (which is usually more difficult to get a reading). The system 2700 can help the medical practitioner locate the most superficial portion of the Deep posterior which may be generally found at the posterior and medial boarder of tibia and is often the best place to take a reading with a sensor 405. As noted previously, the system 2700 may provide an initiation of monitoring directions to medical practitioners not familiar with ACS to insure appropriate placement of pads.

Figure 28:
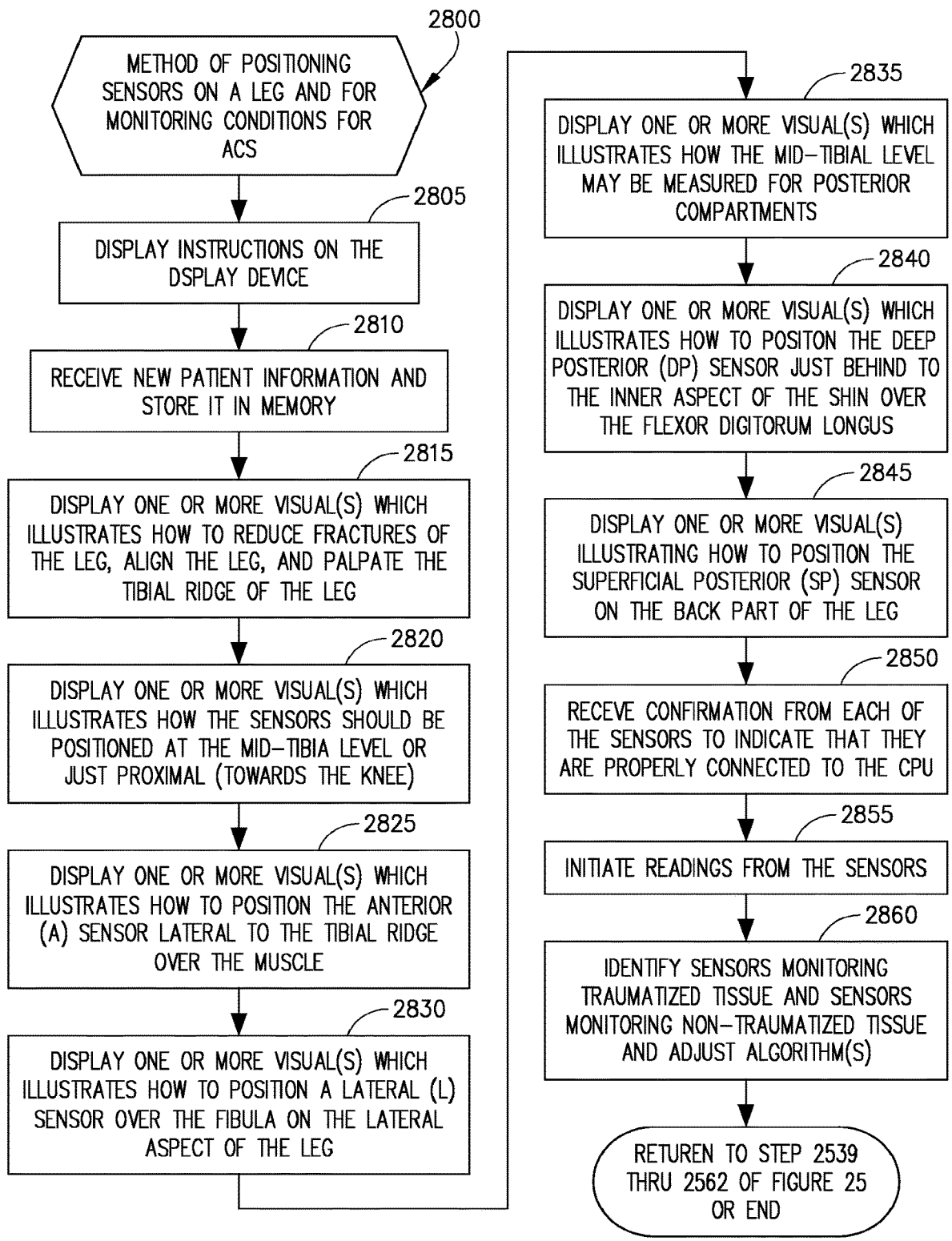
FIG. 28 is a logic flow diagram illustrating an exemplary method for positioning sensors on a leg of an animal body, such as a human, for monitoring conditions for ACS according to one exemplary embodiment of the invention.

Referring to FIG. 28, this figure is logic flow diagram illustrating an exemplary method 2800 for positioning sensors 405 on a leg and for monitoring conditions for ACS according to one exemplary embodiment of the invention. This method 2800 describes steps that can be used with either the oxygenation sensing system 1900 or the combined system 2700 as discussed above. The method 2800 may also be part of method 2500 of FIG. 25 in that the steps of method 2800 could be part of Step 2521 of FIG. 25 in which proper positions for sensors 405 are identified.

Step 2805 is the first step in the process 2800 in which instructions are displayed on the display device 4208/420C for entering new patient information into the combined system 2700 or into the oxygenation sensing system 1900. New patient information made include, but is not limited to, name, address, unique identifiers assigned by a medical facility, insurance information, and the like. This information can be entered in using a keyboard or keypad 2765.

Next, in step 2810 the combined system 2700 or the oxygenation sensing system 1900 may receive the new patient information and store it in memory, such as memory storage 2760 of FIG. 27. Next, in step 2815, one or more visual(s) are displayed on the display device 4208/420C which illustrate how to reduce fractures of the leg 100, a line the leg 100, and palpate the tibial ridge of the leg 100. One exemplary visual for step 2815 is provided in FIG. 29A.

Figure 29A:
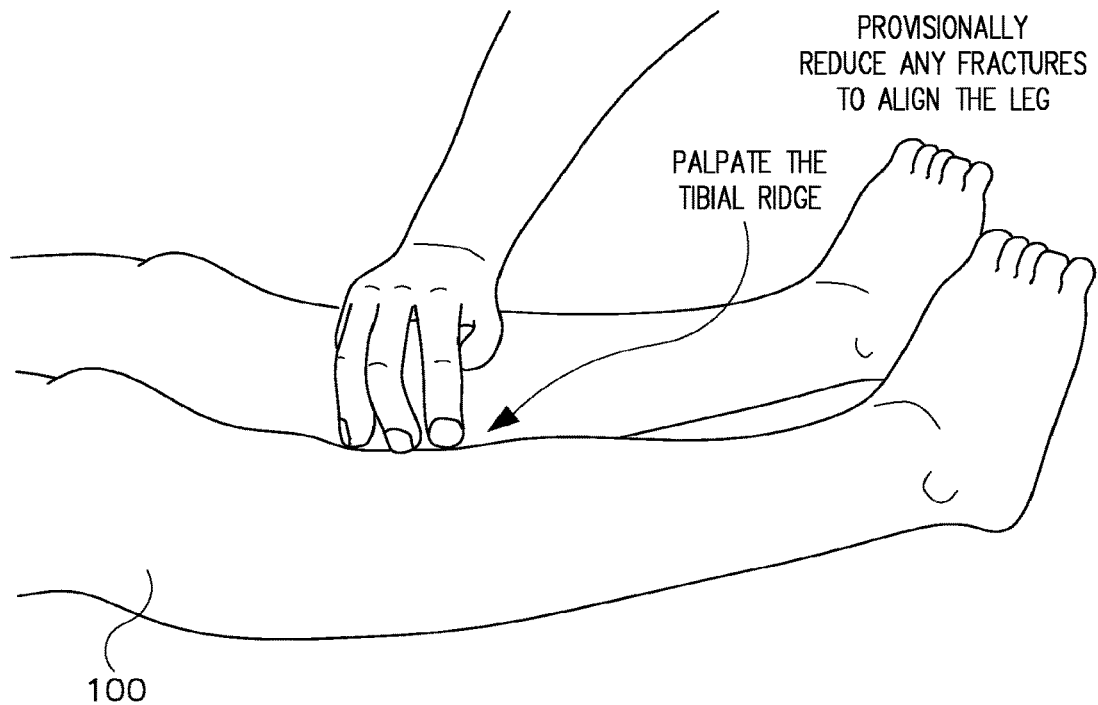
Figure 29B:
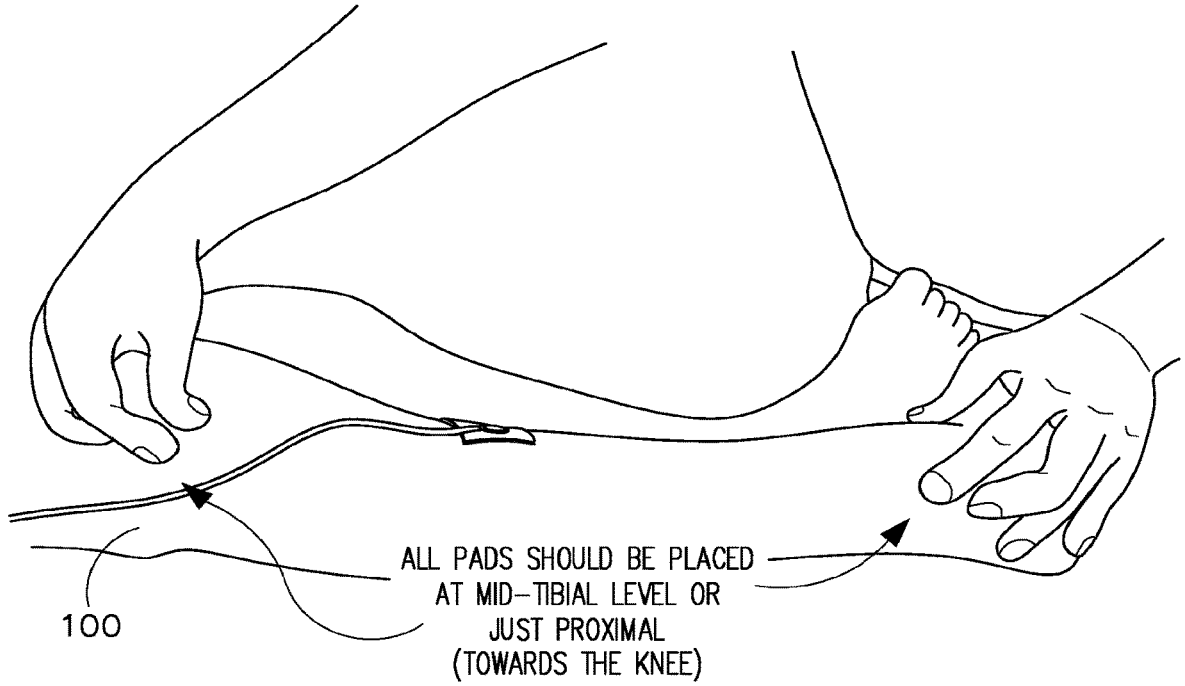

Referring briefly to FIG. 29A, this figure illustrates the right leg 100 of a patient and how a medical practitioner may provisionally reduce any fractures to align the leg 100. Referring back to FIG. 28, in step 2820 one or more visuals may be displayed on the display device 4208/420C that illustrate how the sensors 405 should be positioned at the mid-tibial level or just proximal (towards the knee), as provided in FIG. 29B. Visuals may include, but are not limited to, graphical computer-generated still images that may comprise digital photographs and text, as well as video which comprises moving images. The visuals may also comprise computer-generated images that provide illustrations instead of digital photographs, or any combination thereof. The visuals may or may not be accompanied by audio information such as a narrator describing proper placement of the sensors 405.

Figure 29C:
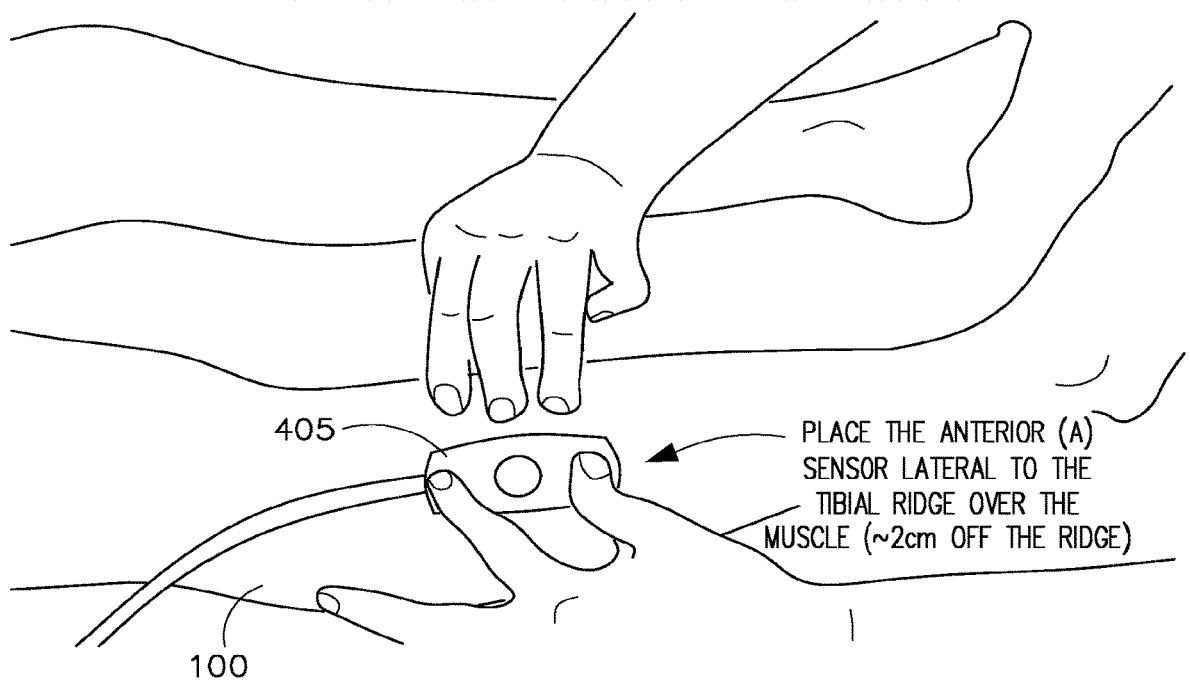
Figure 29D:
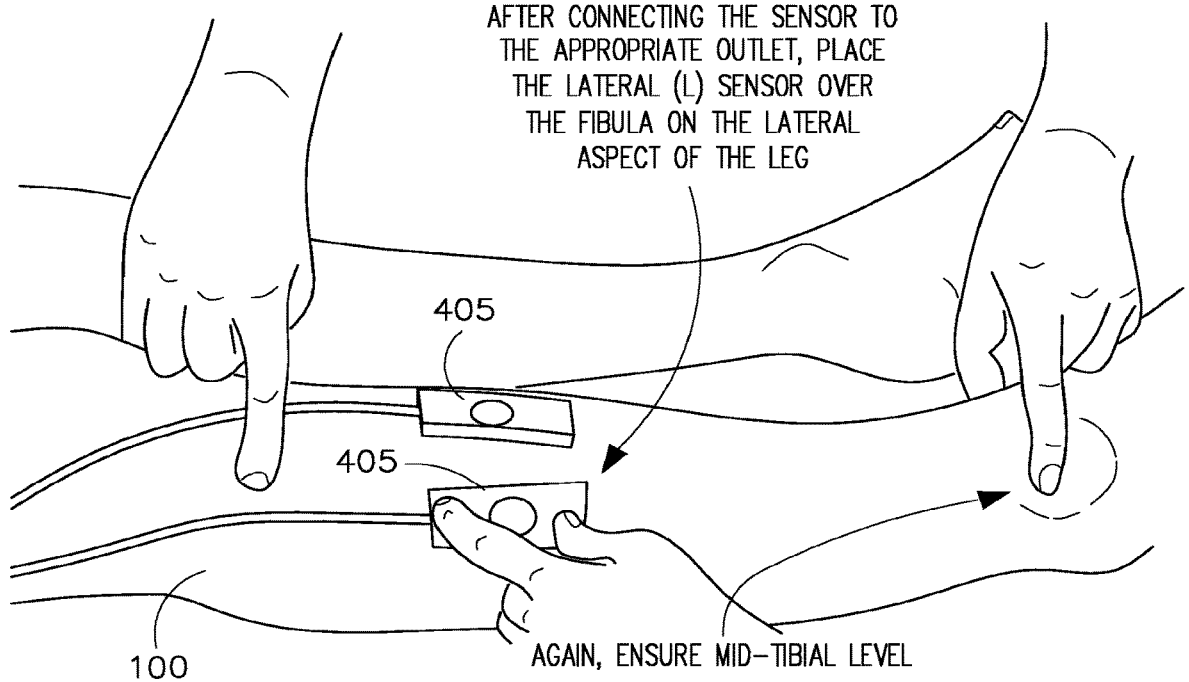

In step 2825, one or more visuals may be displayed to illustrate how to position the anterior (A) sensor 405 lateral to the tibial ridge over the muscle. In most cases, this position will be about or approximately two centimeters off the ridge, as provided in FIG. 29C. Next, in step 2830, one or more visuals may be displayed on the display device 4208/420C to illustrate how to position a lateral (L) sensor 405 over the fibula on the lateral aspect of the leg 100, as provided in FIG. 29D.

Figure 29E:
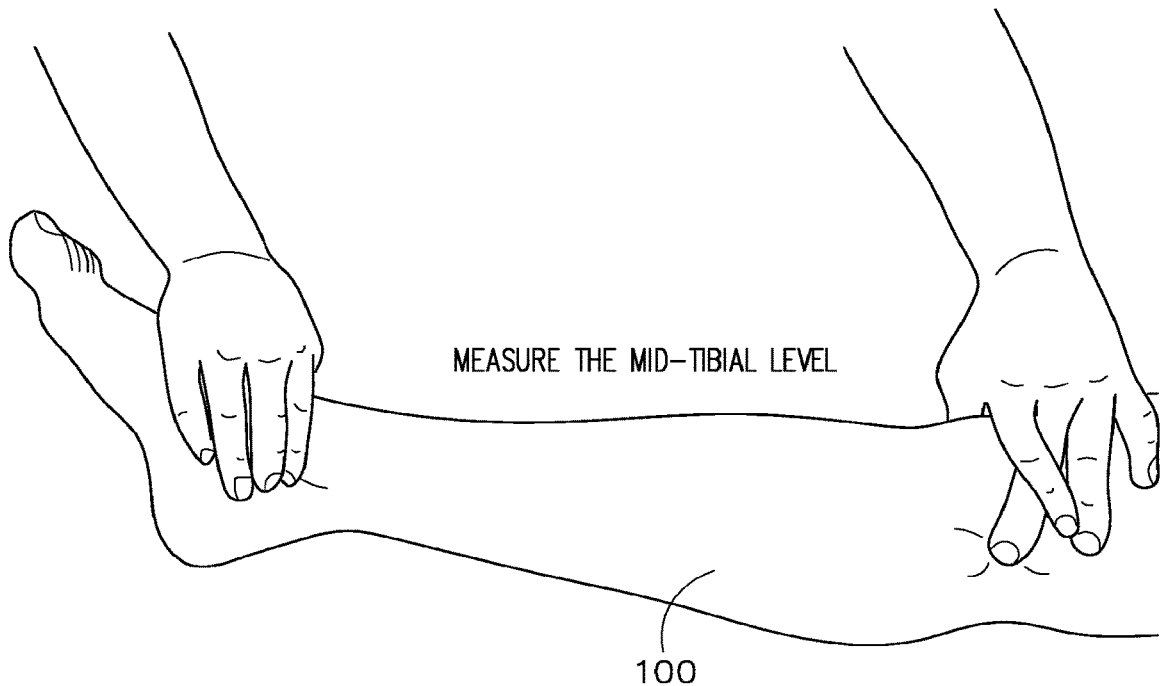
Figure 29F:
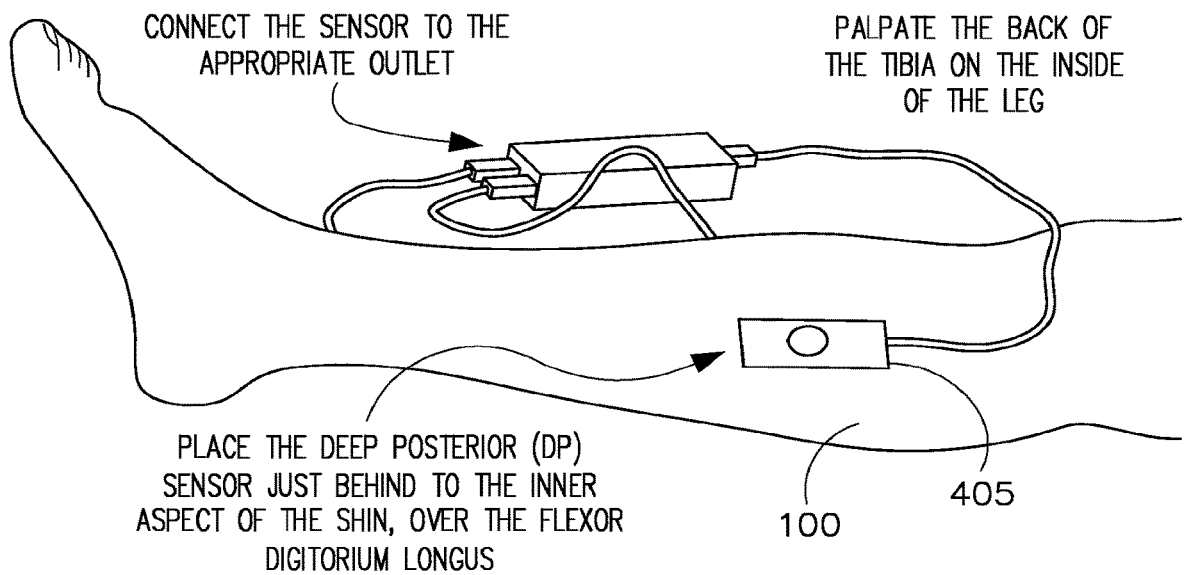

In step 2835, one or more visuals may be displayed on the display device 4208/420C to illustrate how the mid-tibial level may be measured, as provided in FIG. 29E. In step 2840, one or more visuals may be displayed on the display device 4208/420C illustrating how to position the deep posterior (DP) sensor 405 just behind to the inner aspect of the shin over the flexor digitorum longus, as provided in FIG. 29F.

Next in step 2845, one or more visuals illustrating how to position the superficial posterior (SP) sensor 405 on the back part of the leg 100 may be provided on the display device 4208/420C, as provided in FIG. 29G. Subsequently, in step 2050, the system 2700 or oxygenation sensing system 1900 may receive confirmation from each of the sensors 405 to indicate that they are properly connected to the CPU 420A. In step 2855, the system 2700 may initiate readings from the sensors 405.

In step 2860, the medical practitioner may identify which sensors 405 are monitoring healthy or "non-traumatized" tissue and which sensors 405 are monitoring traumatized tissue. As noted above with respect to FIG. 26, injured tissue often becomes a "Privileged" area relative to other healthy body parts in that the body will typically maintain increased perfusion over other areas that are not injured even in times of poor global perfusion (hypotension). The oxygenation sensing system 1900 and/or combined system 2700 may be designed to accommodate or to account for the different physiological states of injured or traumatized tissue 1805A1, 1805B1. Either system 1900 or 2700 may adjust its one or more monitoring algorithms depending upon the state of the tissue. Also, in this step 2860, either system 1900 or 2700 may automatically identify which tissue is traumatized and which is not. The systems 1900 and 2700 may make these determinations based on detected tissue characteristics (such as temperature, erythema, etc.). They systems 1900 and 2700 may then use non-traumatized tissue as a control relative to the monitored traumatized tissue as discussed above and below. The process then continues, and it may continue with Steps 2539 through 2562 of FIG. 25.

In addition to helping the medical practitioner locate the appropriate positions for sensors that monitor the compartments of the leg 100, the system 2700 may easily measure and monitor conditions for acute compartment syndrome (ACS) in a forearm which is known to one of ordinary skill the art as the second most common area for ACS relative to the legs. The system 2700 may easily monitor the four different compartments of a forearm which include the following: A) mobile wad (extensor carpi radilis longus & brevis and the brachioradilis); B) Deep flexors—flexor digitorum profundus; C) Superficial flexors—flexor digitorum superficialis, other flexors (wrist) & pronator teres; and D) Extensors—wrist & finger extensors & supinator.

The system 2700 may provide specific placement instructions including illustrations or video for positioning sensors 405 for measuring and monitoring ACS in a forearm. The system 2700 may help the medical practitioner locate the muscles in the forearm. The system 2700 may help the medical practitioner identify these muscles by indicating that the muscles are often found more in the proximal than the distal one half of the forearm when the muscle belly of the forearm is typically located. The system 2700 may help the medical practitioner place the sensors 405 in the proximal one half of the forearm and over the distal one half of the forearm as possible.

The system 2700 may help the medical practitioner to account for the rotation of a forearm to ensure appropriate monitoring and placement of the sensors 405. The system 2700 may prompt the medical practitioner to position the sensors 405 when the forearm is in neutral rotation in which the thumb of the patient is pointing forward or ventral. The system 2700 may also monitor conditions in any location of the distal portion of the arm, such as but not limited to, a hand, finger, palm thenar, hypothenar eminence, wrist, etc.

Figure 30:
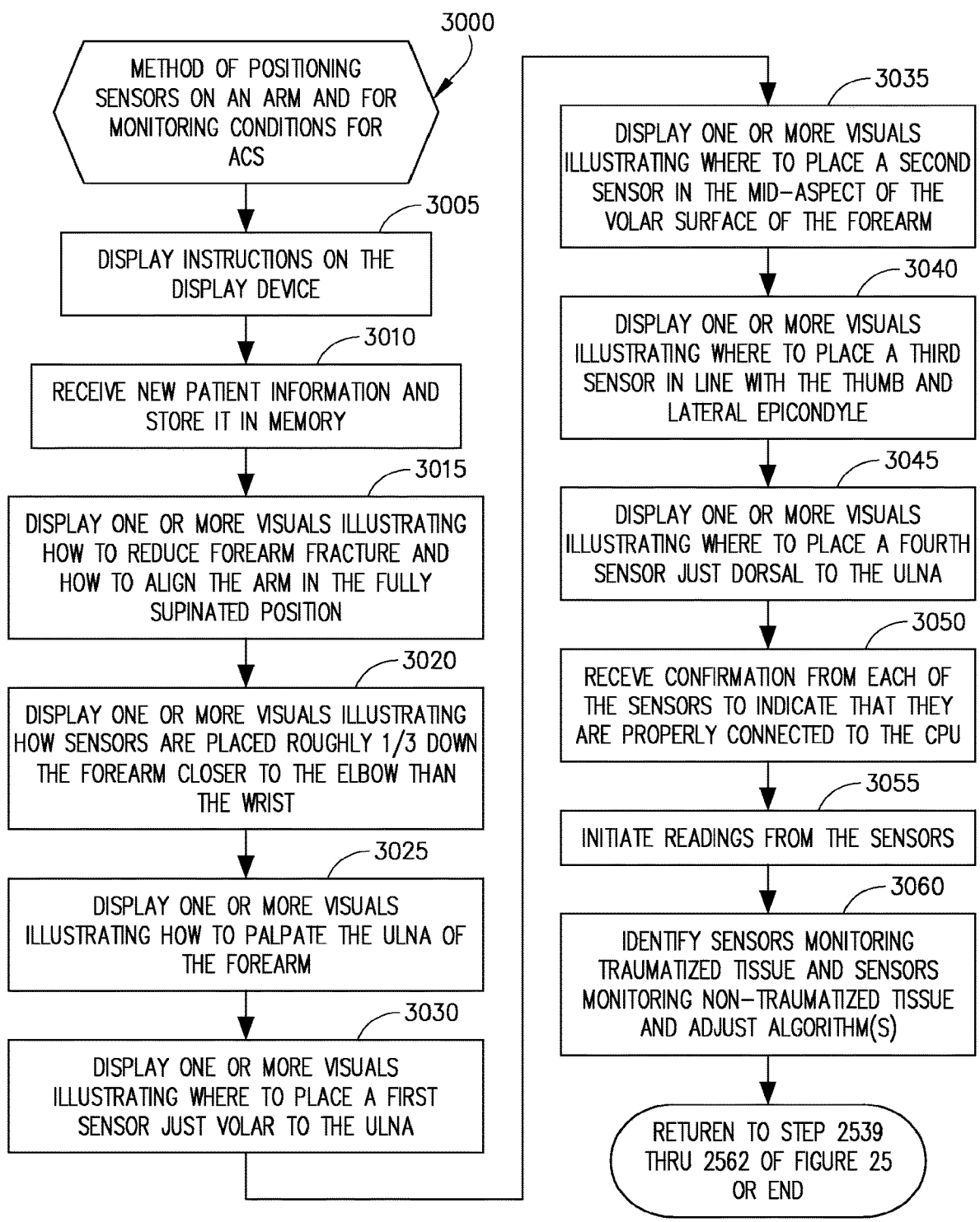
FIG. 30 is a logic flow diagram illustrating an exemplary method for positioning sensors on an arm of an animal body, such as a human, for monitoring conditions for ACS according to one exemplary embodiment of the invention.

Referring to FIG. 30, this figure is logic flow diagram illustrating an exemplary method 3000 for positioning sensors 405 on an arm 3100 and for monitoring conditions for ACS according to one exemplary embodiment of the invention. This method describes steps that can be used with either the oxygenation sensing system 1900 or the combined system 2700 as discussed above. The method 3000 may also be part of method 2500 of FIG. 25 in that the steps of method 3000 could be part of Step 2521 of FIG. 25 in which proper positions for sensors 405 are identified.

Step 3005 is the first step in the process 3000 in which instructions are displayed on the display device 4208/420C for entering new patient information into the combined system 2700 or into the oxygenation sensing system 1900. New patient information made include, but is not limited to, name, address, unique identifiers assigned by a medical facility, insurance information, and the like. This information can be entered in using a keyboard or keypad 2765.

Next, in step 3010 the combined system 2700 or the oxygenation sensing system 1900 may receive the new patient information and store it in memory, such as memory storage 2760 of FIG. 27. Next, in step 3015, one or more visuals illustrating how to reduce forearm fracture and how to align the arm in the fully supinated position may be provided on the display device 4208/420C, as provided in FIG. 31A. Visuals may include, but are not limited to, graphical computer-generated still images that may comprise digital photographs and text, as well as video which comprises moving images. The visuals may also comprise computer-generated images that provide illustrations instead of digital photographs, or any combination thereof. The visuals may or may not be accompanied by audio information such as a narrator describing proper placement of the sensors 405.

Figure 31B:
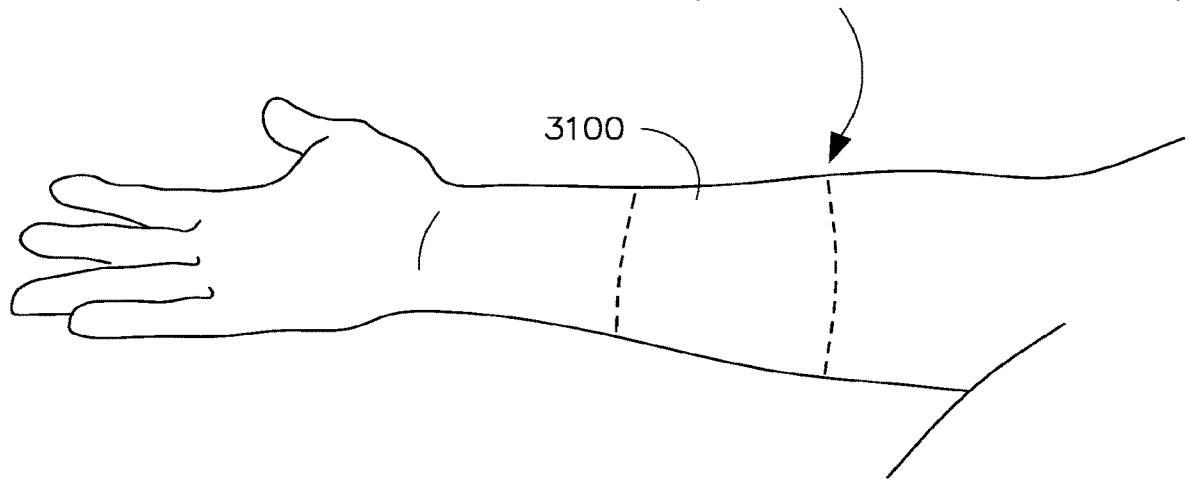
Figure 31C:
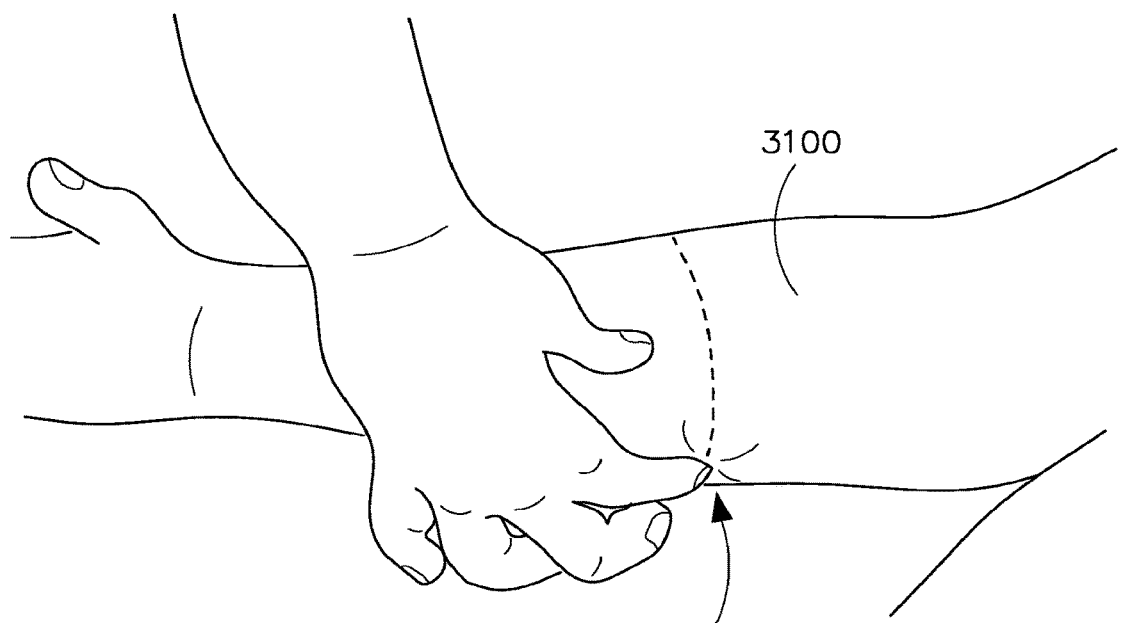

Next, in step 3020 one or more visuals illustrating how sensors 405 are placed roughly ⅓ down the forearm 3100 closer to the elbow then the wrist, may be provided on display device 4208/420C, as set forth in FIG. 31B. In step 3025, one or more visuals illustrating how to palpate the ulna of the forearm 3100 may be provided on the display device 4208/420C, as provided in FIG. 31C.

Figure 31D:
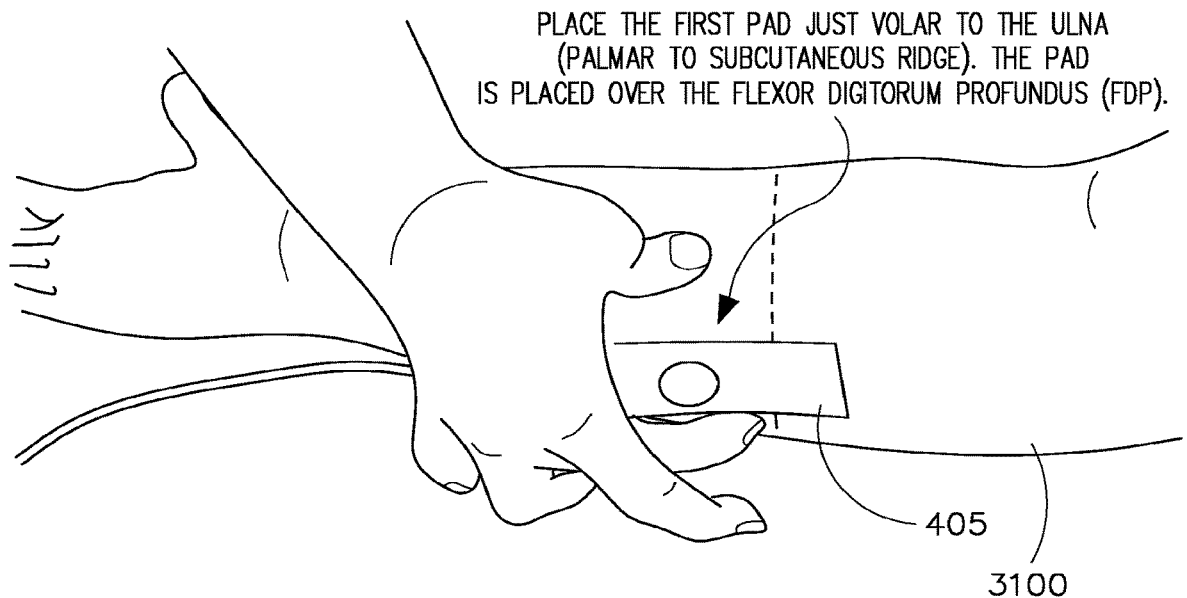
Figure 31E:
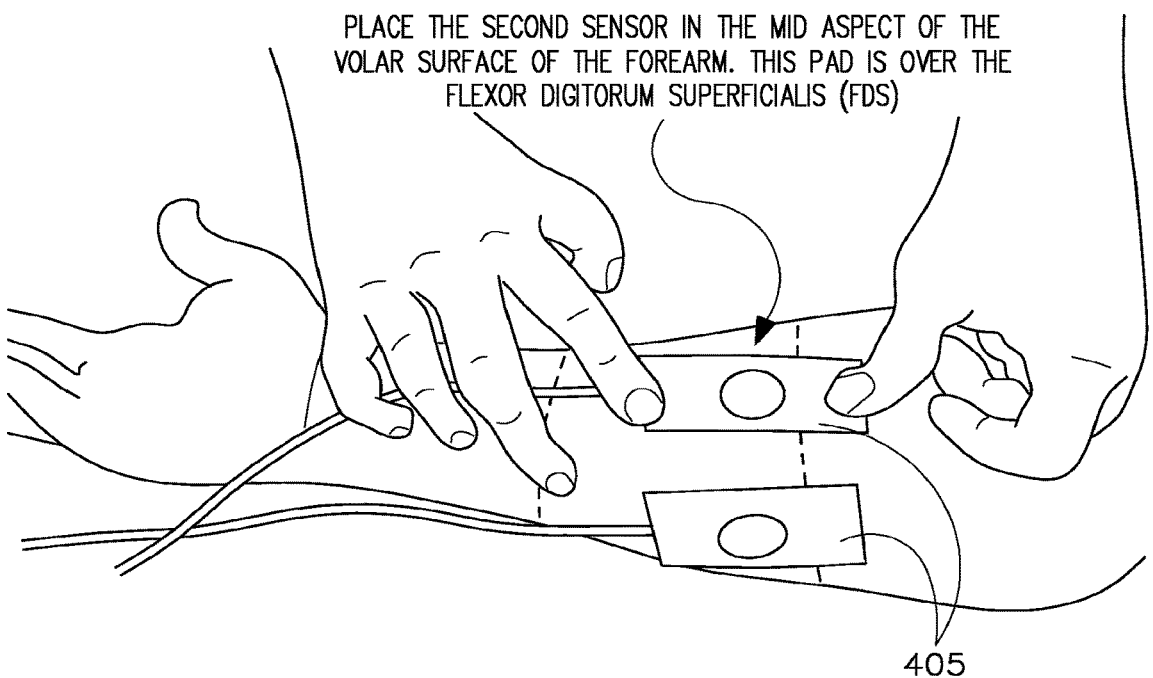

In step 3030, one or more visuals illustrating where to place a first sensor 405 just volar to the ulna, as provided in FIG. 31D, may prove provided on the display device 4020. In step 3035, one or more visuals illustrating where to place a second sensor 405 in the mid-aspect of the volar surface of the forearm 3100 may be provided on the display device 4020, as illustrated in FIG. 31E. Subsequently, in step 3040, one or more visuals illustrating where to place a third sensor 405 in line with the thumb and lateral epicondyle may be provided on the display device 420, as set forth in FIGS. 31F-G.

Next, in step 3045, one or more visuals may be displayed on the display device 4020 illustrating where to place a fourth sensor just dorsal to the ulna, as set forth in FIG. 31H. In step 3050, the system 2700 or oxygenation sensing system 1900 may receive confirmation from each of the sensors 405 to indicate that they are properly connected to the CPU 420A. In step 3055, the system 2700 may initiate readings from the sensors 405.

In step 3060, which is similar to step 2860, the medical practitioner may identify which sensors 405 are monitoring healthy or "non-traumatized" tissue and which sensors 405 are monitoring traumatized tissue. As noted above with respect to FIG. 26, injured tissue often becomes a "Privileged" area relative to other healthy body parts in that the body will typically maintain increased perfusion over other areas that are not injured even in times of poor global perfusion (hypotension). The oxygenation sensing system 1900 and/or combined system 2700 may be designed to accommodate or to account for the different physiological states of injured or traumatized tissue 1805A1, 1805B1. Either system 1900 or 2700 may adjust its one or more monitoring algorithms depending upon the state of the tissue.

Also, in this step 3060, either system 1900 or 2700 may automatically identify which tissue is traumatized and which is not. The systems 1900 and 2700 may make these determinations based on detected tissue characteristics (such as temperature, erythema, etc.). They systems 1900 and 2700 may then use non-traumatized tissue as a control relative to the monitored traumatized tissue as discussed above and below. The process then continues, and it may continue with Steps 2539 through 2562 of FIG. 25.

The combined system 2700 may execute algorithms that are designed for specific medical conditions. For example, the combined system 2700 may execute an algorithm that is specifically for traumatized tissue. According to such a traumatized tissue algorithm, the system 2700 could record NIRS values from the oxygenation system 1900 on the order of minutes instead of smaller increments like seconds or milliseconds since conditions for traumatized tissue do not change that rapidly relative to seconds or milliseconds. However, changes may be detected across a scale of minutes such as on the order of every five minutes or so. One of ordinary skill in the art will appreciate that the invention is not limited to taking readings every five minutes and can include other magnitudes depending on the tissue/patient being monitored. With monitoring traumatized tissue, one of ordinary skill in the art recognizes that a medical practitioner usually only needs to know trends conveyed by the collected data to assess healing progress or any complications.

For this specific yet exemplary application, the system 2700 in monitoring traumatized tissue may use delays to determine if changes are maintained or if they are artifact (such as changes detected due to patient movement). The system 2700 may be smooth out data by using these delays. The system 2700 may signal an audio or visual alarm (or both) if a trend is maintained for predetermined period of time that can be adjusted by the medical practitioner. For example, the medical practitioner could request the system 2700 to activate an alarm if a trend of data is constant over a period of two minutes, five minutes, or thirty minutes, just to name a few. These periods set by the medical practitioner can be set to any length as desired by the medical practitioner.

The system 2700 may also delay or stop readings for a predetermined period of time in response to other devices acting on a patient. For example, oxygenation system sensing 1900 may include a blood pressure cuff in addition to its blood pressure probe 440. The system 2700 may cease readings made by the oxygenation sensing system 1900 every time the blood pressure cuff cycles, since perfusion will be decreased when the blood pressure cuff is expanded on the patient. The system 2700 should not activate an alarm every time the blood pressure cuff is inflated.

The system 2700 may have the function/feature of accessing stored data from previous readings. Such a function/feature is beneficial for when patients need to be disconnected to go to bathroom, to get tests done, or undergo surgery. Each sensor 405 may be provided with a unique serial number or microchip so that the central controller 420C1 may recognize previous data from a particular sensor 405 when it reviews its memory 2760. In some exemplary embodiments, each sensor 405 may be provided with local memory storage 635 (See FIG. 6C) on the sensor 405 itself.

Each sensor 405 may be provided with labels to provide a user with information on what compartment the sensor 405 should be placed on (A or Ant or Anterior for the Anterior compartment or a number on it which then is used in the set up instruction). The combined system 2700 may permit set up instructions to be accessed from any screen provided on the display 4208/420C to assist the medical practitioner with correct placement of the sensors 405 on the tissue of interest.

The system 2700 may generate printed labels for each compartment that can be used by the medical practitioner. The medical practitioner can apply these labels on the tissue(s) of interest so that sensors 405 are not switched if a sensor 405 is removed temporarily for some reason.

The central controller 420C1 may be provided with one or more algorithms to determine if the tissue being monitored is a control or if it is the injured tissue based on detected tissue characteristics (such as temperature, erythema, etc.). Once the central controller 420C1 determines if the monitored tissue is a control or injured tissue, then it can treat readings appropriately. In other words, the central controller 420C1 may shut off alarms for any tissue that it has determined to be designated as a control relative to an injured tissue being monitored. The designation of control or study/injured can be assigned manually for each sensor.

With control tissue, the system 2700 may determine that if control readings are going down or if a downward trend is detected, then the system 2700 may alert the medical practitioner that a systemic problem, such as a hypotensive condition, may be present. The system 2700 may also account for body positions of the patient. The system 2700 may have predetermined off-sets to adjust for positional effects of the patient (such as the lying down, seated, and standing positions). Each sensor 405 may be provided with a motion or gravity sensing device, such as accelerometer(s), to determine a relative position of a patient and/or position of the tissue of interest.

Hardware Components Specific for ACS

The sensors 405 may be formed as a horse tail sensor that comprises one wire that breaks into four sensors with one to two feet or longer of cord for placement on a leg or an arm. One of ordinary skill in the art recognizes that the invention is not limited to the exemplary dimensions disclosed and that other dimensions are well within the scope of the invention. Each sensor 405 may be provided with a single insertion plug to allow appropriate monitoring (with each sensor labeled). A set, such as four sensors 405 grouped together, may be plugged in as one unit so each sensor does not plug in individually and allow for them to be switched, such as illustrated in FIG. 5B.

Each sensor 405 may be provided with physical markings such as with permanent letters and/or numbers to allow accurate placement of sensors 405, such as illustrated in FIG. 6A. These permanent physical markings cannot be removed or switched (permanent at time of manufacturing). Additionally, for some sensors 405, a right or left (R/L) designation may also be provided if a particular sensor 405 is sized and shaped for a particular side of an extremity or body part, as illustrated in FIG. 35. If each sensor 405 is provided with a unique identifier readable by the central controller 420C1, then the central controller can alert the medical practitioner that a particular sensor has been inadvertently relocated by comparing present readings with current readings.

Each sensor 405 may be provided with mechanical features, such as plugs with geometries that are easily gripped and matched appropriately with a corresponding socket so that they are easy for medical practitioners to plug in and to remove without inappropriately/inadvertently switching sensors 405, as illustrated in FIG. 36.

The system 2700 may provide visual instructions on the display device 4208/420C on how to place sensors 405 at start up. These instructions may be accessible at any time for reattachment of the sensors 405 to the CPU 420A. Each sensor 405 may be provided with batteries having a life of at least several hours to allow a patient to be transported. However, other battery life sizes are possible and within the scope of the invention.

A system where the sensors 405 may be detached from the monitoring system 2700 to allow for a smaller mobile device may be provided. This smaller system would still record data, but not have the display capabilities, interpretational functions, and/or an alarm system. However, it would have a battery, sensors 405, and memory to allow for mobile monitoring.

The system 2700 may comprise algorithms that are specific or tailored for tissue/regions of interest. For example, the system 2700 may have algorithms specific to a forearm 3100, in which proximal sensors 405 are evaluated or weighted secondary to tendon sensors 405 placed distally. The algorithm may adjust or take into account any rotation of the arm. Sensors 405 for the arm can be positioned distally such as on, but not limited to, the fingers, palm, thenar, and hypothenar eminence, just to name a few. For the leg, distal regions for sensors 405 may include, but are not limited to, a plantar surface, toes, and the ankle. For torso regions, sensors 405 may be positioned on the abdomen as well for abdominal compartment syndrome or any other area of the body, like the spinal cord, brain injury, hand, foot, thigh, buttocks, etc.

It should be understood that the foregoing relates only to illustrate the embodiments of the invention, and that numerous changes may be made therein without departing from the scope and spirit of the invention as defined by the following claims.

What is claimed is:

1. A spectrophotometric-based system for monitoring blood perfusion in a limb, the system comprising:
a first near-infrared sensor configured for application to a target compartment of a target limb and a second near-infrared sensor configured for application to a contralateral compartment of a contralateral limb, wherein each of the first near-infrared sensor and the second near-infrared sensor comprises:
a light source for emitting near-infrared energy into a compartment of tissue;
a light receiver for receiving near-infrared energy exiting the compartment of tissue; and
an alignment mechanism;
a visual display device in electronic communication with the first near-infrared sensor and the second near-infrared sensor, wherein the visual display device is configured to:
at startup, and before receipt of any readings from the first and second near-infrared sensors, provide to a user on-screen instructions for using the alignment mechanisms of the first and second near-infrared sensors to orient each, respectively, with the target compartment and the contralateral compartment;
display hemoglobin oxygen saturation readings received from each of the first near-infrared sensor and the second near-infrared sensor; and
indicate, by an audible and/or visual alarm output in addition to the oxygen saturation readings, compartment syndrome in the target compartment of the target limb when a first hemoglobin oxygen saturation reading associated with the first near-infrared sensor equals or is less than a second hemoglobin oxygen saturation reading associated with the second near-infrared sensor.

2. The system of claim 1, wherein the visual display device is further configured to indicate a warning alarm when a first hemoglobin oxygen saturation reading associated with the first near-infrared sensor drops by a predefined amount.

3. The system of claim 1, wherein the first near-infrared sensor comprises an array of near-infrared sensors, each configured to generate a unique hemoglobin oxygen saturation reading.

4. The system of claim 3, wherein the display is further configured to indicate an expanding hematoma based on a comparison of the unique hemoglobin oxygen saturation readings of the array of near-infrared sensors.

5. The system of claim 1, wherein at least one of the first near-infrared sensor and the second near-infrared sensor is a stacked compartment sensor comprising a plurality of light receivers.

6. The system of claim 1, wherein at least one of the first near-infrared sensor and the second near-infrared sensor comprises a material layer between a substrate of the sensor and a patient skin surface, the material layer operable to affect a scan depth of the sensor.

* * * * *